US012127851B2

United States Patent
McCarthy et al.

(10) Patent No.: US 12,127,851 B2
(45) Date of Patent: Oct. 29, 2024

(54) SYSTEMS AND METHODS FOR AUGMENTED NEUROLOGIC REHABILITATION

(71) Applicant: MedRhythms, Inc., Portland, ME (US)

(72) Inventors: Owen McCarthy, Gorham, ME (US); Brian Harris, Gray, ME (US); Alex Kalpaxis, Glendale, NY (US); Jeffrey Chu, Portland, ME (US); Brian Bousquet-Smith, Portland, ME (US); Eric Richardson, Portland, ME (US)

(73) Assignee: MEDRHYTHMS, INC., Portland, ME (US)

( * ) Notice: Subject to any disclaimer, the term of this patent is extended or adjusted under 35 U.S.C. 154(b) by 466 days.

(21) Appl. No.: 17/381,899

(22) Filed: Jul. 21, 2021

(65) Prior Publication Data
US 2021/0345947 A1    Nov. 11, 2021

Related U.S. Application Data

(63) Continuation-in-part of application No. 16/569,388, filed on Sep. 12, 2019, now Pat. No. 11,779,274,
(Continued)

(51) Int. Cl.
*A61B 5/11* (2006.01)
*A61B 5/00* (2006.01)
(Continued)

(52) U.S. Cl.
CPC ............... *A61B 5/486* (2013.01); *A61B 5/112* (2013.01); *A61B 5/1124* (2013.01);
(Continued)

(58) Field of Classification Search
CPC ....... A61B 5/486; A61B 5/112; A61B 5/1124; A61B 5/1128; A61B 5/4836; A61B 5/389;
(Continued)

(56) References Cited

U.S. PATENT DOCUMENTS

| 6,644,976 B2 | 11/2003 | Kullok et al. |
| 6,719,690 B1 * | 4/2004 | Cassily ............... A61B 5/6896 434/258 |

(Continued)

FOREIGN PATENT DOCUMENTS

| CN | 102138781 | 8/2011 |
| CN | 102139140 | 8/2011 |

(Continued)

OTHER PUBLICATIONS

International Search Report and Written Opinion for International Application No. PCT/US2021/042606, dated Nov. 4, 2021, 13 pages.

(Continued)

*Primary Examiner* — Wesner Sajous
(74) *Attorney, Agent, or Firm* — Leason Ellis LLP

(57) ABSTRACT

A method and system for augmented neurologic rehabilitation (ANR) of a patient is disclosed. The ANR system generates rhythmic auditory stimulus (RAS) and a visual augmented reality (AR) scene that are synchronized according to a common beat tempo and output to the patient during a therapy session. Sensor worn by the patient capture biomechanical data relating to repetitive movements performed by the patient in sync with the AR visual content and RAS. A critical thinking algorithm analyzes the sensor data to determine a spatial and temporal relationship of the patient's movements relative to the visual and audio elements and determine a level of entrainment of the patient and progression toward clinical/therapeutic goals. Additionally, a 3D AR modelling module configures the processor to dynamically adjust the augmented-reality visual and audio content output to the patient based on the determined level of entrainment and whether a training goal has been achieved.

19 Claims, 42 Drawing Sheets

Related U.S. Application Data which is a continuation of application No. 15/488,201, filed on Apr. 14, 2017, now Pat. No. 10,448,888.

(60) Provisional application No. 63/054,599, filed on Jul. 21, 2020, provisional application No. 62/322,504, filed on Apr. 14, 2016.

(51) Int. Cl.
  *G06T 7/50* (2017.01)
  *G06T 15/20* (2011.01)
  *G06T 19/20* (2011.01)

(52) U.S. Cl.
  CPC ............ *A61B 5/4836* (2013.01); *A61B 5/002* (2013.01); *A61B 5/0077* (2013.01); *A61B 5/1128* (2013.01); *A61B 5/7264* (2013.01); *A61B 5/7275* (2013.01); *A61B 2562/0219* (2013.01)

(58) Field of Classification Search
  CPC ..... A61B 5/002; A61B 5/0077; A61B 5/7264; A61B 5/7275; A61B 2562/0219; A61B 34/20; A61B 34/10; A61B 90/36; A61B 2034/2057; A61B 2090/367; G06T 7/50; G06T 19/20; G06T 15/20; G06T 11/008; G06T 11/005; G06T 7/70; G06T 2207/10121; G06T 2207/10136; G06T 2207/10081

See application file for complete search history.

(56) References Cited

U.S. PATENT DOCUMENTS

| | | | |
|---|---|---|---|
| 7,825,319 | B2 | 11/2010 | Turner |
| 9,424,348 | B1 | 8/2016 | Riggs-Zeigen |
| 9,446,302 | B2 | 9/2016 | Gavish |
| 9,536,560 | B2 | 1/2017 | Jehan et al. |
| 10,448,888 | B2 * | 10/2019 | McCarthy ............ A61B 5/1124 |
| 11,786,163 | B2 * | 10/2023 | Garten ................... A61B 5/742 600/28 |
| 2002/0107556 | A1 | 8/2002 | Mcloul et al. |
| 2003/0068605 | A1 | 4/2003 | Kullok et al. |
| 2007/0074617 | A1 | 4/2007 | Vergo |
| 2007/0113726 | A1 | 5/2007 | Oliver et al. |
| 2008/0097633 | A1 | 4/2008 | Jochelson et al. |
| 2008/0153671 | A1 | 6/2008 | Ogg et al. |
| 2008/0191864 | A1 | 8/2008 | Wolfson |
| 2010/0075806 | A1 * | 3/2010 | Montgomery ....... G09B 19/003 600/23 |
| 2010/0186578 | A1 | 7/2010 | Bowen |
| 2010/0240945 | A1 | 9/2010 | Bikko |
| 2012/0101411 | A1 | 4/2012 | Hausdorff et al. |
| 2013/0060166 | A1 | 3/2013 | Friedman et al. |
| 2013/0231942 | A1 | 9/2013 | Capik |
| 2014/0206929 | A1 | 7/2014 | Anderson et al. |
| 2015/0093729 | A1 | 4/2015 | Plans et al. |
| 2016/0055420 | A1 | 2/2016 | Karanam et al. |
| 2016/0067136 | A1 | 3/2016 | Raghavan et al. |
| 2016/0235323 | A1 | 8/2016 | Tadi et al. |
| 2016/0292881 | A1 | 10/2016 | Bose et al. |
| 2016/0370854 | A1 | 12/2016 | Steele |
| 2017/0296116 | A1 * | 10/2017 | McCarthy ............ A61B 5/4836 |
| 2019/0287309 | A1 | 9/2019 | Samec et al. |
| 2020/0138363 | A1 | 5/2020 | McCarthy et al. |
| 2020/0286505 | A1 * | 9/2020 | Osborne ................. G06N 3/08 |
| 2021/0086024 | A1 * | 3/2021 | McCarthy ............. G16H 50/30 |

FOREIGN PATENT DOCUMENTS

| | | |
|---|---|---|
| CN | 204468592 | 7/2015 |
| CN | 105771087 | 7/2016 |
| EP | 1819309 | 8/2007 |
| JP | 2003267899 | 9/2003 |
| JP | 2006102156 | 4/2006 |
| JP | 2007193907 | 8/2007 |
| JP | 2015202140 | 11/2015 |
| WO | 2004099942 | 11/2004 |
| WO | 2006038712 | 4/2006 |
| WO | 2019023256 A1 | 1/2019 |
| WO | 2020100671 A1 | 5/2020 |

OTHER PUBLICATIONS

Viglialoro, et al. "Review of the Augmented Reality Systems for Shoulder Rehabilitation", Information, Apr. 26, 2019, 14 pgaes, https://www.mdpi.com/2078-2489/10/5/154.

International Search Report and Written Opinion for International Application No. PCT/US17/27742, dated Jul. 19, 2017; 8 pages.

European Search Report corresponding to European Patent Application No. 17783299.5, dated Nov. 11, 2019; 7 pages.

Japanese Office Action corresponding to Japanese Patent Application No. 2019-505329 dated May 18, 2021; 17 pages.

Tomotaka Ito, (Constructing a measuring and evaluating system for a gait of human lower limbs), Proceedings of the 2009 JSME Conference on Robotics and Mechatronics, The Japan Society of Mechanical Engineers, May 24, 2009, 1P1-K05(1)-1P1-K05(4).

Chinese Office Action corresponding to Chinese Patent Application No. 201780034526.3 dated Jan. 22, 2021; 16 pages.

European Search Report corresponding to European Patent Application No. 21845844.6, dated Jul. 19, 2024; 17 pages.

Japanese Office Action corresponding to Japanese Patent Application No. 2023-504242 dated Aug. 8, 2024; 7 pages.

Suteerawattananon, M. et al. "Effects of visual and auditory cues on gait in individuals with Parkinson's disease" Journal of Neurological Sciences, vol. 219, No. 1-2, Apr. 1, 2004, pp. 63-69.

* cited by examiner

SYSTEMS AND METHODS FOR AUGMENTED NEUROLOGIC REHABILITATION

CROSS-REFERENCE TO RELATED APPLICATIONS

This application is based on and claims benefit of and priority to U.S. Provisional Patent Application No. 63/054,599, titled "Systems and Methods for Augmented Neurologic Rehabilitation," to McCarthy et al., filed Jul. 21, 2020, and further is a continuation-in-part of U.S. patent application Ser. No. 16/569,388 for "Systems and Methods for Neurologic Rehabilitation," to McCarthy et al., which is a continuation of U.S. Pat. No. 10,448,888, titled, "Systems and Methods for Neurologic Rehabilitation," issue date Oct. 22, 2019, which is based on and claims priority to U.S. Provisional Patent Application No. 62/322,504 filed on Apr. 14, 2016, entitled "Systems and Methods for Neurologic Rehabilitation," which are each hereby incorporated by reference as if set forth in their respective entireties herein.

TECHNICAL FIELD

The present disclosure relates generally to systems and methods for rehabilitation of a user having a physical impairment by providing music therapy.

BACKGROUND

Many controlled studies over the past decade have emphasized the clinical role of music in neurologic rehabilitation. For example, regimented music therapy is known to directly enable cognition, motor and language enhancement. The process of listening to music enhances brain activity in many forms, igniting a widespread bilateral network of brain regions related to attention, semantic processing, memory, cognition, motor function and emotional processing.

Clinical data supports music therapy enhancing memory, attention, executive function, and mood. PET scan research on the neural mechanisms behind music revealed that pleasant music can stimulate a widespread network between the cortical and subcortical region including the ventral striatum, nucleus accumbens, amygdala, insula, hippocampus, hypothalamus, ventral tegmental area, anterior cingulate, orbitofrontal cortex, and ventral medial prefrontal cortex. The ventral tegmental area produces dopamine and has a direct connection to the amygdala, hippocampus, anterior cingulate and prefrontal cortex. This mesocorticolimbic system, which can be activated by music, plays a critical role in mediating arousal, emotion, reward, memory attention, and executive function.

Neuroscience research has revealed how the fundamental organization processes for memory formation in music shares a mechanism with the non-musical memory processes. The basis of phrase groupings, hierarchical abstractions, and musical patterns have direct parallels in temporal chunking principles for non-musical memory processes. This implies that memory processes activated with music could translate and enhance non-musical processes.

Accordingly, there remains a need for improved devices, systems, and methods for protecting the use of user identity and for securely providing personal information.

SUMMARY

In one aspect of the disclosed subject matter, a system for augmented neurologic rehabilitation of a patient is provided. The system comprises a computing system having a processor configured by software modules comprising machine-readable instructions stored in a non-transitory storage medium.

The software modules include an AA/AR modelling module that, when executed by the processor, configures the processor to generate an augmented-reality (AR) visual content and rhythmic auditory stimulus (RAS) for output to a patient during a therapy session. In particular, the RAS comprises beat signals output at a beat tempo and the AR visual content includes visual elements moving in a prescribed spatial and temporal sequence based on the beat tempo.

The system further comprises an input interface in communication with the processor for receiving real-time patient data including time-stamped biomechanical data of the patient relating to repetitive movements performed by the patient in time with the AR visual content and RAS. In particular, the biomechanical data is measured using a sensor associated with the patient.

The software modules further include a critical thinking algorithm (CTA) module that configures the processor to analyze the time-stamped biomechanical data to determine a temporal relationship of the patient's repetitive movements relative to the visual elements and beat signals output at the beat tempo to determine a level of entrainment relative to a target parameter. Moreover, the AA/AR modelling module further configures the processor to dynamically adjust the AR visual and RAS output to the patient in synchrony and based on the determined level of entrainment.

According to a further aspect, a method for augmented neurologic rehabilitation of a patient having a physical impairment is provided. The method is implemented on a computer system having a physical processor configured by machine-readable instructions which, when executed, perform the method.

The method includes the step of providing rhythmic auditory stimulus (RAS) for output to a patient via an audio output device during a therapy session. In particular, the RAS comprises beat signals output at a beat tempo.

The method also includes the step of generating augmented-reality (AR) visual content for output to a patient via an AR display device. In particular, the AR visual content includes visual elements moving in a prescribed spatial and temporal sequence based on the beat tempo and output in synchrony with the RAS. The method further includes the step of instructing, the patient to perform repetitive movements in time with the beat signals of the RAS and corresponding movement of the visual elements of the AR visual content.

The method further includes the step of receiving real-time patient data including time-stamped biomechanical data of the patient relating to repetitive movements performed by the patient in time with the AR visual content and RAS. In particular, the biomechanical data is measured using a sensor associated with the patient.

The method further includes the step of analyzing the time-stamped biomechanical data to determine a temporal relationship of the patient's repetitive movements relative to the visual elements and beat signals output according to the beat signal to determine an entrainment potential. Additionally, the method includes the steps of dynamically adjusting the AR visual content and RAS for output to the patient in synchrony and based on the determined entrainment potential not meeting a prescribed entrainment potential and continuing the therapy session using the adjusted AR visual content and RAS.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

The present invention relates generally to systems, methods and apparatus for implementing a dynamic closed-loop rehabilitation platform system that monitors and directs human behavior and functional changes. Such changes are in language, movement, and cognition that are temporally triggered by musical rhythm, harmony, melody, and force cues.

Figure 1:
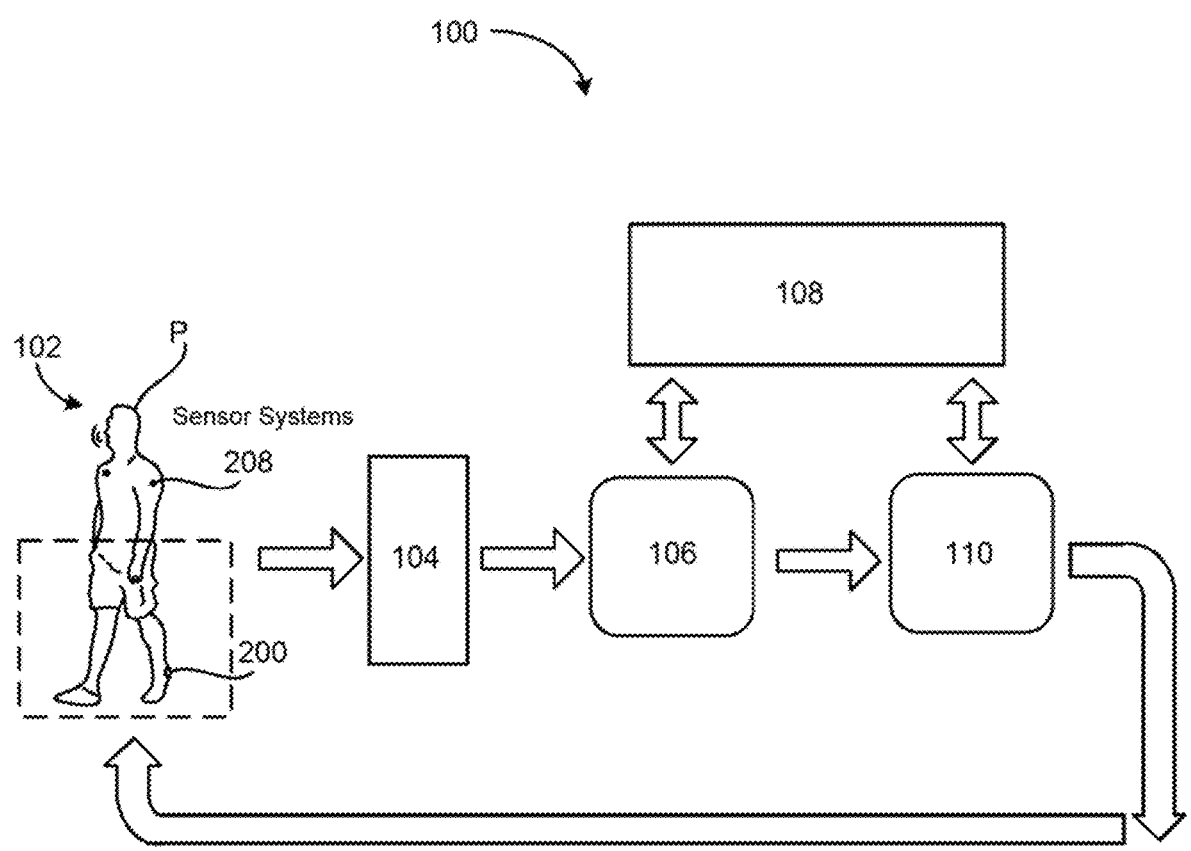
FIG. 1 is a diagram illustrating a system for therapy of a user by providing music therapy in accordance with exemplary embodiments of the disclosed subject matter.

In various embodiments of the invention, a dynamic closed-loop rehabilitation platform music therapy system 100 is provided illustrated in FIG. 1, which includes sensor components and systems 102, edge-processing components 104, collector components 106, analytics systems 108, and music therapy center 110. As will described in greater detail below, the sensor components, edge processing components, collector components machine learning processes and music therapy center may be provided on various hardware components. For example, in one embodiment, the sensor components and edge processing components may be located or worn by the patient. In such embodiments, the collector components and music therapy center may be provided on a handheld device. In such embodiments the analytics systems may be located on a remote server.

Sensor Systems

Throughout the description herein, the term "patient" is used to refer to the individual receiving musical therapy treatment. The term "therapist" is used to refer to the individual providing musical therapy treatment. In some embodiments, the patient is able to interact with this system described herein without the presence of the therapist to administer the treatment.

The sensor components 102 provide sensed biomechanical data about the patient. In some embodiments, the sensor components can include (1) wearable wireless real-time motion sensing devices or IMU (inertial measurement units), (2) wearable wireless real-time combination multiple zone foot plantar pressure/6-dimensional motion capture (IMU) devices, such as sensor 200, (3) wearable wireless real-time Electromyogram (EMG) devices, such as sensor 208 and (4) real-time wireless near infrared (NIR) video capture devices, such as imaging device 206 (See FIG. 4).

Figure 2:
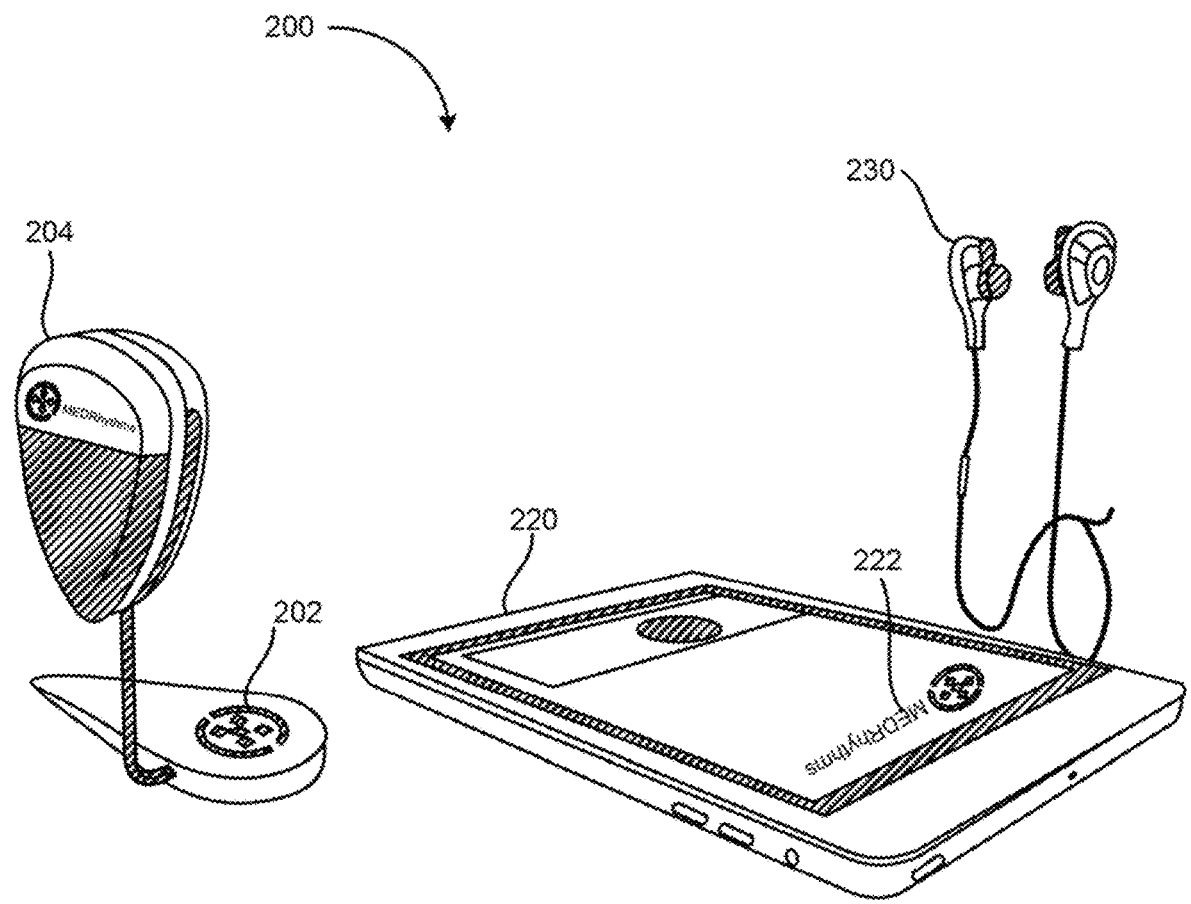
FIG. 2 is a diagram illustrating several components of a system for rehabilitation of a user by providing music therapy in accordance with exemplary embodiments of the disclosed subject matter.

As illustrated in FIG. 2, the systems and methods described herein are used in connection with treating walking disorders of the patient. Accordingly, the exemplary sensor 200 can be a combination multiple zone foot plantar pressure/6-degrees of freedom motion capture device. Sensor 200 records the patient's foot pressure and 6-degrees of freedom motion profile while the patient walks during a music therapy session. In some embodiments, the foot pressure/6-degrees of freedom motion capture device has variable recording duration intervals with a sampling rate of 100 Hz for a foot pressure profile that comprises 1 to 4 zones resulting in 100 to 400 pressure data points per foot per second.

The sensor 200 can include a foot pressure pad 202 having a heel pad (for measuring one zone of pressure, e.g., heel strike pressure) to a full insole pad (for measuring 4 zones of pressure). The pressure measurements are made by sensing the resistive changes in transducer material as a result of the compression due to the patient's weight transferred to the foot. These foot pressure maps are obtained for each sampling interval or at specific instants during a music therapy session.

The sensor 200 can include a 6-Dimensional motion capture device 204 that detects the changes in motion via a 6-degrees of freedom Micro-Electro-Mechanical Systems (MEMS) based sensor which determines linear acceleration in 3 dimensions, $A_x$, $A_y$, $A_z$ and rotational motion as pitch, yaw, and roll. Sampling at 100 Hz will produce 600 motion data points per second. These foot motion captures are obtained for each sampling interval or at specific instants during a music therapy session.

Figure 3:
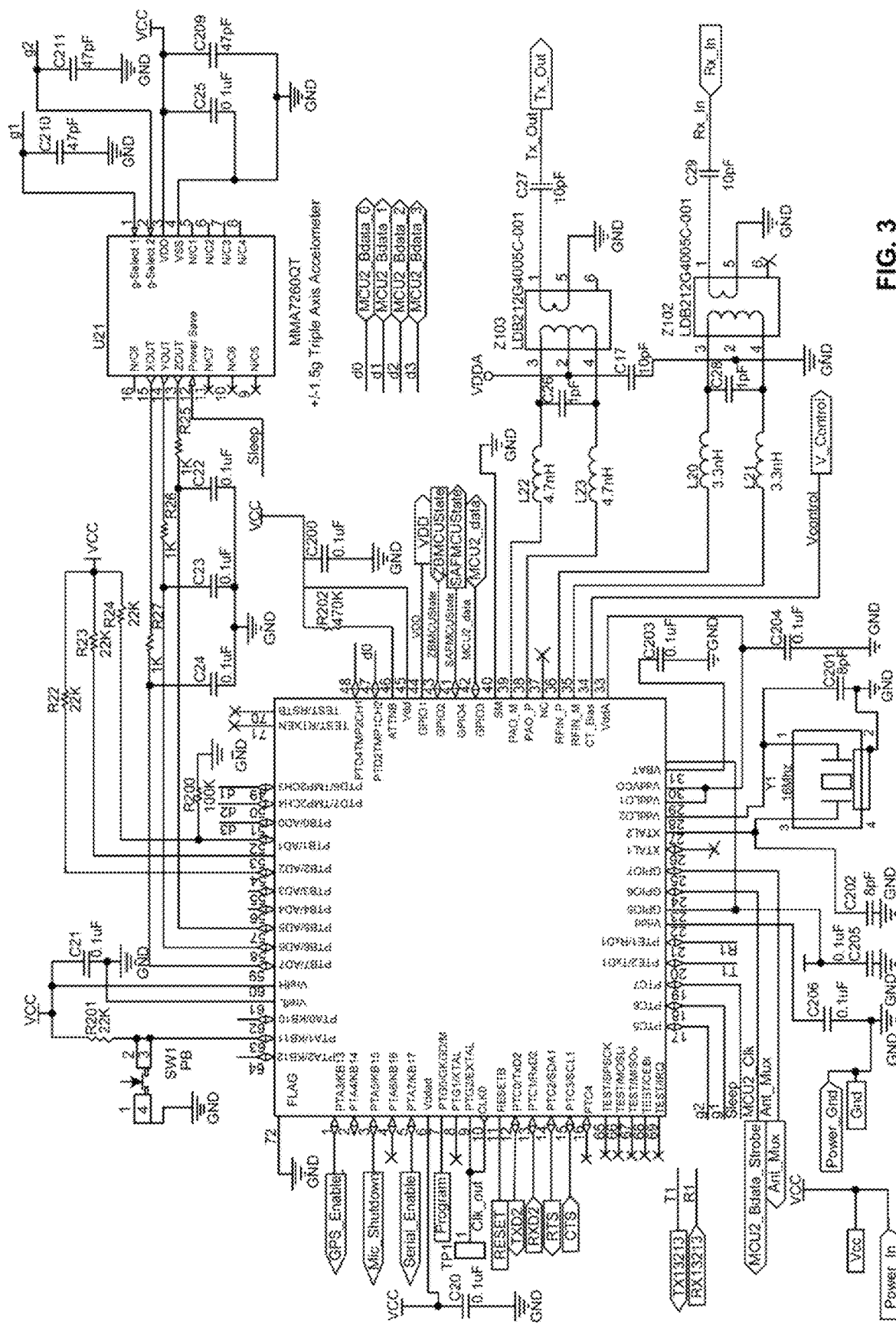
FIG. 3 is a schematic drawing of a sensor for measuring the biomechanical movements of a patient in accordance with exemplary embodiments of the disclosed subject matter.

The multiple zone pressure sensing with the 6-degrees of freedom motion capture device allows for map-able spatial and temporal gait dynamics tracking while walking. A schematic diagram of the sensor 200 is illustrated in FIG. 3.

Figure 4:
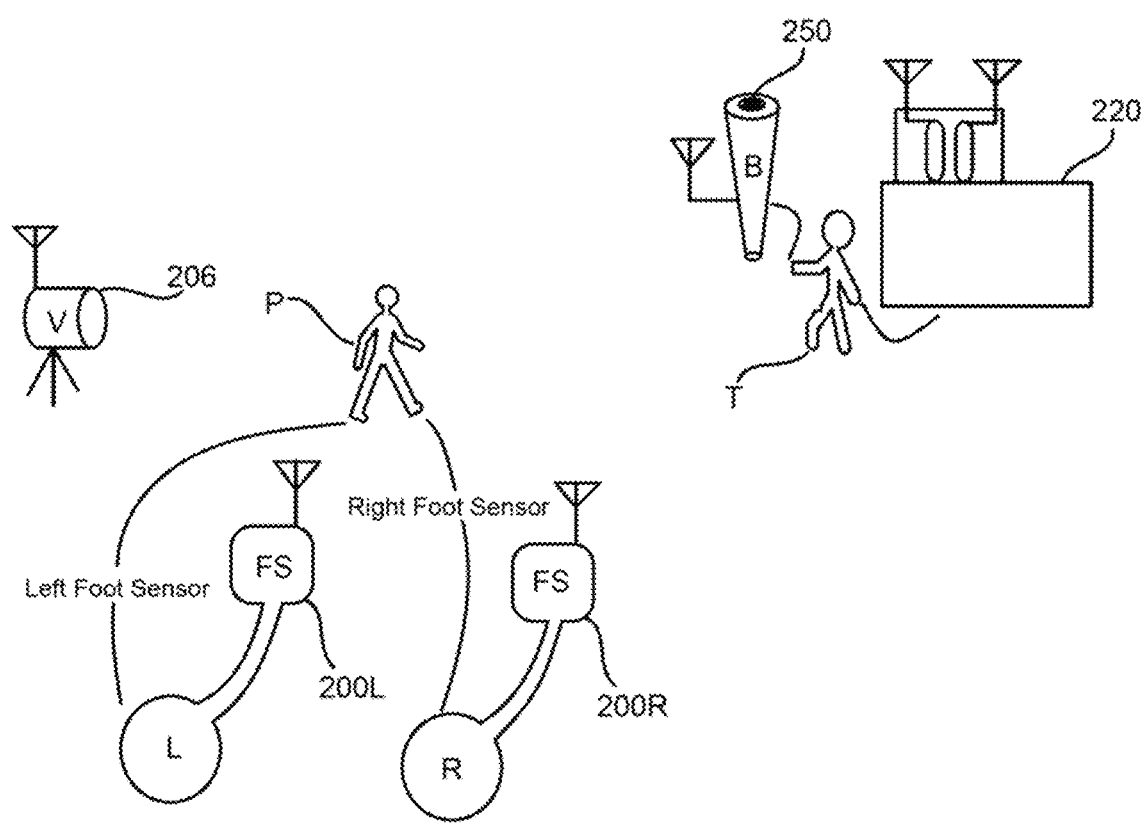
FIG. 4 is a diagram illustrating several components of the system in accordance with exemplary embodiments of the disclosed subject matter.

From a system perspective, as illustrated in FIG. 4, the patient P uses two foot sensors 200, one for each foot designated as Right 200R and Left 200L. In an exemplary embodiment, the right foot sensor 200R wirelessly communicates time-stamped internal measurement unit data and heel strike pressure data over a first channel, e.g., channel 5, in the IEEE 802.15.4 direct sequence spread spectrum (DSSS) RF band. The left foot sensor 200L wirelessly communicates time-stamped internal measurement unit data and heel strike pressure data over a second channel, e.g., channel 6, in the IEEE 802.15.4 direct sequence spread spectrum (DSSS) RF band. A tablet or laptop 220, optionally used by the therapist T, as described below, includes a wireless USB hub containing two IEEE 802.15.4 DSSS RF transceivers tuned to the first and second channels, e.g., channel 5 and 6, in order to capture the right/left foot sensor RF data. A handheld wireless trigger 250 is used to start and stop video and/or to make notations and index the time stream as discussed in greater detail below.

A video analytics domain can be used to extract patient semantic and event information about therapy sessions. Patient actions and interactions are components in the therapy that affect the therapy context and regiment. In some embodiments, one or more image capture devices 206, such as video cameras, (see FIG. 4) are used with a time-synched video feed. Any appropriate video may be incorporated into the system to capture patient movement; however, Near Infrared (NIR) video capture is useful to preserve the patient's privacy and to reduce the video data to be processed. The NIR video capture device captures NIR video images of a patient's body such as the position of the patient's torso and limbs. Further, it captures the patient's real-time dynamic gait characteristics as a function of a music therapy session. In some embodiments, the video is captured with a stationary camera, in which the background is subtracted to segment out foreground pixels.

As illustrated in FIG. 4, the one or more video cameras 206 are triggered by the tablet or laptop application when therapy session starts. The video cameras 206 can be stopped or started by a hand held wireless trigger unit 250 by the therapist. This allows for labeled time-stamped index to be created in the captured biomechanical sensor data and video data streams.

In some embodiments, wearable wireless real-time Electromyogram (EMG) devices 208 can be worn by the patient. EMG sensors provide the entire bi-ped profile for major muscle firing for locomotion. Such sensors provide data regarding the exact time when the muscle are fired.

Edge Processing

In some embodiments, the edge process is performed at the sensors 200, where sensor data is captured from the IMU and pressure sensors. This sensor data is filtered, grouped into various array sizes for further processing into frames reflecting extracted attributes and features, and where these frames are sent, e.g., wirelessly, to the collector 106 on a tablet or laptop. It is understood that the raw biomechanical sensor data obtained from the sensor 200 can alternatively be transferred to a remote processor for the collect for the edge processing functions to take place.

The wearable sensors 200, 208 and the video capture devices 206, generates sensor data streams that are processed holistically to facilitate biomechanical feature extraction and classification. Sensor fusion, combining the outputs from multiple sensors capturing a common event, better captures a result than any single constituent sensor inputs.

Capturing patient activities in the music therapy context formalizes the interactions as applied to the music therapy and in developing patient specific and generalized formal indicators of the music therapy performance and efficacy. Extracting video features and then analyzing allows for the capture of semantic, high-level information about patient behaviors.

In processing video, a learned background subtraction technique is used to create a background model which incorporates any variation in lighting conditions and occlusions in the physical area where music therapy occurs. The result of the background subtraction is a binary foreground map with an array of foreground blobs which are two dimensional contours. Thus, the video is sliced into individual image frames for future image processing and sensor fusion. Video information is provided with additional meta data by merging in the edge-processed sensor data from the IMU, foot pressure pad(s), and EMG sensors. The sensor data can be time synched with the other data using the RF trigger. Data can be sent directly to the collector, stored on the memory of the internal board, or analyzed on the edge running the OpenCV library.

The edge processor 104 can be a microprocessor, such as a 32-bit microprocessor incorporated into the foot pressure/6-degrees of freedom motion capture device that enables fast multiple zone scanning at a rate of 100 to 400 complete foot pressure/6-degrees of freedom motion profiles per second.

The foot pressure/6-degrees of freedom motion capture device collects foot pressure/6-degrees of freedom motion profile data for real-time gait analysis resulting in feature extraction and classification. In some embodiments, the foot pressure/6-degrees of freedom motion capture device initializes an micro controller unit (MCU), continuous operator process (COP), general purpose input output (GPIO), serial peripheral interface (SPI), interrupt request (IRQ), and sets a desired RF transceiver clock frequency by calling routines including micro controller unit initialize (MCUInit), general purpose input output initialize (GPIOInit), serial peripheral interface initialize (SPIInit), interrupt request acknowledge-initialize (IRQInit), interrupt request acknowledge (IRQACK), Serial Peripheral Interface Driver Read (SPIDrvRead), and IRQPinEnable. MCUInit is the master initialization routine which turns off the MCU watchdog and sets the timer module to use bus clock (BUSCLK) as a reference with a pre-scaling of 32.

The state variable gu8RTxMode is set to SYSTEM_RESET_MODE and the routines GPIOInit, SPIInit and IRQInit are called. The state variable gu8RTxMode is set to RF_TRANSCEIVER_RESET_MODE and the IRQFLAG is checked to see if IRQ is asserted. The RF transceiver interrupts are first cleared using SPIDrvRead, then the RF transceiver is checked for ATTN IRQ interrupts. Lastly, for MCUInit, calls are made to PLMEPhyReset to reset the physical MAC layer, IRQACK (to ACK the pending IRQ interrupt) and IRQPinEnable which is to pin, Enable, IE, and IRQ CLR, on signal's negative edge.

The foot pressure/6-degrees of freedom motion sensor 200 will wait for a response from the foot pressure/6-degrees of freedom motion collecting node, e.g., 250 milliseconds, to determine whether a default full foot pressure scan will be done or a mapped foot pressure scan will be initiated. In the case of a mapped foot pressure scan, the foot pressure/6-degrees of freedom motion collecting node will send the appropriate electrode the foot pressure scan mapping configuration data.

One aspect of the analytics pipeline is the feature set engineering process which will define those captured sensor values and their resulting sensor-fused values that are used to create feature vectors to define the input data structures for the analytics. Representative values are $Ax(i)$, $Ay(i)$, $Az(i)$, and $Ph(i)$, where i is the ith sample, where $Ax(i)$ is the acceleration in the x-direction which is Lateral in relation to the foot sensor; $Ay(i)$ is the acceleration in the y-direction which is Front in relation to the foot sensor; $Az(i)$ is the acceleration in the z-direction which is Up in relation to the foot sensor; and $Ph(i)$ is the heel strike pressure. The Sensor values are presented in Table 1:

TABLE 1

Avg (Ax) = Sum [Ax(i) over i = 0 to i = N]/N
Avg (Ax) = Sum [Ax(i) over i = 0 to i = N]/N
Avg (Ay) = Sum [Ay(i) over i = 0 to i = N]/N
Avg (Az) = Sum [Az(i) over i = 0 to i = N]/N
Max (Ax) in the range of Ax(i) from i = 0 to i = N
Max (Ay) in the range of Ay(i) from i = 0 to i = N
Max (Az) in the range of Az(i) from i = 0 to i = N
Min (Ax) in the range of Ax(i) from i = 0 to i = N
Min (Ay) in the range of Ay(i) from i = 0 to i = N
Min (Az) in the range of Az(i) from i = 0 to i = N
Avg (Ph) = Sum [Ph(i) over i = 0 to i = N]/N
Max (Ph) in the range of Ph(i) from i = 0 to i = N
where N = window size In some embodiments, the sensor-fused technique uses the heel strike pressure value $Ph(i)$ to "gate" the analysis of the following exemplary feature values to derive a window of data as will be described below. For example, the "onset" (start) can be determined based on heel pressure exceeding a threshold indicating heel strike, and the "stop" based on heel pressure falling below a threshold indicating heel off, presented in Table 2, below. It is understood, that heel strike pressure is one example of a parameter that can be used to for the "gate" analysis. In some embodiments, "gating" is determined by use of IMU sensor data, video data, and/or EMG data.

TABLE 2

Power Factor $PF(i) = \text{Sqrt}(Ax(i)^{}2 + Ay(i)^{}2 + Az(i)^{**}2)$
Windowed Total Motion Intensity = [Avg(Ax) + Avg(Ay) + Avg(Az)]/3
Windowed Lateral Tremor Intensity = Sum [ $(Ax(i) - Ax(i + 1))^{**}2$ ]
from i = 0 to i = N
Windowed Total Tremor Intensity =
Sum [ $(Ax(i) - Ax(i + 1))^{**}2$ ] +
Sum [ $(Ay(i) - Ay(i + 1))^{**}2$ ] +
Sum [ $(Az(i) - Az(i + 1))^{**}2$ ] from i = 0 to i = N
Windowed Differential Ax = Max (Ax) − Min (Ax)
Windowed Differential Ay = Max (Ay) − Min (Ay)
Windowed Differential Az = Max (Az) − Min (Az)
where N = window size Higher level feature values are calculated from the fused sensor values, such as exemplary values presented in Table 3:

TABLE 3

Step Count (Total number)
Step Length Right (centimeters-cm)

TABLE 3-continued

Step Length Left (cm)
Step Time Right (milliseconds-msec)
Step Time Left (msec)
Asymmetry Factor Right/Left Step Time (Step Time Right-Step Time Left)
Step Width (cm)
Cadence (strides per minute)
Stride Length (cm)
Stride Velocity (cm/sec)
Stride Time Right (msec)
Stride Time Left (msec)
Asymmetry Factor Right/Left Stride Time (Stride Time Right-Stride Time Left)
Stride Tremor (Windowed Lateral Tremor Intensity)
Stride Fluidity (Windowed Total Tremor Intensity)
Stride Tremor Accumulated (Windowed Lateral Tremor Intensity)
Stride Fluidity Accumulated (Windowed Total Tremor Intensity)
Swing Time Right Foot (msec)
Swing Time Left Foot (msec)
Stance Phase Right Foot (msec)
Stance Phase Left Foot (msec)
Asymmetry Factor Stance Phase Right/Left Stance Phase (Stance Phase Right-Stance Phase Left)
Double Support Stance Time (msec)
Vertical Displacement [Mid-Stance] Max (cm)
Vertical Displacement [Double Support] Min (cm)
Heel Strike Time Right Foot (msec)
Heel Strike Time Left Foot (msec)
Heel Strike Pressure Right Foot (shift N-Newton)
Heel Strike Pressure Left Foot (N)
Asymmetry Factor Right/Left Heel Strike Pressure (Heel Strike Pressure Right Foot-Heel Strike Pressure Left Foot)
Distance Travelled Accumulated (meters-m)
Average Velocity (m/min)
Variability of each of the factors The system described herein provides the capability to "gate" or provide a "window" with respect to the patient biomechanical data. Gating of the biomechanical data is useful for repetitive patient movements, such as the repetitive strides while a patient is walking. Sensor data, from one or more sources, such as pressure sensors, IMU sensors, video data, and EMG data, is used to identify cycles of movement that repeat over time. For example, when a patient walks, foot pressure increases and decreases repetitively, as the patient's foot contacts the ground and then is lifted off the ground. Likewise, the velocity of the foot increase as the foot moves forward and decreases to zero while the foot is planted on the ground. As a further example, the Y-position or height of the patient's foot cycles between a low position (on the ground) and a high position (approximately in mid stride). The "gating" technique identifies repeating cycles or "windows" within such data. In the case of a patient walking, the cycle is repeated with each step. Although there may be variations between cycles, e.g., between steps, certain patterns repeat with each cycle. Selecting an onset time (start time) of each cycle involves locating an identifiable point (maximum or minimum) of a biomechanical parameter. The selection of the parameter for the onset time is selected based upon the available data. Thus, in some embodiments, the moment when the heel-strike pressure exceeds a threshold may be used to demarcate the onset time of each cycle. (See, e.g., FIG. 5. Pressure 316a and 316b includes a cyclic characteristic. "Onset" may be determined at the moment the pressure exceeds a threshold.) Similarly, the onset time may be demarcated when foot velocity falls to zero.

In some embodiments, raw frames data is pre-processed, taking the instant data and "gating" it, e.g., identifying a window, and then analyzing data within that window to identify outliers and to perform analysis on the data, e.g., exponential analysis, averaging data among multiple windows. Fusion of sensor data, by including both IMU data and heel-strike pressure data, allows for more precise identification of onset times for a single stride or other repeated units of motion than using data from a single sensor. Sensor data captured within a single stride is considered a "window," and information extracted from this analysis includes, e.g., stride length, step count, cadence, time when step occurs, distance traveled, stance phase/swing phase, double support time, velocity, symmetry analysis (e.g., between left and right leg), outward swing, shuffling, power vector, lateral acceleration, step width, variability of each of these dimensions, additional parameters derived from the above-described information, etc. Feature extraction can be processed on microprocessor chip, e.g., a 32-bit chip. Capture of wireless synchronous-gated biomechanical sensor data and video data capture capability allows for time-series template creation.

The data can be indexed by the patient or the therapist during a music therapy session. The "gating" functionality described above is useful to tie exception conditions to particular strides or steps. For example, the therapist may observe a particular exception condition or behavior (such as an anomaly or incident) in the patient's movement. The indexing function allows the therapist to initiate, such as, capture to "record," an exception condition or behavior via a user interface on the handheld tablet or laptop, such as the wireless trigger unit 250 illustrated in FIG. 4, or voice control. A notation can be created that includes a timestamp and a comment, such as the occurrence of a "stumble" by the patient while walking. Such indexing facilitates time-series template creation. These time-series templates will be studied for review of therapy session events and for the development of times-series templates for training machine learning algorithms such as non-linear multi-layered perceptrons (NLMLP), convolutional neural networks (CNNs), and recurrent neural networks (RNNs) with long short term memory (LSTM).

In one embodiment, a communication protocol is provided to transfer sensor data from edge processing 104 (e.g. at the sensors 200) to the collector 106. See Table 4 below. In some embodiments, if the connection is idle for more than 100 ms, the RF has timed out.

TABLE 4

| [0 x 10] | Start of frame |
| [0 x 49] | FootClipSensor ID = 'I' |
| [0 x 52] or [0 x 4C] | Which FootClipSensor = 'R' or 'L' |
| [0 x 00~0 x FF] | Zone 1 |
| [0 x 00~0 x FF] | Zone 2 |
| [0 x 00~0 x FF] | Zone 3 |
| [0 x 00~0 x FF] | Zone 4 |
| [Az] | Az |
| [Ay] | Ay |
| [Ax] | Ax |
| [HighByteSeqNum] | High Byte Sequence |
| [LowByteSeqNum] | Low Byte Sequence |

In one embodiment, the foot pressure sensor zone scanning is performed by the FootScan routine where the FootDataBufferindex is initialized and the foot pressure sensor zone is activated by enabling MCU direction mode for output [PTCDD_PTCDDN=Output] and bringing the associated port line low [PTCD_PTCD6=0]. As the foot pressure sensor zone is activated based on the foot pressure sensor zone scanning map, the foot pressure sensor zones attached to the MCU analog signal ports will be sampled and then the current voltage reading converts them into digital form (which is the-time zone foot pressure).

Several variables such as FootDataBufferindex and IMUBufferIndex are used to prepare the IEEE 802.15.4 RF packets gsTxPacket.gau8TxDataBuffer[ ] which are for sending the data to be used in FootDataBuffer[ ] and IMUBuffer[ ]. The RF packets are sent using the RFSendRequest(&gsTxPacket) routine. This routine checks to see if gu8RTxMode is set at IDLE_MODE and uses gsTxPacket as a pointer to call the RAMDrvWriteTx routine which then calls SPIDrvRead to read the RF transceiver's TX packet length register contents. Using these contents, mask length settings update and then add 2 for CRC and 2 for code bytes.

SPISendChar is called to send a 0x7E byte, which is the 2nd code byte and then the SPIWaitTransferDone is called again to verify the send is done. With these code bytes sent, then the rest of the packet is sent using a for loop, where psTxPkt→u8DataLength+1 are the number of iterations to a series of sequential to SPISendChar, SPIWaitTransferDone, SPIClearRecieveDataReg. When complete, the RF transceiver is loaded with the packet to send. The ANTENNA_SWITCH is set to transmit, the LNA_ON mode enabled, and finally a RTXENAssert call made to actually send the packet.

Collector

The primary function of the collector 106 is to capture data from the edge processing 104, transfer data to and receive processed data from the analytics system 108, and transfer data to the music therapy center 110, described below. In some embodiments, the collector 106 provides control functionality, e.g., a user interface to login, configure the system, and interact with users, and includes a display unit to visualize/display data. The collector 106 may include lightweight analytics or machine learned algorithms for classification (e.g., lateral tremor, asymmetry, instability, etc).

The collector 106 receives body, motion, and localization data from the edge processor 104. Data received at collector 106 can be raw or processed at the edge 104 prior to transfer to the collector. For example, the collector 106 receives fused sensor data, subject to "windowing" and feature extraction. The transferred data can include two levels of data: (1) RF Packets sent from the Right/Left foot sensors as described in Table 1, (2) RF Packets from the Right/Left foot sensors which contains higher level attributes and features as described in Tables 2 and 3. The collector 106 locally stores the data. In some embodiments, the collector 106 classifies movement from the received data, e.g., comparing it to models stored locally (pre-downloaded from the analytics system) or sent to analytics system for classification. The collector may include a display unit to visualize/display the data.

In some embodiments the collector 106 operates on a local computer that includes a memory, a processor and a display. Exemplary devices on which the collector is installed can include augmented reality (AR) devices, virtual reality (VR) devices, tablets, mobile devices, laptop computers, desktop computers, and the like. FIG. 2 illustrates a handheld device 220 having a display 222, and which performs the collector functions. In some embodiments, the connection parameters for transferring data between the patient sensor and the collector are made include the use of Device Manager in Windows (e.g., Baud rate: 38400, data bits: 8; parity: none, stop bits: 1). In some embodiments, the collector 106 includes a processor that is held or worn by the music therapy patient. In some embodiments, the collector 106 includes a processor that is remote from the music therapy patient and carried by a therapist, and connected wirelessly or via a wired connection to the music therapy patient.

In one embodiment, a foot pressure/6-degrees of freedom motion collecting node captures RF transmitted data packets containing real-time foot pressure/6-degrees of freedom motion profile data from the foot pressure/6-degrees of freedom motion capture device. This is started by the foot pressure/6-degrees of freedom motion collecting node which creates a RF packet receive queue that is driven by a call back function on RF transceiver packet receive interrupts.

When an RF packet is received from a foot pressure/6-degrees of freedom motion capture device 200, a check is first made to determine if this from a new foot pressure/6-degrees of freedom motion capture device or an existing one. If this is from an existing foot pressure/6-degrees of freedom motion capture device, RF packet sequence numbers are checked to determine continuous synchronization before further analyzing the packet. If this is a foot pressure capturing/6-degrees of freedom motion device, a foot pressure/6-degrees of freedom motion capture device context state block is created and initialized. The context state block includes information, e.g., the foot pressure profile.

Above this RF packet session level process for node to node communication, is the analysis of the RF packet data payload. This payload contains the foot pressure profile based on the current variable pressure following the 6-degrees of freedom motion. This is structured as follows: |0x10|start|F1|F2⊕F3|F4|Ax|Ay|Az|Pi|Yi|Ri|XOR checksum|.

The IEEE 802.15.4 standard specifies a maximum packet size of 127 bytes and the Time Synchronized Mesh Protocol (TSMP) reserves 47 Bytes for operation, leaving 80 Bytes for payload. The IEEE 802.15.4 is compliant with the 2.4 GHz Industrial, Scientific, and Medical (ISM) band Radio Frequency (RF) transceiver.

The RF module contains a complete 802.15.4 Physical layer (PHY) modem designed for the IEEE 802.15.4 wireless standard which supports peer-to-peer, star, and mesh networking. It is combined with a MCU to create the required wireless RF data link and network. The IEEE 802.15.4 transceiver supports 250 kbps O-QPSK data in 5.0 MHz channels and full spread-spectrum encode and decode.

In some embodiments, control, reading of status, writing of data, and reading of data is done through the sensing system node device's RF transceiver interface port. The sensing system node device's MPU accesses the sensing system node device's RF transceiver through interface 'transactions' in which multiple bursts of byte-long data are transmitted on the interface bus. Each transaction is three or more bursts long, depending on the transaction type. Transactions are always read accesses or write accesses to register addresses. The associated data for any single register access is always 16 bits in length.

In some embodiments, control of the foot pressure/6-degrees of freedom motion collecting node's RF transceiver and data transfers are accomplished by means of a Serial Peripheral Interface (SPI). Although the normal SPI protocol is based on 8-bit transfers, the foot pressure/6-degrees of freedom motion collecting collector node's RF transceiver imposes a higher level transaction protocol that is based on multiple 8-bit transfers per transaction. A singular SPI read or write transaction consists of an 8-bit header transfer followed by two 8-bit data transfers.

The header denotes access type and register address. The following bytes are read or write data. The SPI also supports recursive 'data burst' transactions in which additional data transfers can occur. The recursive mode is primarily intended for Packet RAM access and fast configuration of the foot pressure/6-degrees of freedom motion collecting node's RF In some embodiments, all foot pressure sensor zones are sequentially scanned and the entire process repeats until a reset condition or inactivity power-down mode. The 6-degrees of freedom motion is captured by a serial UART interface to the Inertial Measurement Unit (IMU) from the MCU. The sampling rate for all sensing dimensions is 100-300 Hz which is Ax, Ay, Az, Pitch, Yaw, Roll and which sampled data is stored in IMUBuffer[ ].

A call is made to SPIDryWrite to update the TX packet length field. Next, a call to SPIClearRecieveStatReg is made to clear the status register followed by a call to SPIClearRecieveDataReg to clear the receive data register to make the SPI interface ready for reading or writing. With the SPI interface ready, a call is made to SPISendChar sending a 0xFF character which represents the 1st code byte and then SPIWaitTransferDone is called to verify the send is done.

Figure 5:
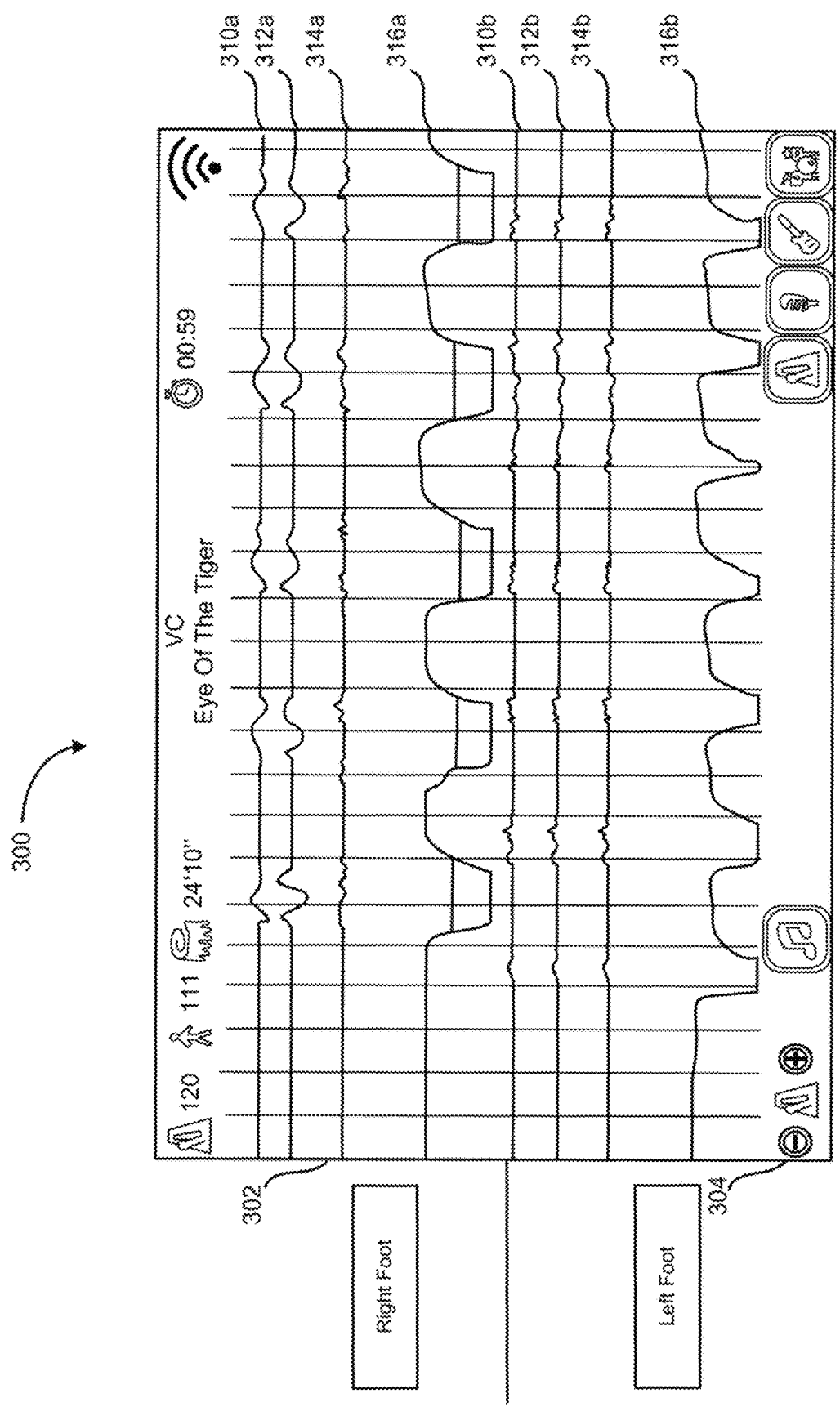
FIG. 5 illustrates an exemplary display of a component of a system for rehabilitation of a user by providing music therapy in accordance with exemplary embodiments of the disclosed subject matter.

FIG. 5 is an exemplary output 300 that may be provided on display 222 of the handheld device. For example, when therapy is provided for a patient's gait, the display output 300 may include a portion for the right foot 302 and a portion for the left foot 304. As a function of time, the display for the right foot includes accelerations $A_x$ 310a, $A_y$ 312a, and $A_z$ 314a, and foot pressure 316a. Similarly, the display for the left foot includes acceleration $A_x$ 310a, $A_y$ 312a, and $A_z$ 314a, and foot pressure 316a.

Classification is understood as the correlation of data, e.g., sensor fused data, feature data, or attribute data to real world events, e.g., activities or disposition of the patient. Typically, the classification is created and performed on the analytics system 108. In some embodiments, the collector 106 has a local copy of some 'templates.' Thus, the incoming sensor data and feature extracted data can be classified at the collector or the analytics system.

Context refers to the circumstances or facts that form the setting for an event, statement, situation, or idea. Context-aware algorithms examine the "who," "what," "when" and "where" related to the environment and time in which the algorithm is executed against certain data. Some context-aware actions include an identity, location, time, and activity being executed. In using contextual information to formulate a deterministic action, context interfaces occur among the patient, the environment, and the music therapy session.

The patient's reaction context to a music therapy session can involve a layer of algorithms that interpret the fused sensor data to infer higher-level information. These algorithms distill the patient reaction context. For example, a patient's bio-mechanical gait sequence is analyzed as it relates to a specific portion of the music therapy session. In one example, "lateral tremor" is the classifier of interest. Accordingly, it is determined that the patient's gait becomes more fluid with less lateral tremor.

Analytics Systems

The analytics systems 108, sometimes referred to as the back end system, store large models/archives and include machine learning/analytics processing, with the models described herein. In some embodiments, a web interface for login to view archived data, and a dashboard is also provided. In some embodiments the analytics system 108 is located on a remote server computer which receives data from the collector 106 running on a handheld unit such as handheld device or tablet 220. It is contemplated that the processing capability needed to perform the analytics and machine learning functions of the analytics system 108 may be also located on the handheld device 220.

Figure 6:
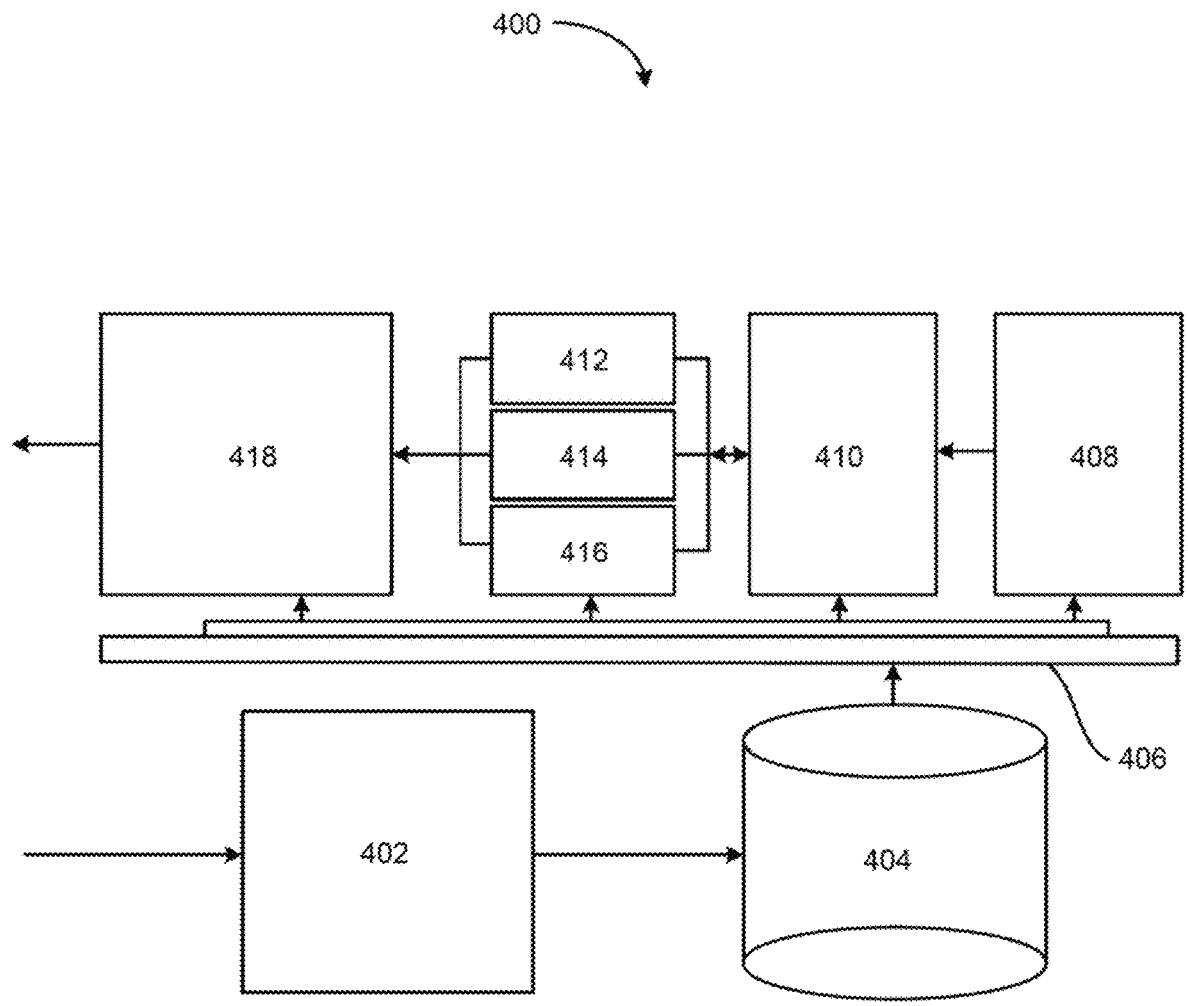
FIG. 6 is a flow diagram for one implementation of an analytics process in accordance with exemplary embodiments of the disclosed subject matter.

Data is transferred from the collector 106 to the analytics systems 108 for analytics processing. As illustrated in FIG. 6, the analytics processing 400 includes a user-interface 402 for receiving data from the collector 106. A database storage 404 receives incoming data from the collector 106 for storage. Training data as well as outputs of the analytics processing, e.g., the ensemble machine learning system 410, may also be stored on storage 404 to facilitate the creation and refinement of the predictive models and classifiers. A data bus 406 allows flow of data through the analytics processing. A training process 408 is performed on training data to derive one or more predictive models. An ensemble machine learning system 410 utilizes the predictive models. The output of the ensemble machine learning system 410 is an aggregation of these predictive models. This aggregated output is also used for classification requirements with template classifiers 412, such as tremor, symmetry, fluidity, or learned biomechanical parameters such as entrainment, initiation, etc. An API 418 connects to the collector and/or music therapy Center. Therapy algorithms 414 and predictive algorithms 416 include multi-layer perceptron neural networks, hidden Markov models, Radal based function networks, Bayesian inference models, etc.

An exemplary application of the systems and methods described herein is analysis of a patient's bio-mechanical gait. The gait sequence is feature-extracted into a series of characteristic features. The presence of these and other features in captured sensor-fused data inform the context detection algorithm if the patient's bio-mechanical gait sequence is valid. Bio-mechanical gait sequence capture requires robust context detection, which is then abstracted over a representative population of music therapy patients.

An example of such an activity is the location of a patient at an instance in time and their response to the music therapy at that time. The recognition and correlation of patient music therapy responses allows for recognition specific patterns of music therapy patient responses. Specific music therapy regimes are then benchmarked and analyzed for performance and efficacy by creating a baseline of music therapy patient responses and correlating them to future music therapy patient responses.

In combination with motion sensing, a distance metric with gait bio-mechanics capture is used to determine patient path trajectory using temporal and spatial variations/deviations between two or more music therapy sessions. From this sensor-fused data capture, features are extracted and classified to label various key patient therapy responses. Further sensor-fused data analysis uses histograms to allow for initial music therapy response pattern detection.

For music therapy session sensor fused data analysis, initially, patient specific Bayesian inference models are used utilizing Markov chains. The states of the chain represent the patient specific response patterns captured from music therapy baseline sessions. The inference is based on knowledge of the patient response pattern appearances at each sample interval and the temporal link to the previous state.

The prediction routine, a Multi-Layer Perceptron Neural Network (MLPNN), uses a directed graph node-based model having a top layer root-node which predicts requirements for reaching a subsequent node and obtaining a patient's sensor-fused data feature vector. This sensor fused data feature vector contains time-series processed motion data, music signature data, and video image data that is specifically significant for further processing. The directed graph, in this case, look like trees that are drawn upside down, where the leaves are at the bottom of the tree and the roots are the root-node. From each node, the routine can go to the left, where left is the left node on the next layer below the top layer which is where the root-node is located, selecting the left sub-node as the next observed node, or to the right where right is the right node on the next layer below the top layer where the root-node is located, and this based on the value of a certain variable whose index is stored in the observed node. If the value is less than the threshold, the routine goes to the left node and if greater, it goes to the right node. These regions, here, left & right, become the predictor spaces.

The model uses two types of input variables: ordered variables and categorical variables. An ordered variable is a value that is compared with a threshold that is also stored in a node. A categorical variable is a discrete value that is tested to see whether it belongs to a certain limited subset of values and stored in a node. This can be applied to various classifications. For example, mild, medium, and severe can be used to describe tremor and is an example of a categorical variable. Conversely, a fine grained range of values or a numerical scale, can be used to similarly describe tremor but in a numerical fashion.

If the categorical variable belongs to the limited set of values, the routine goes to the left node and if not, it goes to the right node. In each node, a pair of entities: variable_index, decision_rule (threshold/subset) are used to make this decision. This pair is called a split which splits on the variable: variable_index.

Once a node is reached, the value assigned to this node is used as the output of the prediction routine. The Multi-Layer Perceptron Neural Network is built recursively, starting from the root node. All training data, feature vectors, and responses, are used to split the root node, as described earlier; where the entities: variable_index, decision_rule (threshold/subset) segments the prediction regions. In each node the optimum decision rule on the best primary split is found based on gini "purity" criteria for classification and sum of squared errors for regression. The gini index is based on the measure of total variance across a set classes. The gini "purity" criteria referrers to a small gini index value, indicating that a node contains predominantly observations from a single class, which is the desired state.

Once the Multi-Layer Perceptron Neural Network is built, it may be pruned using a cross-validation routine. To avoid model over-fitting, some of the branches of the tree are cut off. This routine may be applied to standalone decisions. One salient property of the decision algorithm (MLPNN), described above, is an ability to compute the relative decisive power and importance of each variable.

The variable importance rating is used to determine the most frequent interaction type for a patient interaction feature vector. The pattern recognition starts with the definition of a decision space suitable to discriminate different categories of music therapy responses and music therapy events. A decision space can be represented by a graph with N dimensions, where N is the number of attributes or measurements considered to represent the music therapy responses and music therapy events. The N attributes compose a feature vector or signature which can be plotted in the graph. After sufficient samples have been inputted, the decision space reveals clusters of music therapy responses and music therapy events belonging to different categories which is used to associate new vectors to these clusters.

The dynamic closed-loop rehabilitation platform music therapy system utilizes several deep learning neural networks for learning and recalling patterns. In one embodiment, a non-linear decision space is built using the adaptive Radial Basis Function (RBF) model generator. New vectors can be calculated using the RBF model and/or with a K-Nearest Neighbor classifier. FIG. 6 illustrates the workflow of the machine learning sub-system of the dynamic closed-loop rehabilitation platform music therapy system.

Figure 7:
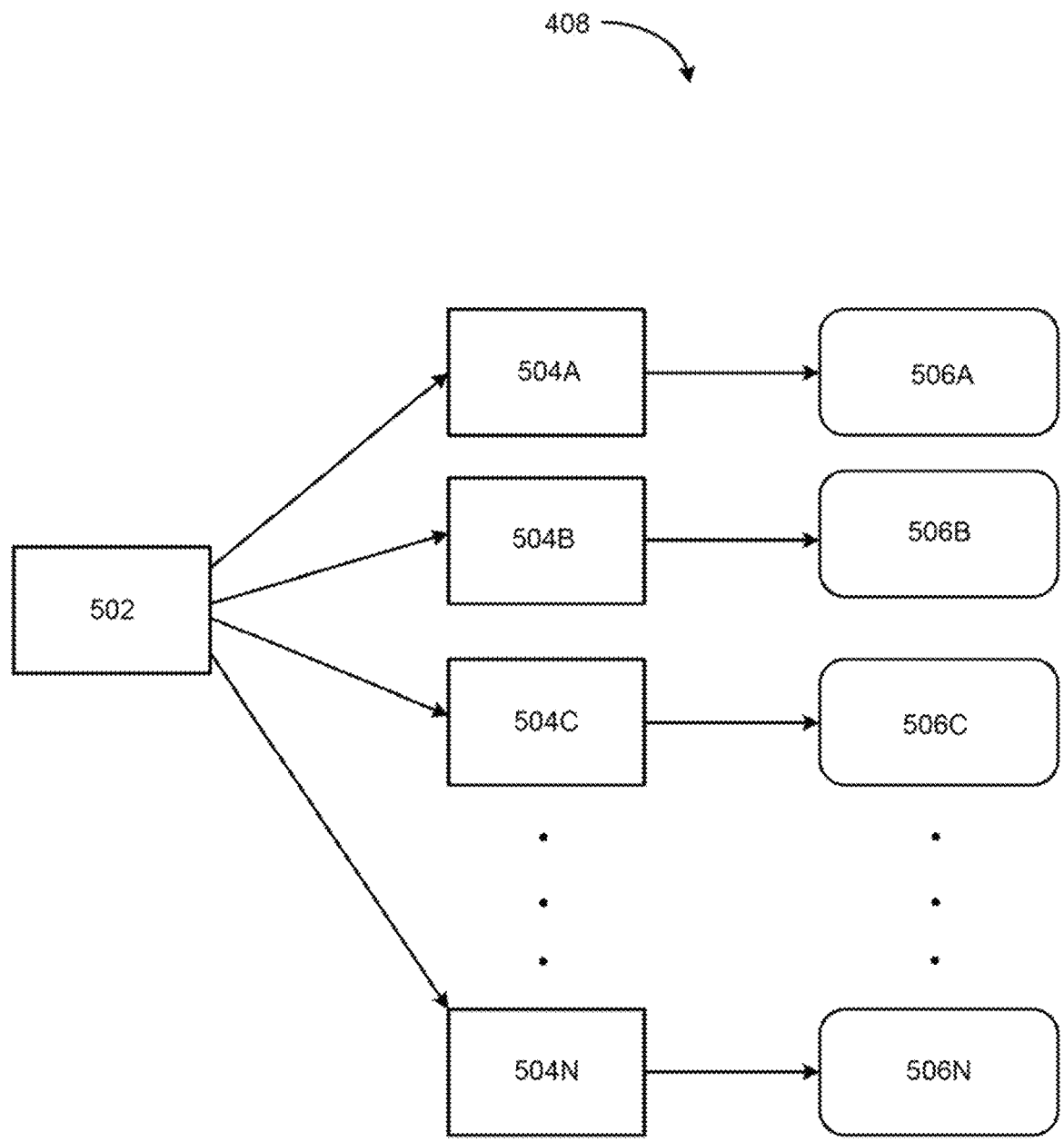
FIGS. 7-10 are flow diagrams for one implementation of a process in accordance with exemplary embodiments of the disclosed subject matter.

FIG. 7 illustrates the supervised training process 408, which includes a number of training samples 502, e.g., inputs would be features such as described in Table 3, above and example outputs will be items such as tremor, asymmetry, and power, the degree of these items, the prediction of changes, classification of how well the patient is recovering. It is understood new outputs are learned as a part of this process. This provides a base for higher levels of abstractions of the predictions and classifications as it is applied to different use cases (e.g. different disease states, combinations with pharmaceuticals, notifications to providers, fitness, and fall prevention). These training samples 502 are run with learning algorithms A1 504a, A2 504b, A3 504c . . . AN 504n to derive predictive models in M1 506a, M2 506b, M3 506c . . . MN 506n. Exemplary algorithms include Multi-Layer Perceptron Neural Networks, Hidden Markov Models, Radal Based Function Networks, Bayesian inference models.

Figure 8:
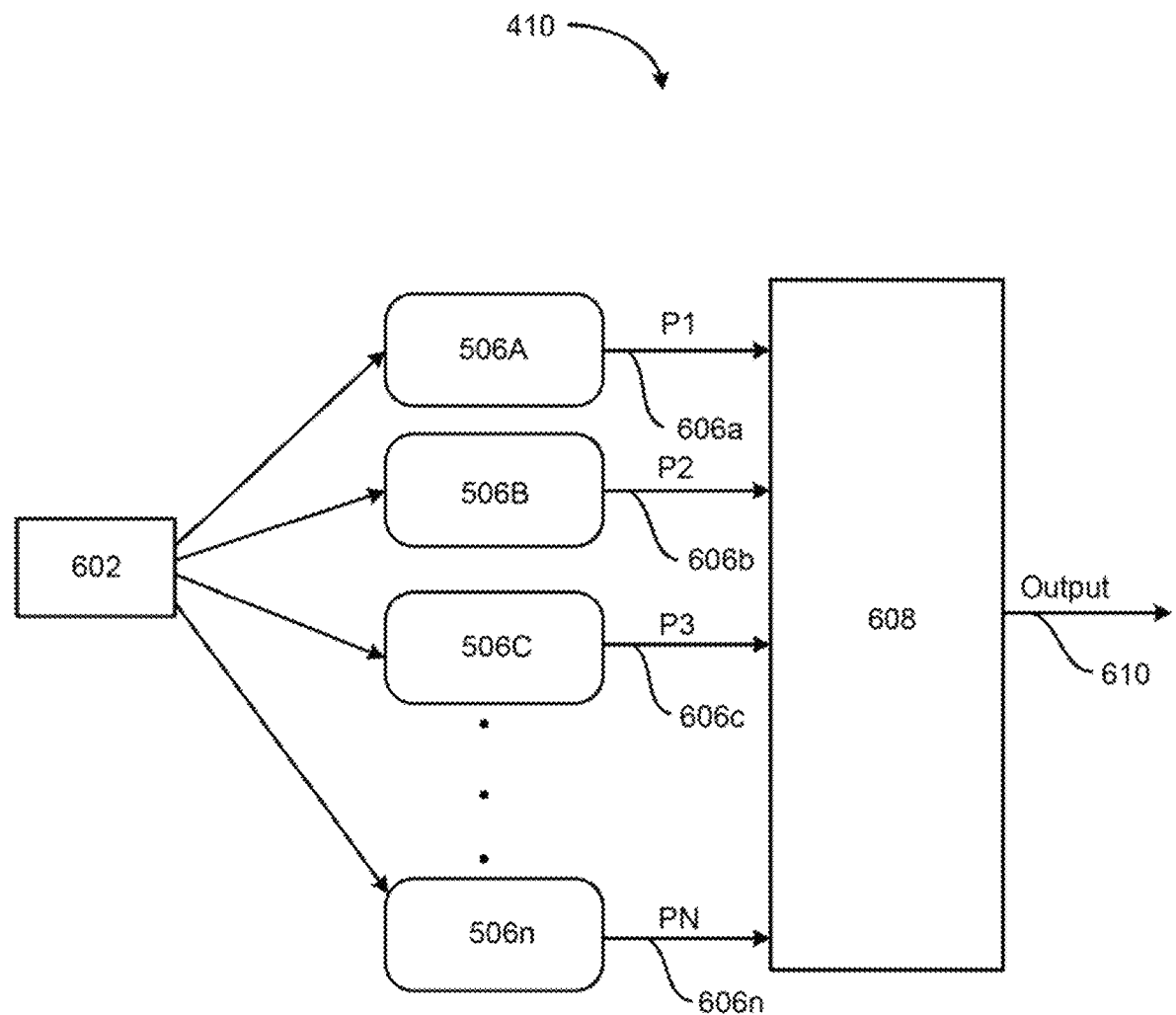

FIG. 8 illustrates the ensemble machine learning system 410, as an aggregation of the predictive models M1 506a, M2 506b, M3 506c . . . MN 506n on sample data 602 e.g., feature extracted data, to provide multiple predictive outcome data 606a, 606b, 606b . . . 606n. An aggregation layer 608, e.g., including decision rules and voting, is used to derive the output 610, given a plurality of predictive models.

The MR ConvNet system has two layers, where the first layer is a convolutional layer with mean pooling support. The MR ConvNet system second layer is a fully connected layer that supports multinomial logistic regression. Multinomial logistic regression, also called Softmax, is a generalization of logistic regression for handling multiple classes. In the case of logistic regression, the labels are binary.

Figure 9:
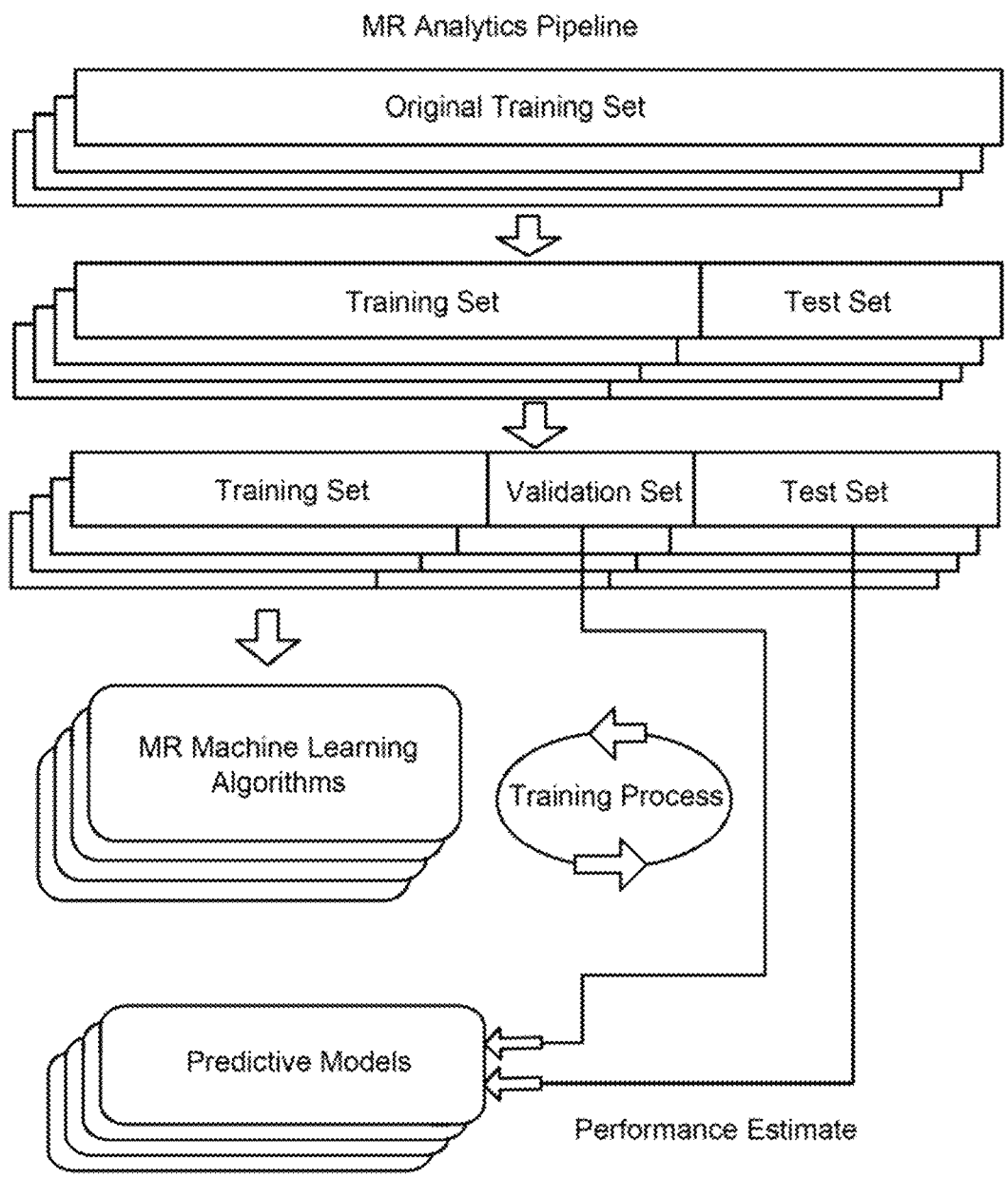

Softmax is a model that is used to predict the probabilities of the different possible outputs. The following assumes a multiclass classifier with m discrete classes via a Softmax final output layer:

$$Y1 = \text{Softmax}(W11*X1 + W12*X2 + W13*X3 + B1) \quad [1]$$

$$Y2 = \text{Softmax}(W21*X1 + W22*X2 + W23*X3 + B2) \quad [2]$$

$$Y3 = \text{Softmax}(W31*X1 + W32*X2 + W33*X3 + B3) \quad [3]$$

$$Ym = \text{Softmax}(Wm1*X1 + Wm2*X2 + Wm3*X3 + Bm) \quad [4]$$

$$\text{In general: } Y = \text{softmax}(W*X + B) \quad [5]$$

$$\text{Softmax}(X)i = \exp(Xi)/\text{Sum of } \exp(Xj) \text{ from } j=1 \text{ thru } N \quad [6]$$

Where Y=Classifier output; X=Sample input (all scaled (normalized) feature values); W=Weight Matrix. The classifications will, for example, score asymmetry, such as "Moderate Asymmetry score 6 out of 10 (10 high level of asymmetry to 0 for no asymmetry)" or gait fluidity "Gait Fluidity score 8 out of 10 Normal", etc. The Analytics pipelines is illustrated in FIG. 9.

Softmax regression allows for handling multiple classes beyond two. For logistic regression: P(x)=1/(1+exp (−Wx)) where W contains the model parameters that were trained to minimize a cost function. Also, x is the input features vector and $$((x(1),y(1)), \ldots ,(x(i),y(i)))) \quad [7]$$

would represent the training set. For multi-class classification, Softmax regression is used where y can take on N different values representing the classes instead of 1 and 0 in the binary case. So for the training set ((x(1), y(1)), . . . ,(x(i), y(i))), y(n) can be any value in the range of 1 through N classes.

Next, p(y=N|x;W) is the probability for each value of i=1, . . . , N. The following mathematically illustrates the Softmax regression process:

$$Y(x)=(p(y=1|x;W),p(y=2|x;W), \ldots p(y=N|x;W)) \quad [8]$$

Where Y(x) is the answer to the hypothesis, that given the input x, output the probability distribution across all classes such that their normalized sum is 1.

The MR ConvNet system convolves every windowed biomechanical data frames, as a vector, with every biomechanical template filter, as a vector, and then generates the responses using a mean pool function which averages the feature responses. The convolution process computes Wx while adding any biases and then passes this to a logistic regression (sigmoid) function.

Next, in the MR ConvNet system's second layer, the sub-sampled biomechanical template filter responses are moved into a two dimensional matrix where each column represents the windowed biomechanical data frames as a vector. The Softmax regression activation process is now initiated using:

$$Y(x)=(1/(\exp(Wx)+\exp(Wx)+ \ldots +\exp(Wx))^*(\exp(Wx),\exp(Wx), \ldots ,(\exp(Wx)) \quad [9]$$

The MR ConvNet system is trained with an optimization algorithm, gradient descent where a cost function J(W) is define and will be minimized:

$$J(W)=1/j^*((H(t(j=1),p(y=1|x;W)+H(t(j=2),p(y=2|x;W)+ \ldots +H(t(j),p(y=N|x;W)) \quad [10]$$

Where t(j) are the target classes. This averages all cross-entropies over the j training samples. The cross-entropy function is:

$$H(t(j),p(y=N|x;W)=-t(j=1)^*\log(p(y=1|x;W))+ \\ t(j=2)^*\log(p(y=2|x;W))+ \ldots +t(j)^*p(y=N|x;W) \quad [11]$$

Figure 10:
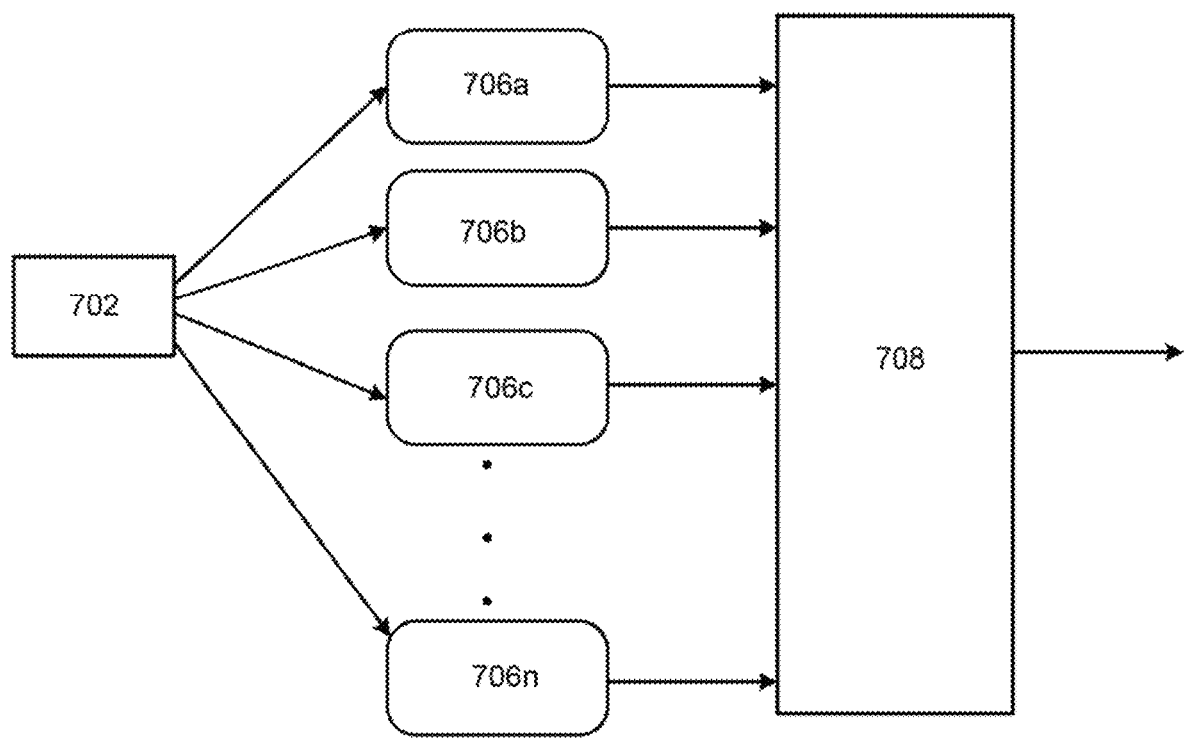

In FIG. 10, the ensemble machine learning system 408 includes a plurality of predictive models, e.g., Template Series 1 (tremor) 706a, Template Series 2, (symmetry) 706b, Template Series 3 (fluidity) 706c . . . additional templates (other learned biomechanical parameters, e.g., entrainment, initiation, etc.) 706n which are applied to conditioned inputs 702, e.g., for example, it could be the following: stride length for right and left features (x1, x2), variance of stride length right and left features (x3, x4), cadence right and left features (x6, x7), variance of cadence right and left features (x8, x9) etc. . . . this is where sample (x1, x2, . . . xn) are referred to as the Vector X which is input to 702 an ensemble of ML algorithms. These are conditioned referencing normalized and/or scaled inputs]. The aggregation classifier 708 outputs such information as tremor scale, symmetry scale, fluidity scale, etc.

Music Therapy Center

The music therapy center 110 is the decision making system that runs on processor, such as handheld device or laptop computer 220 of FIG. 2. The music therapy center 110 takes the inputs from the feature-in extracted sensor data at the collector 106, compares them to the defined process for the delivering of the therapy, and then delivers content of auditory stimuli that is played through music delivery system 230.

Embodiments of the invention use contextual information to determine why a situation is happening, then encodes observed actions, which causes a dynamic and modulated change in the system-state, and thus the music therapy session, in a closed-loop manner.

The interactions between the patient and music therapy session provide real-time data for determining music therapy patient context awareness, including motion, posture, strides, and gait reaction. After input data is collected by the sensing nodes (at the sensors), embedded nodes process the context-aware data (at edge processing), and provide immediate dynamic action and/or transmit the data to the analytics systems 108, e.g., an elastic network-based processing cloud environment for storage and further processing and analysis.

Based on inputs, the program will take any existing song content, alter the cadence, major/minor chords, meter and musical cues (e.g., melodic, harmonic, rhythmic and force cues). The system can overlay a metronome on existing songs. The song content can be beat mapped (e.g., if W in response to AV or MP3 file) or in MIDI format so that the precise knowledge of when the beat occurs can be used to calculate the entrainment potential. The sensors on the patient can be configured to provide haptic/vibration feedback pulsing at the music content.

EXAMPLES

Figure 11:
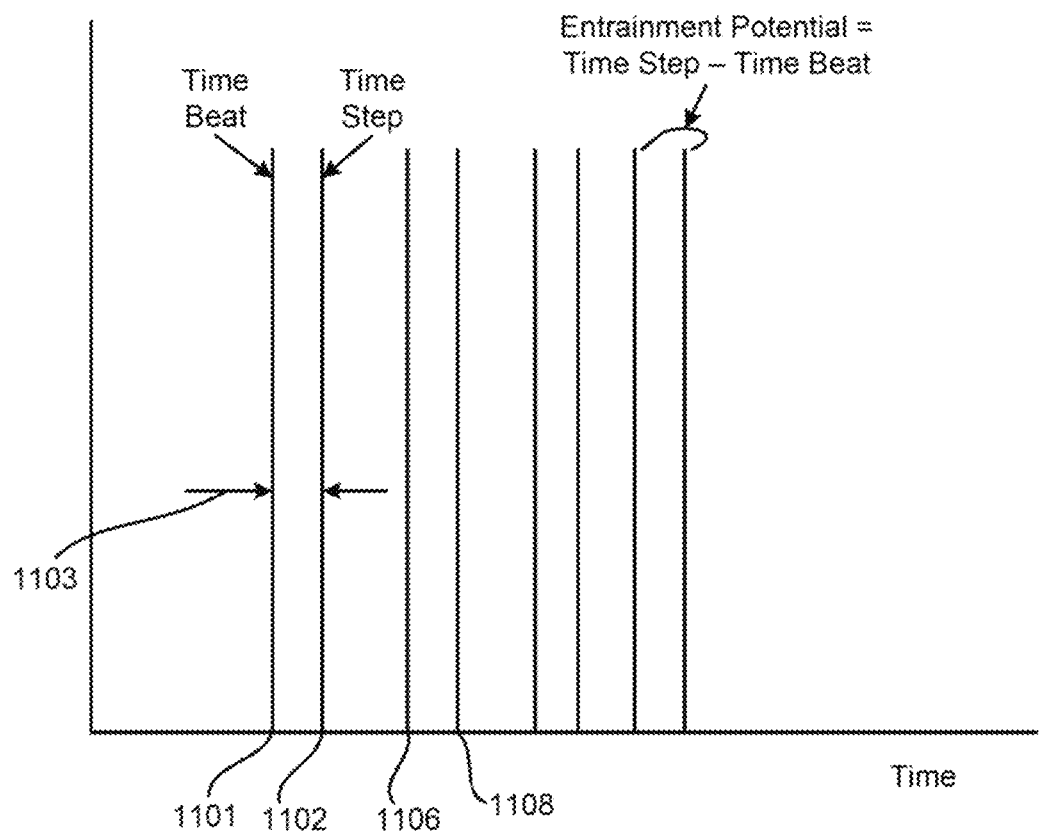
FIG. 11 is a time plot illustrating music and physical movement of the patient in accordance with exemplary embodiments of the disclosed subject matter.

An exemplary application of the method is described herein. Gait training analyzes the real-time relationship between the beats of the music being played for the patient and the individual steps taken by the patient in response to those particular beats of music. As discussed above, gating analysis is used to determine a window of data that repeats, with some variation, with each step or repetitive movement. In some embodiments, the beginning of the window is determined as the time when the heel strike pressure exceeds a threshold (or other sensor parameter.) FIG. 11 is an exemplary time plot illustrating the beats of music, "time beats," and the steps taken by the patient, "time step." Thus the onset time in this case is associated with the "time step." In particular, the plot illustrates a time beat 1101 of the music at time Time Beat 1. After a duration of time, the patient takes a step in response to time beat 1001, i.e., time step 1102, at time Time Step 1. The entrainment potential 1103 represents the delay (if any) between Time Beat 1 and Time Step 1.

Figure 12:
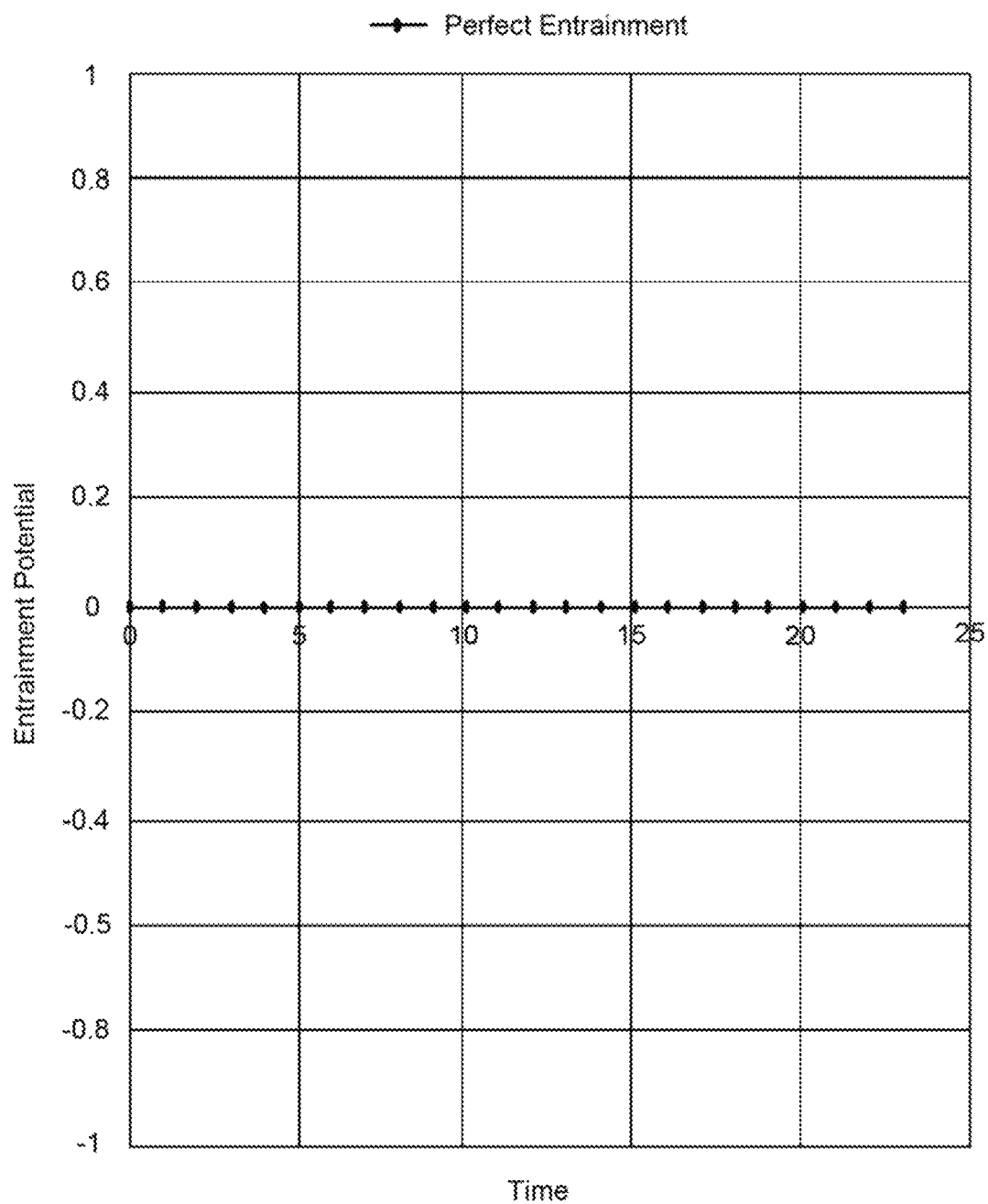
FIGS. 12-13 illustrate a patient response in accordance with exemplary embodiments of the disclosed subject matter.
Figure 13:
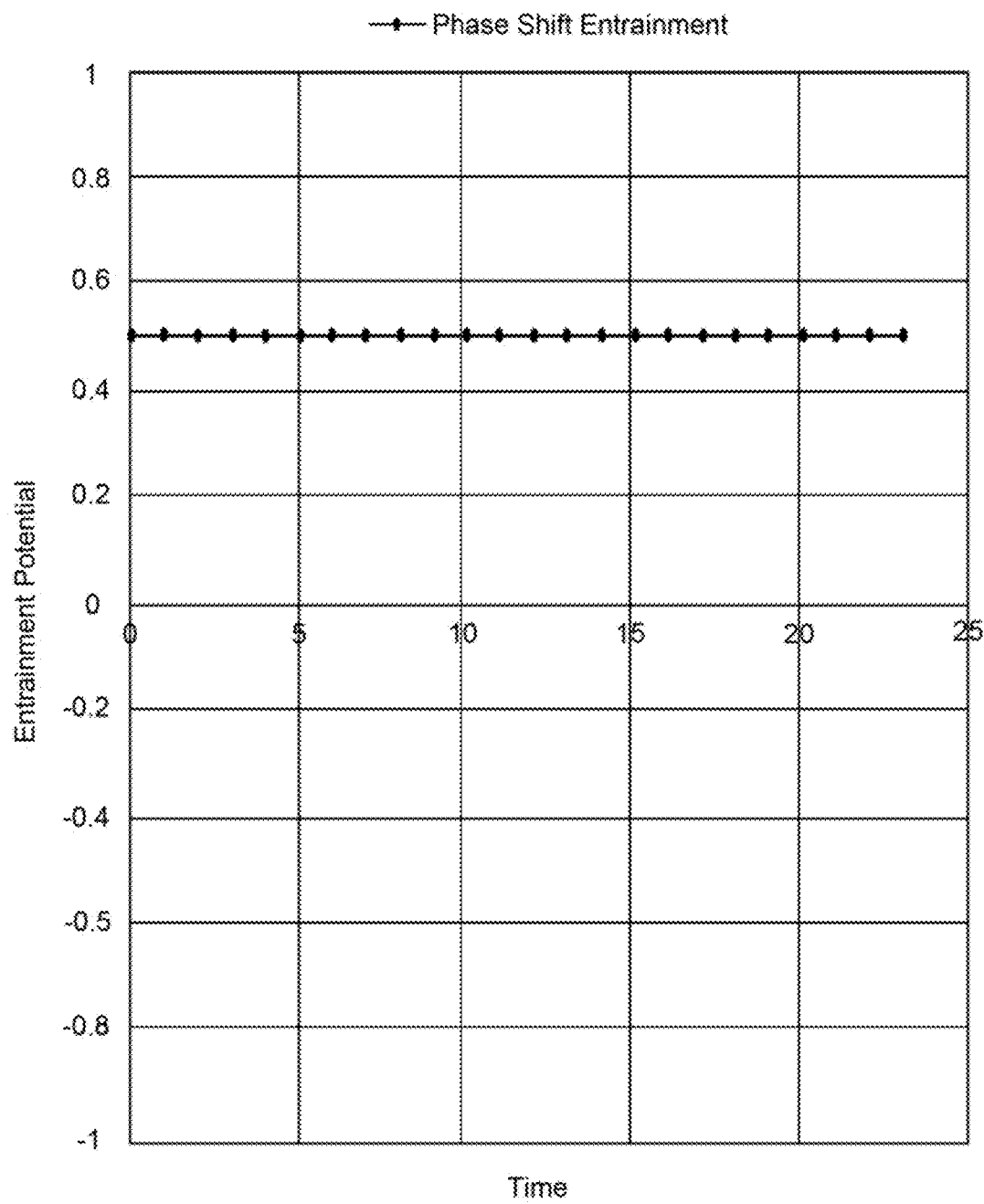

FIGS. 12-13 illustrate examples of entrainment of a patient's gait by use of the system described herein. FIG. 12 illustrates a "perfect" entrainment, e.g., a constant entrainment potential of zero. This occurs when there is no delay, or negligible delay, between the time beat and the associated time step taken in response to the time beat. FIG. 13 illustrates a phase-shift entrainment, e.g., a condition in which the entrainment potential is non-zero, but remains constant, or with minimal variation, over time. This occurs when there is a consistent delay, within tolerances, between the time beat and the time step over time.

With continued reference to FIG. 11, an EP Ratio is calculated as a ratio of the time duration between time beats to the time duration between time steps:

$$EP\ Ratio = \frac{Time\ Beat\ 2 - Time\ Beat\ 1}{Time\ Step\ 2 - Time\ Step\ 1} \quad [6]$$

Where Time Beat 1 1101 corresponds to the time of a first music beat, and Time Step 1 1102 corresponds to the time of the patient's step in response to Time Beat 1. Time Beat 2 1106 corresponds to the time of a second music beat, and Time Step 2 1108 corresponds to the time of the patient's step in response to Time Beat 2. The goal is for an EP Ratio=1 or EP Ratio/Factor=1. The Factor is determined as follows:

$$2^{round\left(log2\left(\frac{Time\ Step\ 2 - Time\ Step\ 1}{Time\ Beat\ 2 - Time\ Beat\ 1}\right)\right)} = Factor \quad [7]$$

Figure 14:
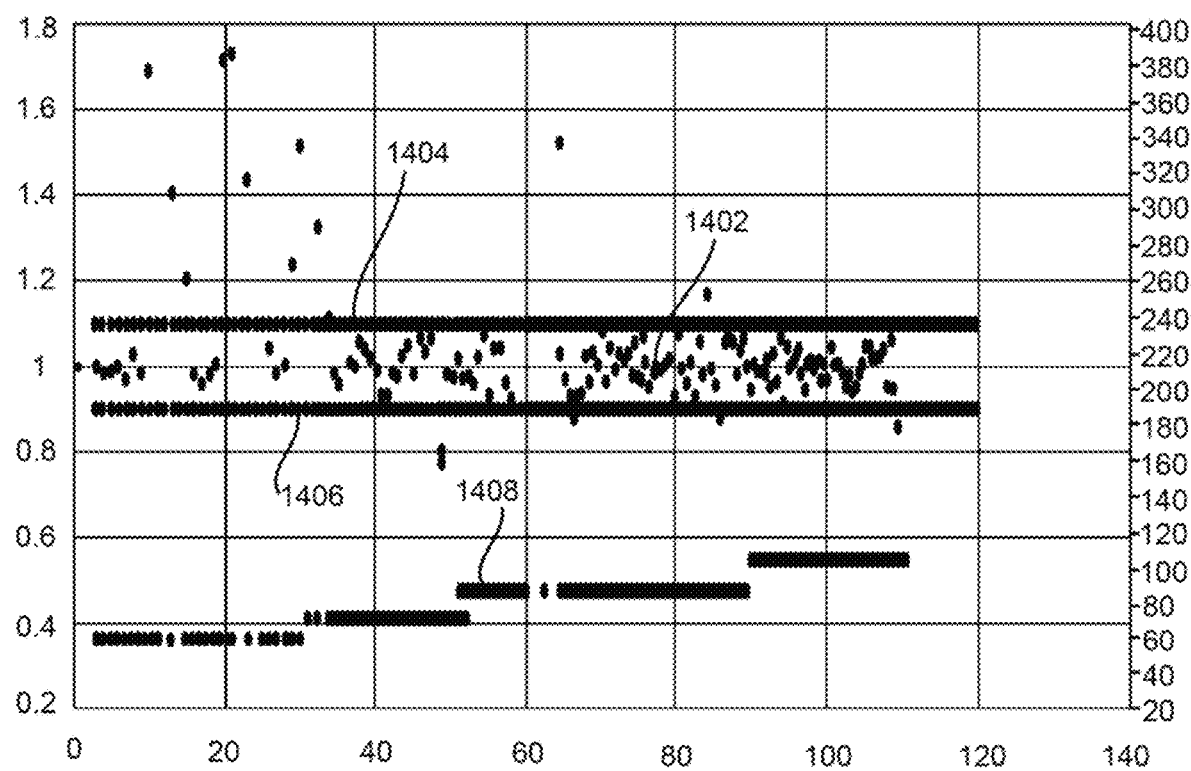
FIGS. 14-15 illustrate a patient response in accordance with exemplary embodiments of the disclosed subject matter.
Figure 15:
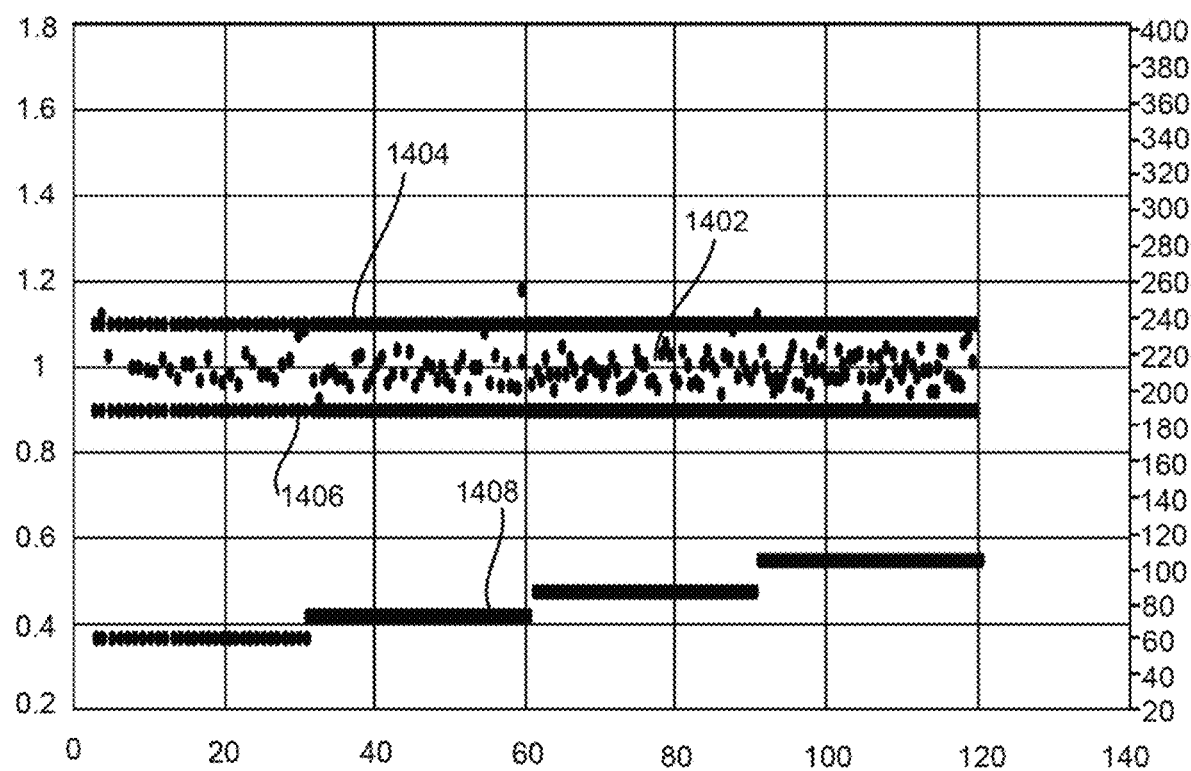

This factor allows the subdivision of beats to happen or for someone to step every 3 beats or 3 out of every 4. It can provide flexibility for different scenarios FIGS. 14 and 15 illustrate the entrainment response over time of a patient using techniques described herein. FIG. 14 (Left Y-axis: EP Ratio; Right Y-axis: Beats Per Minute; X-axis: time) illustrates a scattering of dots 1402 which represent the averages of the EP Ratio of a first patient's gait. The graph illustrates an upper limit 1404 of +0.1 and a lower limit 1406 of −0.1. The lines 1408 illustrate the tempo over time (starting at 60 beats per minute), increasing in steps to 100 bpm). FIG. 14 illustrates that the EP Ratio remains near 1 (±0.1) as the tempo is increased from 60 bpm to 100 bpm. FIG. 15 illustrates the EP ratio of a second patient's gait, in which the EP Ratio also remains near 1 (±0.1) as the tempo is increased from 60 bpm to 100 bpm.

Figure 16:
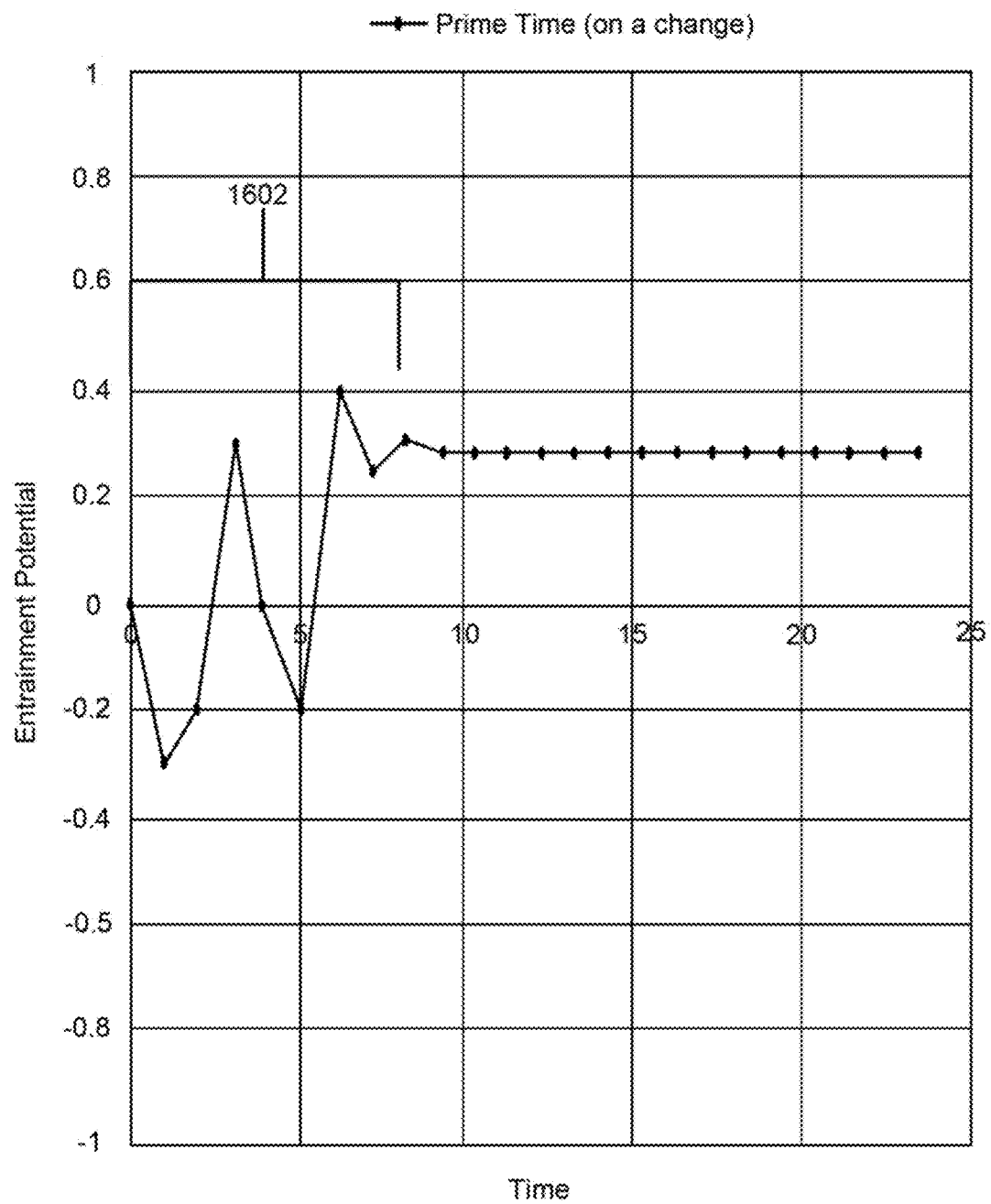
FIGS. 16-17 illustrate a patient response in accordance with exemplary embodiments of the disclosed subject matter.
Figure 17:
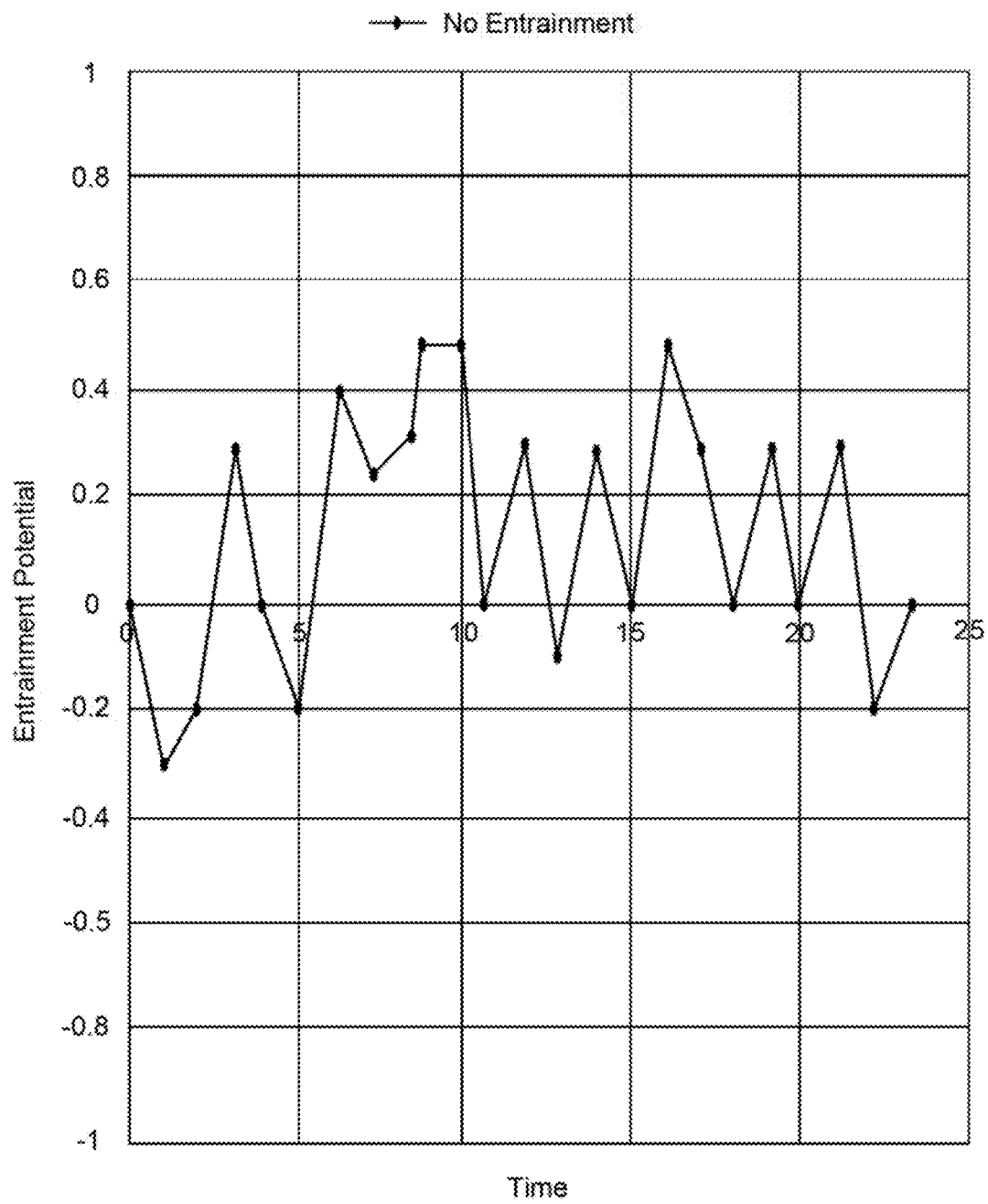

FIGS. 16 and 17 (Y-axis: Entrainment potential, X-axis: Time) illustrate two patients' responses to a change in the time beats (e.g., change in tempo) and/or change to the chords, change in haptic feedback, change in cueing of the feet (e.g., left-right, or left-right-cane cueing), etc. FIG. 16 shows a time based plot in which the patient's gait equilibrates with "perfect entrainment" (constant zero or negligible entrainment potential), or a constant phase-shifted entrainment potential. As illustrated in the figure, it takes a certain period of time, prime time 1602, until equilibration occurs. FIG. 17 illustrates a time-based plot in which the patient's gait does not equilibrate, e.g., does not reach perfect entrainment or a constant phase-shifted entrainment potential after a change to the time beats. Prime time is useful because it represents a set of data that is separate from measuring the accuracy of entrainment. The prime time parameter can also be used to screen future songs for suitability. For example, when patients exhibit a longer prime time value when a music piece is used, such music piece is less capable for therapy.

Figure 18:
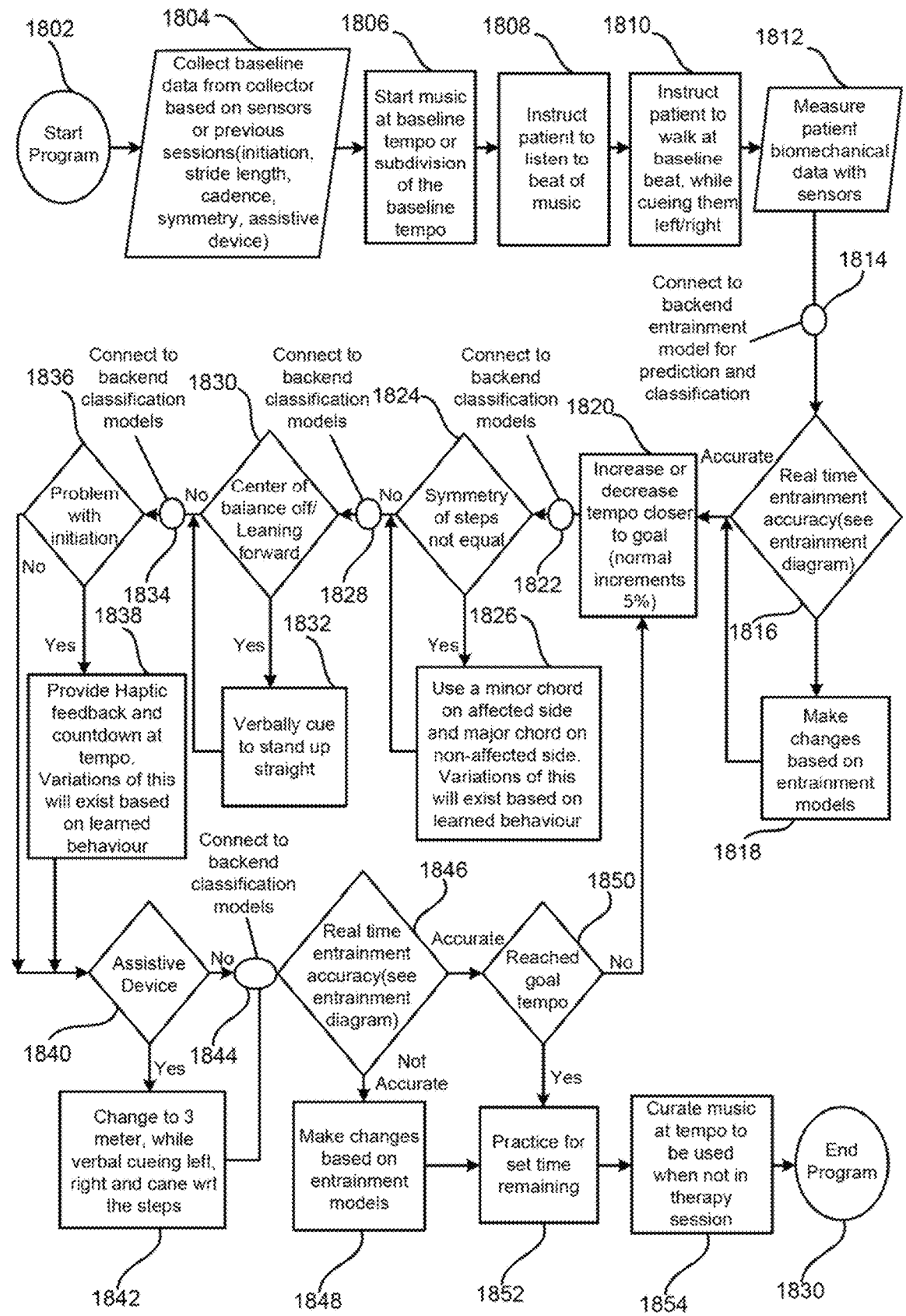
FIG. 18 illustrates an implementation of a technique for gait training of a patient in accordance with exemplary embodiments of the disclosed subject matter.

FIG. 18 illustrates a technique useful for gait training, wherein the repetitive movement refers to the steps taken by the patient while walking. Gait training is adapted to individual patient populations, diagnosis, and conditions to deliver personalized and individualized music interventions. Based on the inputs, the program changes the content, cadence, major/minor chords, meter, and musical cues (e.g., melodic, harmonic, and force cues) where applicable. The program can make selections of music by using date of birth, listed music preferences, and entraining tempo to provide a playlist of passive music to use on a regular basis. The key inputs for gait training are cadence, symmetry and stride length of the user executing the physical activity, e.g., walking. The program uses connected hardware to provide haptic/vibration feedback at the BPM of the music. The appropriate populations for gait training include patients with traumatic brain injury (TBI), stroke, Parkinson's, MS and aging.

The method starts at step 1802. At step 1804, biomechanical data is received at the collector 106 based on data from sensors, e.g., sensors 200, 206, 208. Biomechanical data includes initiation, stride length, cadence, symmetry, data about assistive device, or other such patient feature sets that were stored and generated by the analytics systems 108. Exemplary biomechanical data parameters are listed in Table 1, 2, and 3 above. The baseline condition is determined from a one or more sources of data. First, the patient's gait without any music being played is sensed. Sensor and feature data regarding the patient's initiation, stride length, cadence, symmetry, data about assistive device, etc. comprise the patient's baseline biomechanical data for a therapy session. Second, sensor data from previous sessions of the same patient, as well as any higher level classification data from analytics system 108 comprise the patient's historical data. Third, sensor data and higher level classification data for other similarly-situated patients comprise population data. Thus, the Baseline condition can include data from one or more of (a) the patient's baseline biomechanical data for a therapy session, (b) data from the patient's previous sessions, and (c) population data. The baseline beat tempo is then selected from the baseline condition. For example, a baseline beat tempo can be selected to match the current cadence of the patient prior to playing music. Alternatively, the baseline beat tempo can be selected as a fraction or multiple of the current cadence of the patient. As another alternative, the baseline tempo can be selected to match the baseline beat tempo used in the same patient's previous session. As yet another alternative, the baseline beat tempo can be selected based on baseline beat tempos used for other patients with similar physical conditions. Finally, the baseline beat tempo can be selected based on a combination of any of the data described above. A goal beat tempo can also be determined from this data. For example, the goal beat tempo may be selected as a percentage increase in the baseline beat tempo by reference to the improvement exhibited by other similarly situated patients. The tempo is understood to refer to the frequency of beats in the music.

At step 1806, music provided to the patient on music delivery device 230 (e.g., earbuds or headphones, or a speaker) from handheld device 220 is started at baseline tempo or a subdivision of the baseline tempo. In order to supply music to the patient at the baseline tempo, music is having a constant baseline tempo is selected from a database, or existing music is modified, e.g., selectively sped up or slow down, in order to provide beat signals at a constant tempo.

At step 1808, the patient is instructed to listen to the beat of the music. At step 1810, the patient is instructed to walk at the baseline beat tempo, optionally receiving cues as to left and right feet. The patient is instructed to walk such that each step closely matches the beat of the music, e.g., to walk "in time" with the beat tempo. Steps 1806, 1808, and 1810 may be initiated by the therapist, or by audible or visual instructions on the handheld device 220.

At step 1812, the sensors 200, 206, 208 on the patient are used to record patient data, such as heel strike pressure, 6-Dimensional movement, EMG activity, and a video record of patient movement. All sensor data is time-stamped. Data analysis is performed on the time-stamped sensor data including "gate" analysis discussed herein. For example, analysis of the sensor data, e.g., heel strike pressure, is made in order to determine the onset time of each step. Additional data received includes the time associated with each beat signal of the music provided to the patient.

At step 1814, a connection is made to the entrainment model (e.g., the ensemble machine learning system 410 of the analytics system 108 or models downloaded on collector 106 and running on the handheld device 220) for prediction and classification. (It is understood that such connection may be pre-existing or initiated at this time.) Such connection is typically very fast or instantaneous.

At step 1816, an optional entrainment analysis performed at the analytics systems 108 is applied to the sensor data. The entrainment analysis includes the determination of the delay between the beat signal and the onset of each step taken by the patient. As an output from the entrainment analysis, a determination is made regarding the accuracy of the entrainment, e.g., a measure of the instantaneous relationship between the baseline tempo and the patient's step as discussed above regarding the entrainment potential and EP ratio. If the entrainment is not accurate, e.g., entrainment potential is not constant within a tolerance, adjustments are made at step 1818, e.g., speed up or slow down the beat tempo, increase volume, increase sensory input, overlay metronome or other related sound, etc. If the entrainment is accurate, e.g., entrainment potential is constant within a tolerance, an incremental change is made to the tempo at step 1820. For example, the baseline tempo of the music played with handheld device is increased towards a goal tempo, e.g., by 5%.

At step 1822, a connection is made to the entrainment model for prediction and classification. (It is understood that such connection may be pre-existing or initiated at this time.) At step 1824, an optional symmetry analysis is applied to the sensor data. As an output from the symmetry analysis, a determination is made regarding the symmetry of the patient's gait, e.g., how closely the patient's left foot motion matches the patient's right foot motion for stride length, speed, stance phase, swing phase, etc. If the steps are not symmetrical, e.g., below a threshold, adjustments are made at step 1826 to the music broadcast to the patient by the handheld device. A first modification may be made to the music played during movement of one of the patient's feet, and the second modification may be made to music played during movement of the other one of the patient's feet. For example, a minor chord (or increased volume, sensory input, change in tempo, or overlay of sound/metronome) may be played on one side, e.g., an affected side, and a major chord played on the other side, e.g., a non-affected side. The machine learning system 410 predict in advance when symmetry problems are coming based on the 'fingerprint' of the scenarios leading up to it, e.g., by analyzing motions that are indicative of asymmetry. Asymmetry can be determined by comparing the normal gait parameters for someone with their background can determine how affected the side is and compared to other side.

At step 1828, connection is made to the entrainment model for prediction and classification. (It is understood that such connection may be pre-existing or initiated at this time.) At step 1830, an optional center of balance analysis, e.g., whether the patient is leaning forward, is performed on the sensor data. The analysis may be performed by combining outputs of the foot sensors, as well as the video output. As an output from the center of balance analysis, a determination is made regarding whether the patient is leaning forward. If the patient is leaning forward, a cue to the patient to "stand up straight" is made at step 1832, provided by the therapist, or by audible or visual instructions on the handheld device.

At step 1834, a connection is made to the entrainment model for prediction and classification. (It is understood that such connection may be pre-existing or initiated at this time.) At step 1836, an initiation analysis is applied to the sensor data, e.g., patient's exhibits hesitation or difficulty initiating walking. As an output from the initiation analysis, a determination is made regarding the whether the patient exhibits a problem with initiation. If the patient exhibits a problem with initiation, e.g., below a threshold, haptic feedback can be provided to the patient, which may include a countdown at the beat tempo or a countdown prior to the beginning of a song at step 1838.

At step 1840, it is optionally determined whether the patient is using an assistive device, e.g., a cane, crutches, walker, etc. In some embodiments, the handheld device 220 provides a user interface for the patient or therapist to enter information regarding the use of an assistive device. If a cane is present, the analysis is changed to three meter, e.g., cane, right foot, left foot, and cueing by "left foot," "right foot," and "cane," is made at step 1842, provided by the therapist, or by audible or visual instructions on the handheld device.

At step 1844, a connection is made to the entrainment model for prediction and classification. (It is understood that such connection may be pre-existing or initiated at this time.) An optional entrainment analysis 1846 is applied to the sensor data, substantially as described above in step 1816, with the differences noted herein. For example, entrainment may be compared with previous entrainment data from earlier in the session, from previous sessions with the patient, or with data relating to entrainment of other patients. As an output from the entrainment analysis, a determination is made regarding the accuracy of the entrainment, e.g., how closely the patient's gait matches the baseline tempo. If the entrainment is not accurate, adjustments are made at step 1848, substantially in the same manner as described above at step 1818.

If the entrainment is accurate, a determination is made at step 1850 whether the patient is walking at the goal tempo. If the goal tempo is not reached, the method proceeds to step 1820 (described above), so that an incremental change is made to the tempo. For example, the baseline tempo of the music played with handheld device is increased or decreased, e.g., by 5%, towards the goal tempo. If the goal tempo has been reached, the patient may continue the therapy for the remaining time in the session (step 1852). At step 1854, music at the desired tempo to be used when not in therapy session can be curated and left on the device 220 in FIG. 2. This music content is used as homework/practice by the patient between dedicated therapy sessions. At step 827, the program ends.

Is understood that the steps described above and illustrated in FIG. 18 may be performed in a different order than that disclosed. For example, the evaluations at steps 1816, 1824, 1830, 1836, 1840, 1846, and 1850 may be performed at the same time. Moreover, the plurality of connections to the analytics system 108 (e.g., steps 1814, 1822, 1828, 1834, and 1844) may be performed once throughout the therapy session described.

Figure 19:
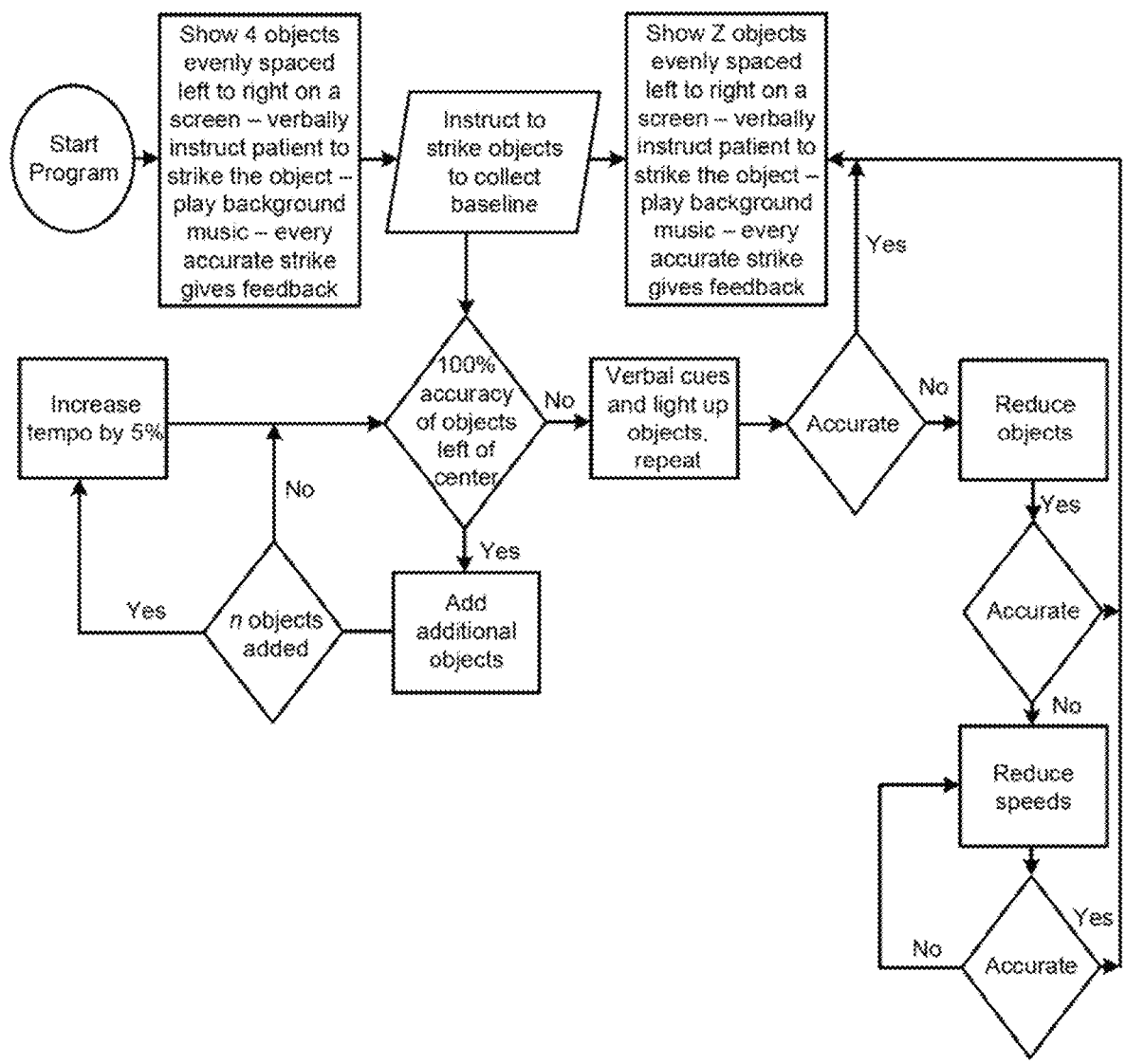
FIG. 19 illustrates an implementation of a technique for neglect training of a patient in accordance with exemplary embodiments of the disclosed subject matter.

FIG. 19 illustrates a technique useful for neglect training. For neglect training, the system and methods described herein use connected hardware to provide haptic/vibration feedback as the patients correctly hit the target. The connected hardware includes a device, video motion capture system or connected bell. All of these devices connect into the system described, vibrate as tapped, and have a speaker to play auditory feedback. For example, the connected bell provides data to the system in the same manner as the sensors 200, e.g., data regarding the bell strike by the patient. The video motion capture system provides video data to the system in the same manner as the video cameras 206. The key inputs for neglect training are information relating to the tracking of movement to a specific location. The program uses connected hardware to provide haptic/vibration feedback as the patient correctly hits the target. The appropriate populations for neglect training include patients with spatial neglect or unilateral visual neglect conditions.

Figure 20:
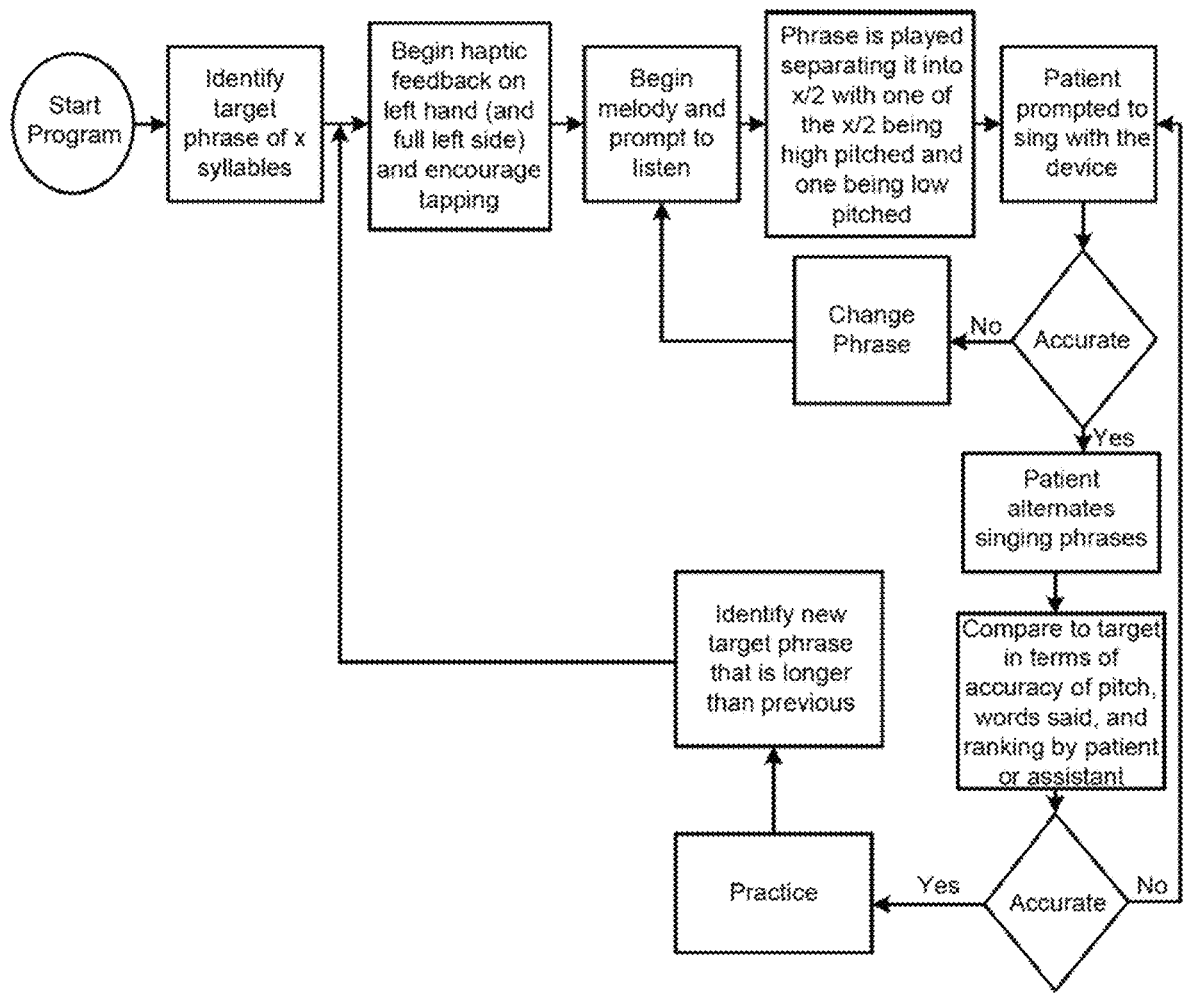
FIG. 20 illustrates an implementation of a technique for intonation training of a patient in accordance with exemplary embodiments of the disclosed subject matter.

The flow diagram illustrated in FIG. 19 for neglect training is substantially identical to the flow illustrated in FIG. 18 for gait training, with the differences noted herein. For example, a baseline test establishes the status of the patient and/or improvement from previous tests. In some embodiments the baseline tests include showing four objects evenly spaced left to right on a screen, e.g., display 222 of handheld device 220. The patient is instructed, either by cues appearing on the display 222 or verbally by a therapist, to strike the object in time with the beats of the background music. As with gait training, the patient is instructed to strike a bell in time with the beat of the background music. Every accurate strike provides feedback. Once the baseline information is collected, a number of objects evenly spaced left to right are displayed on a screen. As above, the patient is instructed to strike the objects in order from left to right in time with the beats of the background music. Every accurate strike provides a feedback. As with gait training, the analytics system 108 evaluates the patient's responses and classifies the responses and provide instructions to add or reduce objects, or increase or decrease tempo of the music to reach a goal tempo FIG. 20 illustrates a technique useful for intonation training. For intonation training, the system and methods described herein relies on voice processing algorithms. The phrases typically chosen are common words in the following categories: bilabials, gutturals, and vowels. The hardware is connected to a patient to provide haptic feedback at the beats per minute to one hand of the patient. The key inputs for intonation training are the tone of voice and words spoken and rhythm of speech. The appropriate populations for intonation training include patients with Broca's aphasia, expressive aphasia, non-fluent aphasia, apraxia, autism spectrum disorder, and Down's syndrome.

The flow diagram illustrated in FIG. 20 for intonation training is substantially identical to the flow illustrated in FIG. 18 for gait training, with the differences noted herein. For example, haptic feedback is provided to one hand of the patient to encourage tapping. The patient is then instructed, either by cues appearing on the display 222 or verbally by a therapist, to listen to the music played. The spoken phrase to be learned is played by separating it into two parts, with the first one of the two parts being high-pitched and the second of the two parts being low pitched. The patient is then instructed, either by cues appearing on the display 222 or verbally by a therapist, to singing the phrase with the device using the two pitches being played. As with gait training, the analytics system 108 evaluates the patient's responses and classifies the responses in terms of accuracy of pitch, words spoken, and ranking by patient or assistant/therapist, and provide instructions to provide alternate phrases and compare responses to targeted speech parameters.

Figure 21:
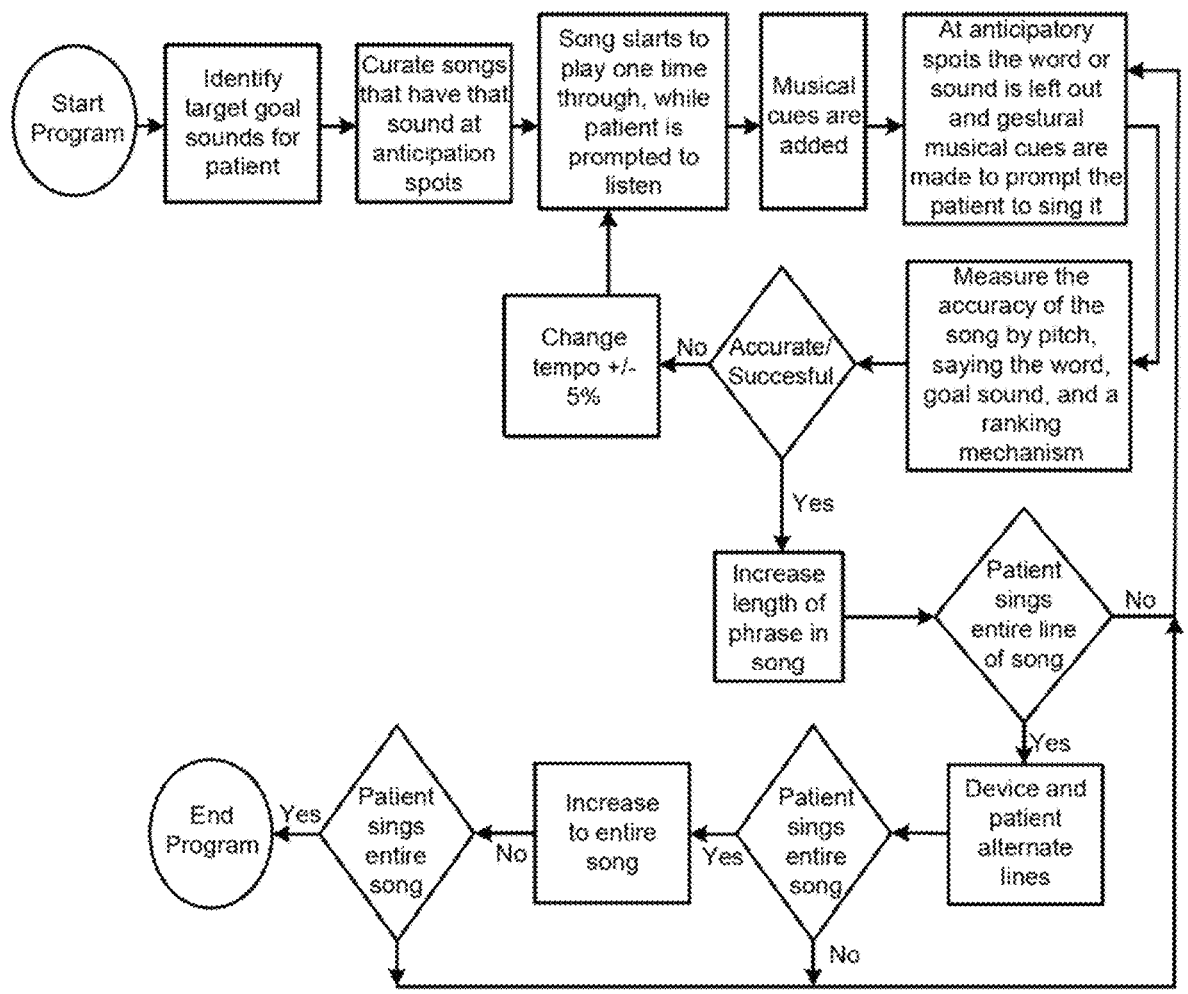
FIG. 21 illustrates an implementation of a technique for musical stimulation training of a patient in accordance with exemplary embodiments of the disclosed subject matter.

FIG. 21 illustrates a technique useful for musical stimulation training. For musical stimulation training, the system and methods described herein relies on voice processing algorithms. Familiar songs are used with an algorithm to separate the anticipatory section out (referred to as an expectancy violation). The hardware includes a speaker for receiving and processing the singing by the patient, and in some embodiments a therapist can manually provide an input regarding singing accuracy. Key inputs are information relating to the tone of voice and words spoken and rhythm of speech, and music preferences. The appropriate populations include patients with Broca's aphasia, non-fluent aphasia, TBI, stroke, and primary progressive aphasia.

The flow diagram illustrated in FIG. 21 for musical stimulation training is substantially identical to the flow illustrated in FIG. 18 for gait training, with the differences noted herein. For example, a song is played for the patient, and the patient instructed either by cues appearing on the display 222 or verbally by a therapist, to listen to the song. Musical cues are added to the song. Subsequently, at anticipatory spots, a word or sound is left out and gestural music cues are played to prompt the patient to sing the missing word or sound. As with gait training, the analytics system 108 evaluates the patient's responses and classifies the responses in terms of accuracy of pitch, words spoken, and ranking by patient or assistant/therapist, and provide instructions to play additional portions of the song in order to improve speech to targeted speech parameters.

Figure 22:
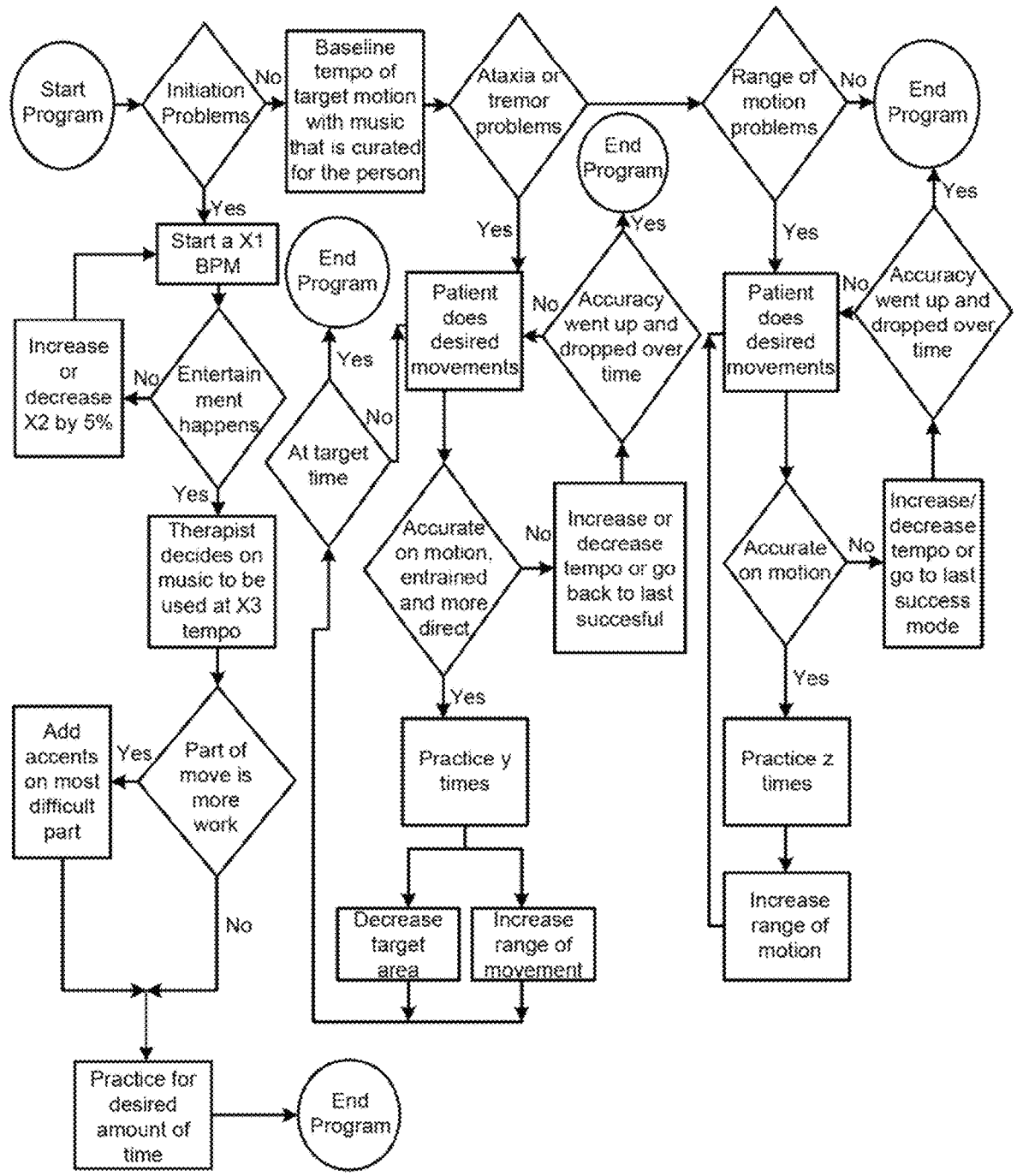
FIG. 22 illustrates an implementation of a technique for gross motor training of a patient in accordance with exemplary embodiments of the disclosed subject matter.

FIG. 22 illustrates a technique useful for gross motor training. For gross motor training, the system and methods described herein are directed to help with ataxia, range of motion or initiation. The more challenging portion of an exercise is musically "accented", e.g., by the use of melodic, harmonic, rhythmic, and/or force cues. Key inputs are information relating to movements in X, Y, and Z-capture via connected hardware or video camera system. The appropriate populations include patients with neurological, orthopedic, strength, endurance, balance, posture, range of motion, TBI, SCI, stroke, and Cerebral Palsy.

The flow diagram illustrated in FIG. 22 for gross motor training is substantially identical to the flow illustrated in FIG. 18 for gait training, with the differences noted herein. As with gait training, the patient's is provided with cues to move in time with the baseline beats of a musical selection. The analytics system 108 evaluates the patient's responses and classifies the responses in terms of accuracy of motion and entrainment as discussed above and provides instructions to increase or decrease the tempo of the music played.

Figure 23:
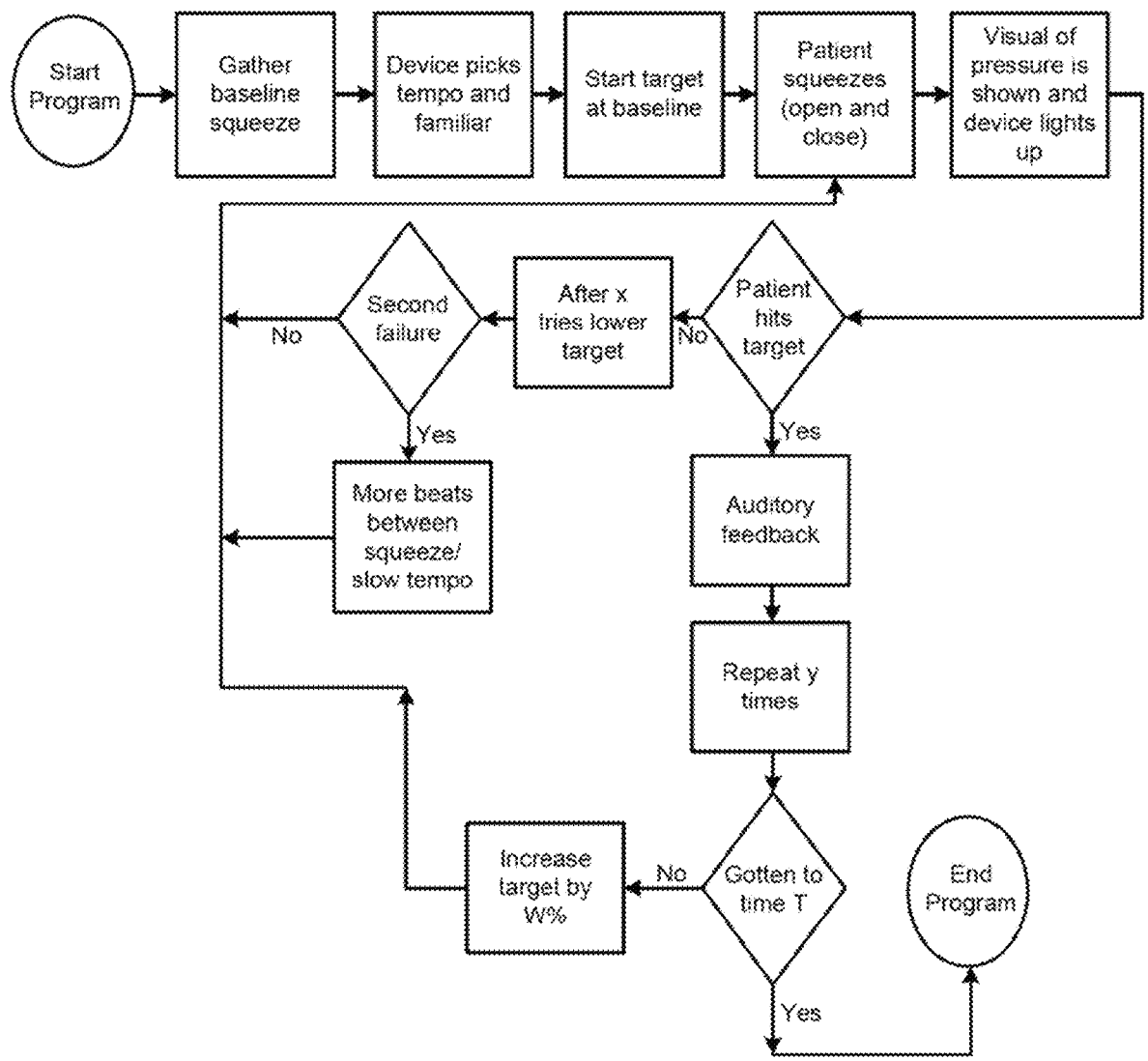
FIG. 23 illustrates an implementation of a technique for grip strength training of a patient in accordance with exemplary embodiments of the disclosed subject matter.

FIG. 23 illustrates a technique useful for grip strength training. For grip strength training, the system and methods described herein rely on sensors associated with the gripper device. The hardware includes a gripper device having pressure sensors, a connected speaker associated with a handheld device 220. Key inputs are the pressure provided by the patient to the gripping device in a similar manner to the heel strike pressure measured by sensor 200. The appropriate populations include patients with neurological, orthopedic, strength, endurance, balance, posture, range of motion, TBI, SCI, stroke, and Cerebral Palsy.

The flow diagram illustrated in FIG. 23, for grip strength training is substantially identical to the flow illustrated in FIG. 18 for gait training, with the differences noted herein. As with gait training, the patient is provided with cues to apply force to the gripping device in time with the baseline beats of a musical selection. The analytics system 108 evaluates the patient's responses and classifies the responses in terms of accuracy of motion and entrainment as discussed above and provides instructions to increase or decrease the tempo of the music played.

Figure 24:
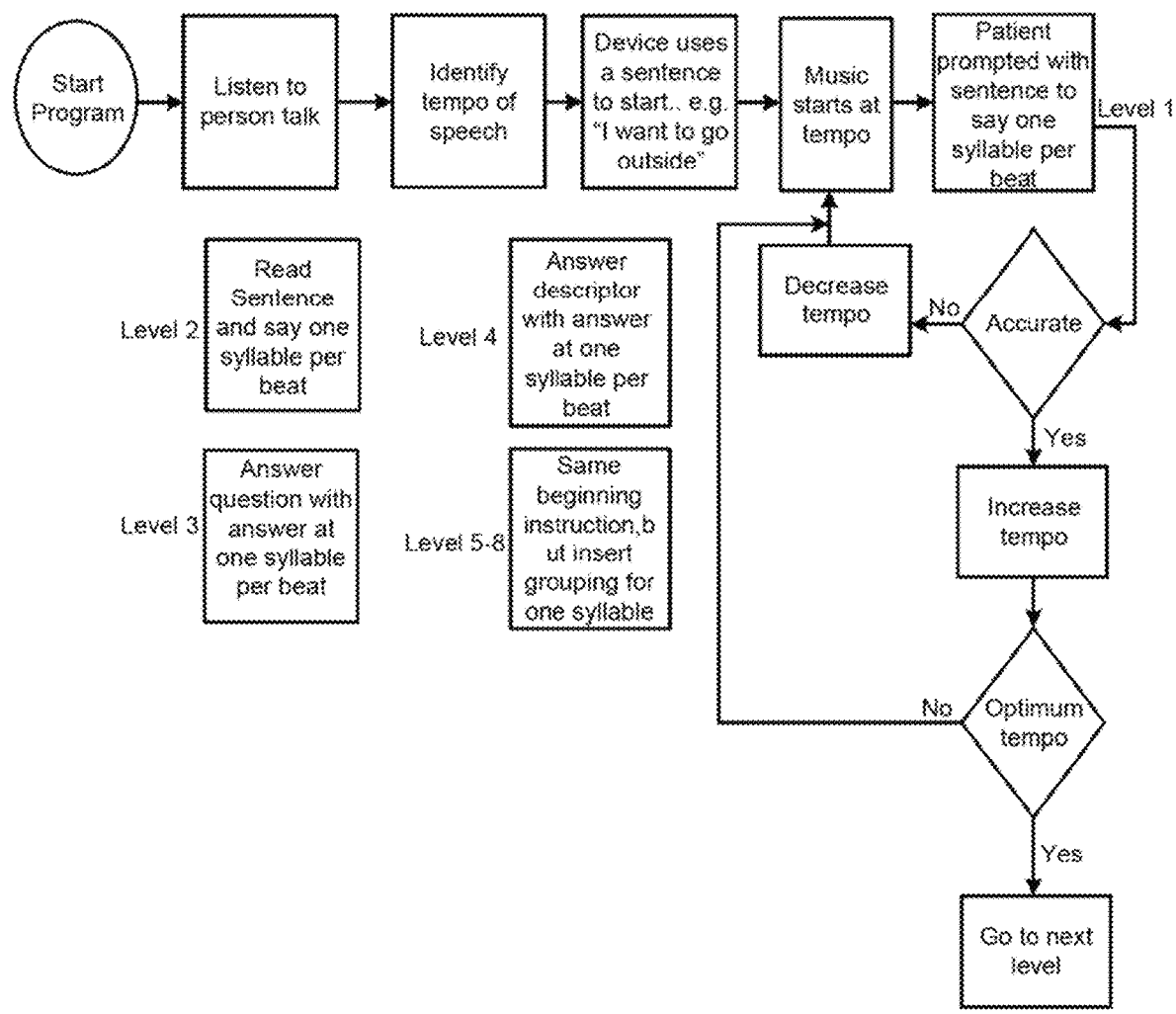
FIG. 24 illustrates an implementation of a technique for speech cueing training of a patient in accordance with exemplary embodiments of the disclosed subject matter.

FIG. 24 illustrates a technique useful for speech cueing training. For speech cueing training, the system and methods described herein relies on voice processing algorithms. The hardware can include a speaker for receiving and processing the singing by the patient, and in some embodiments a therapist can manually provide an input regarding speech accuracy. Key inputs are the tone of voice and words spoken and rhythm of speech, and music preferences. The appropriate populations include patients with robot, word finding and stuttering speech issues.

The flow diagram illustrated in FIG. 24 for speech cueing training is substantially identical to the flow illustrated in FIG. 18 for gait training, with the differences noted herein. As with gait training, the patient is provided with cues to speak a sentence, either by cues appearing on the display 222 or verbally by a therapist, by saying one syllable in time with each beat of a musical selection. The analytics system 108 evaluates the patient's speech and classifies the responses in terms of accuracy of speech and entrainment as discussed above and provides instructions to increase or decrease the tempo of the music played.

Figure 25:
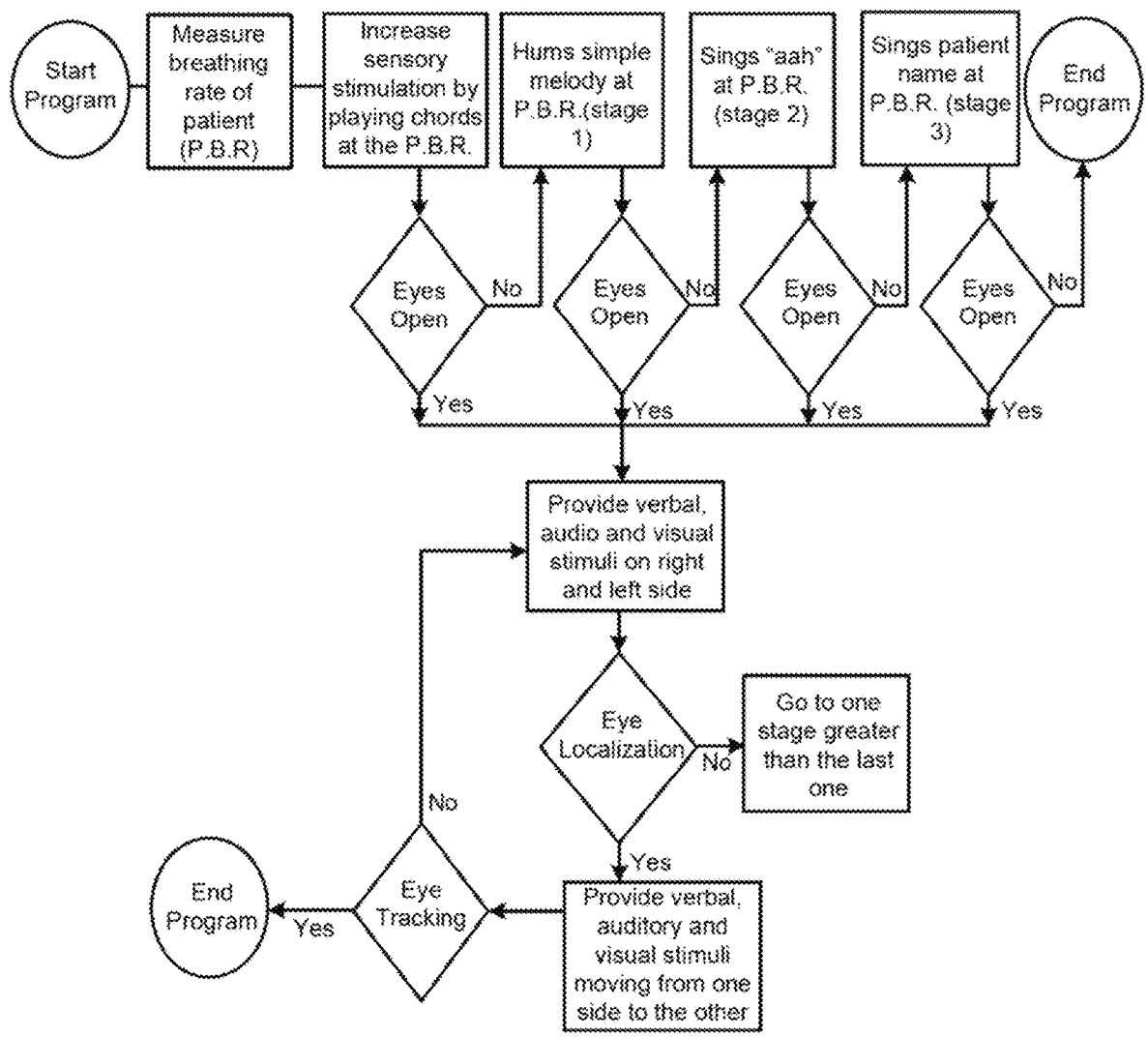
FIG. 25 illustrates an implementation of a technique for training of a minimally conscious patient in accordance with exemplary embodiments of the disclosed subject matter.

FIG. 25 illustrates a technique useful for training of minimally conscious patients. The system and methods described herein rely on an imaging system, such as a 3-D camera, to measure if the eyes of the patient are open, the direction the patient is looking, and the resulting patient pulse or heart rate. The program searches and optimizes for the heart rate, stimulation, respiration rate, eye closure, posturing, and restlessness. The appropriate populations include patients with coma and disorders of consciousness.

The flow diagram illustrated in FIG. 25 for training of minimally conscious patients is substantially identical to the flow illustrated in FIG. 18 for gait training, with the differences noted herein. As with gait training, the patient is provided with increasing stimulation at the breathing rate of the patient (PBR). For example, the patient is first provided with stimulation at the PBR of musical chords and observing whether the patient's eyes are open. If the patient's eyes are not open, the stimulation sequentially increases from humming a simple melody at PBR, to singing "aah" at the PBR, to singing the patient's name at the PBR (or playing a recording of such sounds), and checking at each input whether the patient's eyes are open. The analytics system 108 evaluates the patient's eye tracking and classifies the responses in terms of level of consciousness and provides instructions to change the stimulation.

Figure 26:
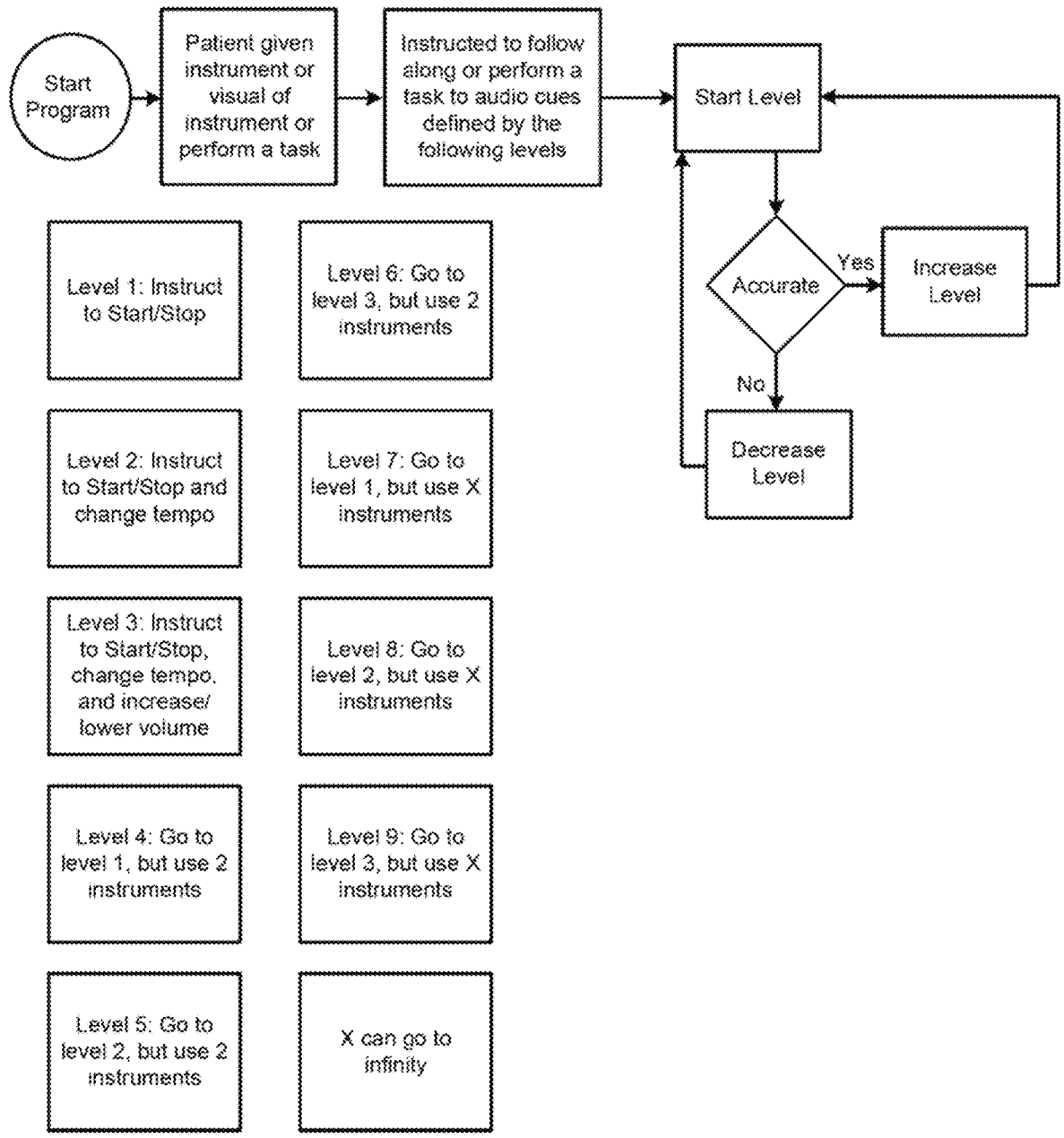
FIGS. 26-28 illustrates an implementation of a technique for attention training of a patient in accordance with exemplary embodiments of the disclosed subject matter.
Figure 27:
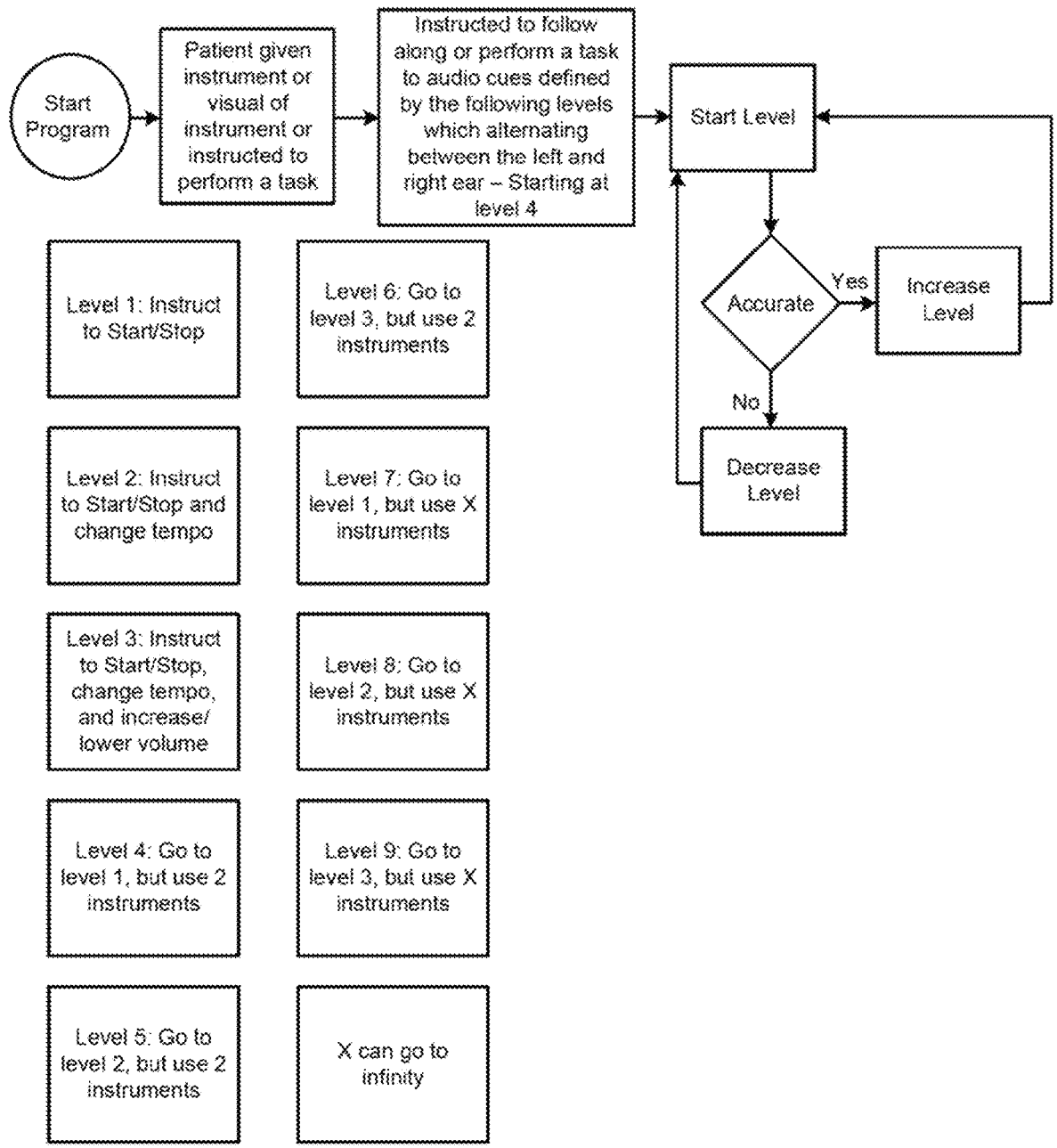
Figure 28:
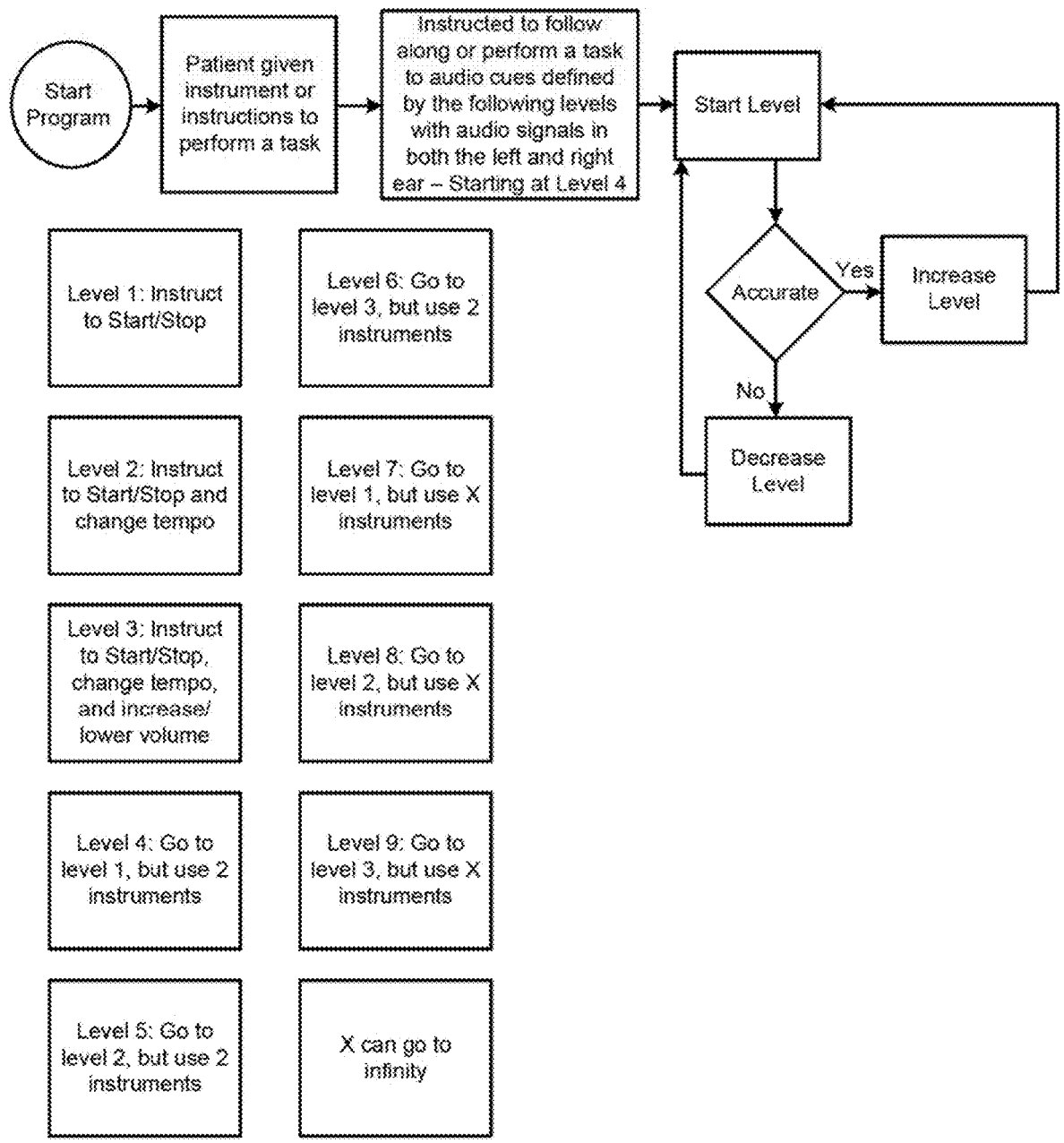

FIGS. 26-28 illustrate a technique useful for attention training. For attention training, the system and methods described herein operate in a closed loop fashion to help patients sustain, divide, alternate and select attention. No visual cue is allowed to signal which movements to make. The appropriate populations include patients with brain tumor, multiple sclerosis, Parkinson's disease, and neurological disease and injury.

The flow diagram illustrated in FIG. 26 for sustained attention training is substantially identical to the flow illustrated in FIG. 18 for gait training, with the differences noted herein. As with gait training, the patient is provided with an instrument (e.g., any instrument could work, such as a drumstick, drum, keyboard, or wirelessly connected version of each) and is instructed, either by cues appearing on the display 222 or verbally by a therapist, to follow along or perform a task to audio cues defined by levels 1 through 9 as illustrated in FIG. 26. The analytics system 108 evaluates the patient's ability to accurately complete the task and classifies the responses to change the tempo or the difficulty of the task. Similarly, FIG. 27 illustrates a flow diagram for alternating attention training in which the instructions are provided, either by cues appearing on the display 222 or verbally by a therapist, to follow along or perform a task to audio cues which alternate between the left and the right ear. FIG. 28 illustrates a flow diagram for divided attention in which the instructions are provided to follow along or perform a task to audio cues with audio signals in both the left and right ear.

Figure 29:
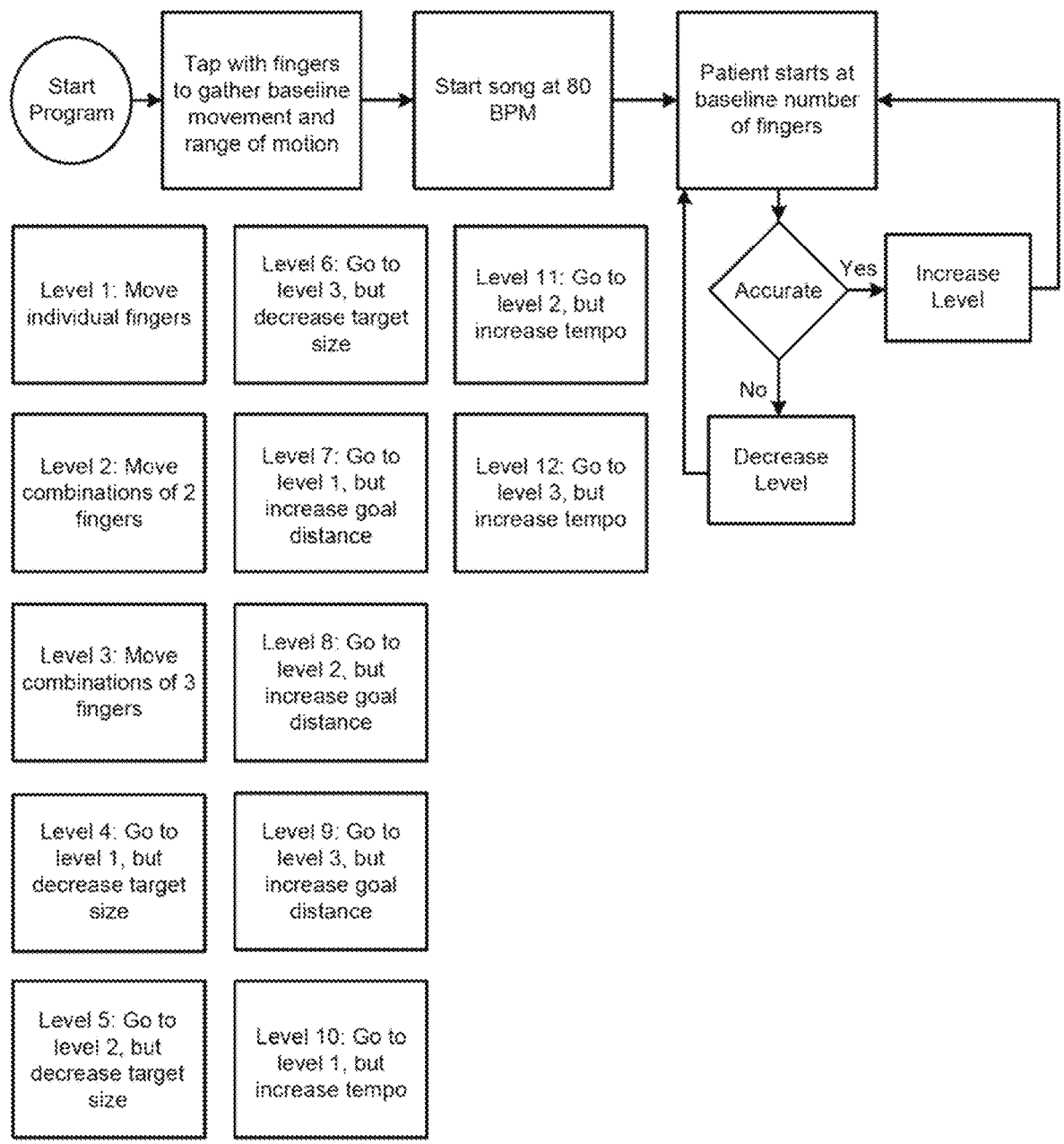
FIG. 29 illustrates an implementation of a technique for dexterity training of a patient in accordance with exemplary embodiments of the disclosed subject matter.

The flow diagram illustrated in FIG. 29 for dexterity training is substantially identical to the flow illustrated in FIG. 18 for gait training, with the differences noted herein. For dexterity training, the patient is instructed to tap with their fingers on the keyboard of the piano to gather baseline movement and range of motion information. The song is started at a particular beat per minute, and the patient starts tapping with the baseline number of fingers. The analytics system 108 evaluates the patient's ability to accurately complete the task and classifies the responses to change the tempo or the difficulty of the task.

Figure 30:
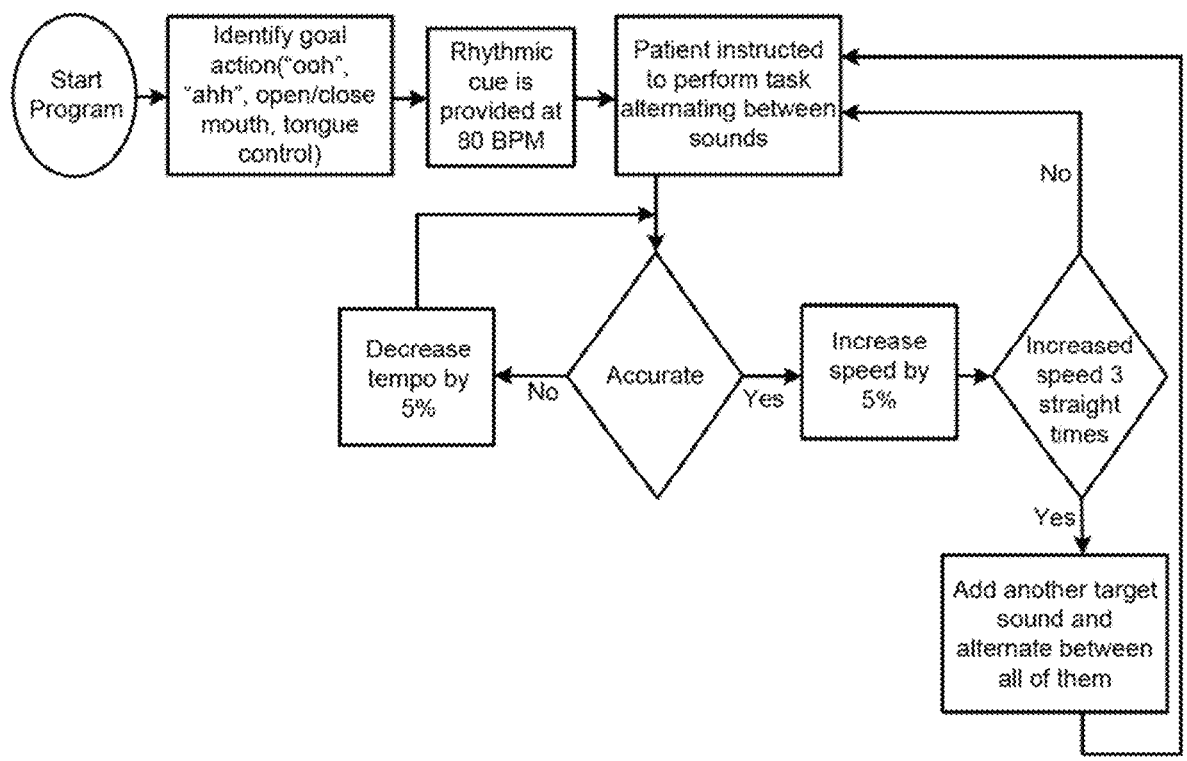
FIG. 30 illustrates an implementation of a technique for oral motor training of a patient in accordance with exemplary embodiments of the disclosed subject matter.

The flow diagram illustrated in FIG. 30 for oral motor training is substantially identical to the flow illustrated in FIG. 18 for gait training, with the differences noted herein. For oral motor training, the patient is instructed to perform a task alternating between two sounds, e.g., "ooh" and "aah." The analytics system 108 evaluates the patient's ability to accurately complete the task and classifies the responses to change the tempo or the difficulty of the task, e.g., by providing a different target sound.

Figure 31:
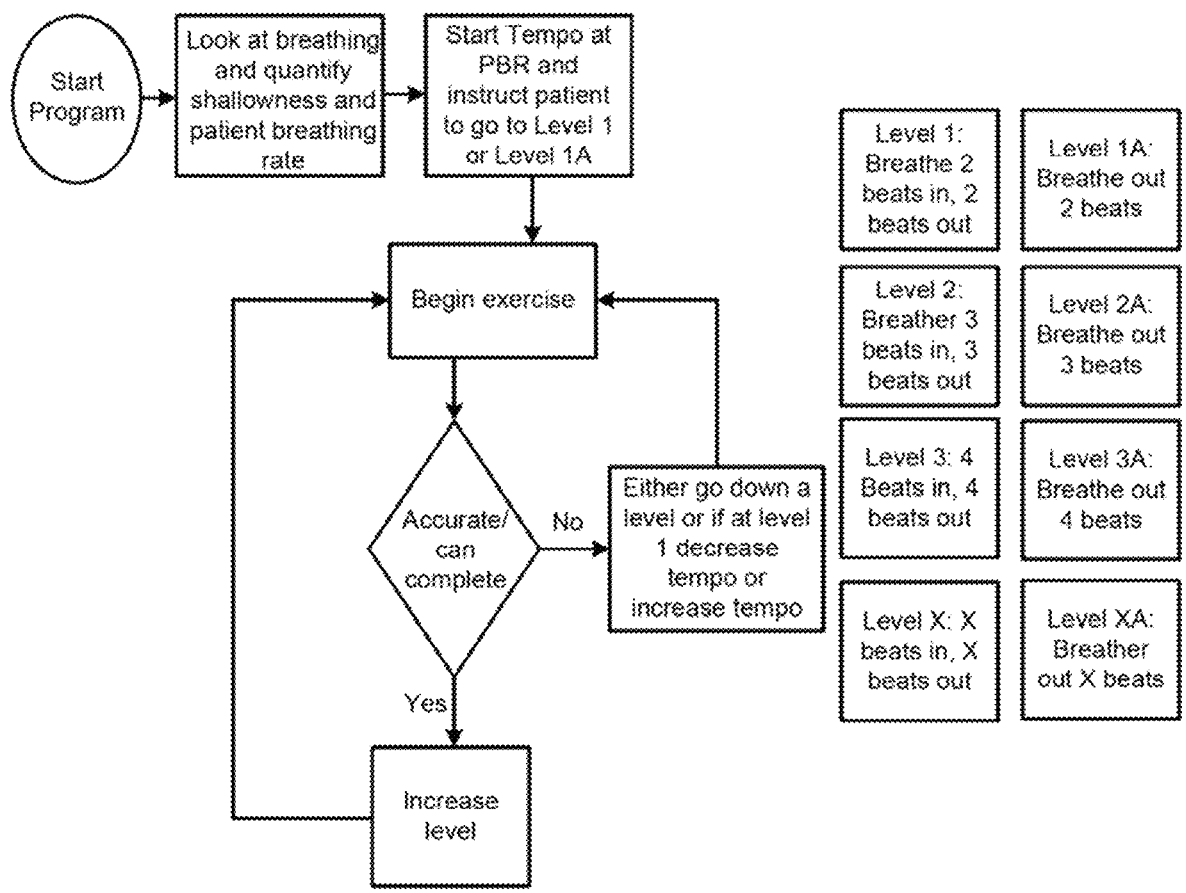
FIG. 31 illustrates an implementation of a technique for respiratory training of a patient in accordance with exemplary embodiments of the disclosed subject matter.

The flow diagram illustrated in FIG. 31 for respiratory training is substantially identical to the flow illustrated in FIG. 18 for gait training, with the differences noted herein. For respiratory training, a baseline breathing rate and shallowness of breathing is determined. Music is provided with a baseline tempo at the patient's breathing rate, and the patient is instructed to perform breathing tasks has described in the levels in FIG. 31. The analytics system 108 evaluates the patient's ability to accurately complete the task and classifies the responses to change the tempo or the difficulty of the task, e.g., by providing a different breathing pattern Further described herein are methods, system, and apparatus for using augmented reality (AR) and augmented audio (AA) to support the next generation of medical and therapy systems for the improvement or maintenance of motor functions. Exemplary embodiments of the augmented neurologic rehabilitation, recovery or maintenance ("ANR") systems and methods disclosed herein build upon entrainment techniques by utilizing additional sensor streams to make determinations of therapeutic benefit and inform a closed loop therapeutic algorithm. Exemplary systems and methods for neurologic rehabilitation, which can be utilized to realize embodiments of the ANR systems and methods, are shown and described above and in co-pending and commonly assigned U.S. patent application Ser. No. 16/569, 388 for "Systems and Methods for Neurologic Rehabilitation," to McCarthy et al., which is a continuation of U.S. Pat. No. 10,448,888, titled, "Systems and Methods for Neurologic Rehabilitation," issue date Oct. 22, 2019, which is based on and claims priority to U.S. Provisional Patent Application No. 62/322,504 filed on Apr. 14, 2016, entitled "Systems and Methods for Neurologic Rehabilitation," which are each hereby incorporated by reference herein as if set forth in their respective entireties herein.

In accordance with one or more embodiments, the ANR systems and methods can include a method for providing an AR 3-D dynamic model of specific people or objects that include obtaining the images, videos of the people or images by querying cloud and local databases. The ANR systems and methods can also be configured to fuse and/or synchronize the dynamic models, patients or humans, audio content, and context about the environment into a synchronized state taking advantage of the neuroscience of the ability of music to improve motor function as well as the neuroscience of how visual imagery can impact recovery (e.g. the use of mirror neurons).

In accordance with one or more embodiments, the ANR systems and methods include a method for combining AA techniques for repetitive motion activities. Augmented Audio (AA) combines real world sound with additional computer-generated audio "layers" that enhance sensory input. The neuroscience of rhythm at its core uses the stimulus to engage the motor system for repetitive motion activities such as walking. Adding AA to the therapy protocols enhances therapeutic effect, increases adherence to the therapy protocols and provides greater safety in the form of enhanced situational awareness to the patient. The disclosed embodiments configured for adding AA can mix many audio signals, including external environmental sound inputs, recorded content, rhythmic content, and voice guidance into a synchronized state taking advantage of the neuroscience of music. Additionally, it can include the ability to combine algorithmically generated music with underlying rhythmic cueing as detailed in [00218] for patients with motor or physical disabilities. This can be done by fusing this generative rhythm with inputs from a patient's real-time biometric data into an interactive feedback state. Exemplary systems and methods for algorithmically generating auditory stimulus for use in connection with neurologic rehabilitation are shown and described in co-pending and commonly assigned U.S. patent app. Ser. No. 16/743,946, filed Jan. 15, 2020, titled "ENHANCING MUSIC FOR REPETITIVE MOTION ACTIVITIES" to McCarthy et al., which is a continuation of U.S. patent application Ser. No. 16/044,240 filed Jul. 24, 2018, now U.S. Pat. No. 10,556,087 issued on Feb. 11, 2020, entitled "ENHANCING MUSIC FOR REPETITIVE MOTION ACTIVITIES", which claims the benefit of priority under 35 USC 119(e) of U.S. Provisional Application No. 62/536,264 filed Jul. 24, 2017, the entire contents of each of which are hereby incorporated herein as if set forth in their respective entireties herein.

Neuroplasticity, entrainment, the science of mirror neurons are the foundational scientific components supporting the disclosed embodiments. Entrainment is a term for the activation of the motor centers of the brain in response to an external rhythmic stimulus. Studies have shown that audio-motor pathways exist in the Reticulospinal tract, the part of the brain that is responsible for movement. Priming and timing of movements via these pathways demonstrate the motor system's ability to couple with the auditory system in order to drive movement patterns (Rossignol and Melville, 1976). The entrainment process has been shown to effectively increase walking speed (Cha, 2014), decrease gait variability (Wright, 2016), and lower fall risk (Trombetti, 2011). Neuroplasticity refers to the brain's ability to strengthen preexisting neural connections and, thus, allow an individual to acquire new skills over time. Studies have demonstrated that music facilitates changes in certain motor regions of the brain, indicating that music can promote neuroplasticity (Moore et al., 2017). Mirror neurons fire both when you perform an action and when you observe another performing an action. Thus, when you see another performing an action, your brain responds as though you were the one doing it. This allows us to learn behaviors by imitation. This is important in the context of the disclosed embodiments because as patients observe augmented reality human simulations, they can imitate their actions using mirror neurons.

In accordance with one or more embodiments, the ANR systems and methods are configured to process the images/videos to remove/add people/objects smaller or larger than a specified size from the images/videos, in response to patient or therapist exception conditions received as inputs to the ANR system. Such exceptions can be a patient response such as an instruction to reduce scene complexity, a therapist instruction to introduce occlusions which could be people/objects increasing scene complexity. The embodiments can support recording all data of all patient or therapist exception conditions besides the session data itself.

In accordance with one or more embodiments, the ANR systems and methods include a telepresence method allowing the linking of a therapist to a remotely located patient using the system. The telepresence method, besides fully supporting all the local features experienced by patient and therapist when being in the same location, includes biomechanical motion tracking of the patient relative to the AR 3-D dynamic model of people/objects.

The AR 3-D dynamic model is a software-based algorithmic process of the ANR systems and methods for generating a presenting an AR/VR visual scene to the patient that is animated based on the foundational principals of neuroplasticity, entrainment, and the science of mirror neurons to facilitate outcomes towards a clinical or training goal. The telepresence method is configured to provide the ability to operate an interactive video link between the therapist and remotely located patient using the invention. The telepresence method supports projecting image/video from the remotely located patient with the invention to indicate the relative position of the patient in the AR 3-D dynamic model. The telepresence method can also provide the ability for the therapist to adjust AR models in real time (spatial location or which items are available) and allow modifications to the session. It will also allow a therapist to see the patient relative to the models.

Figure 32:
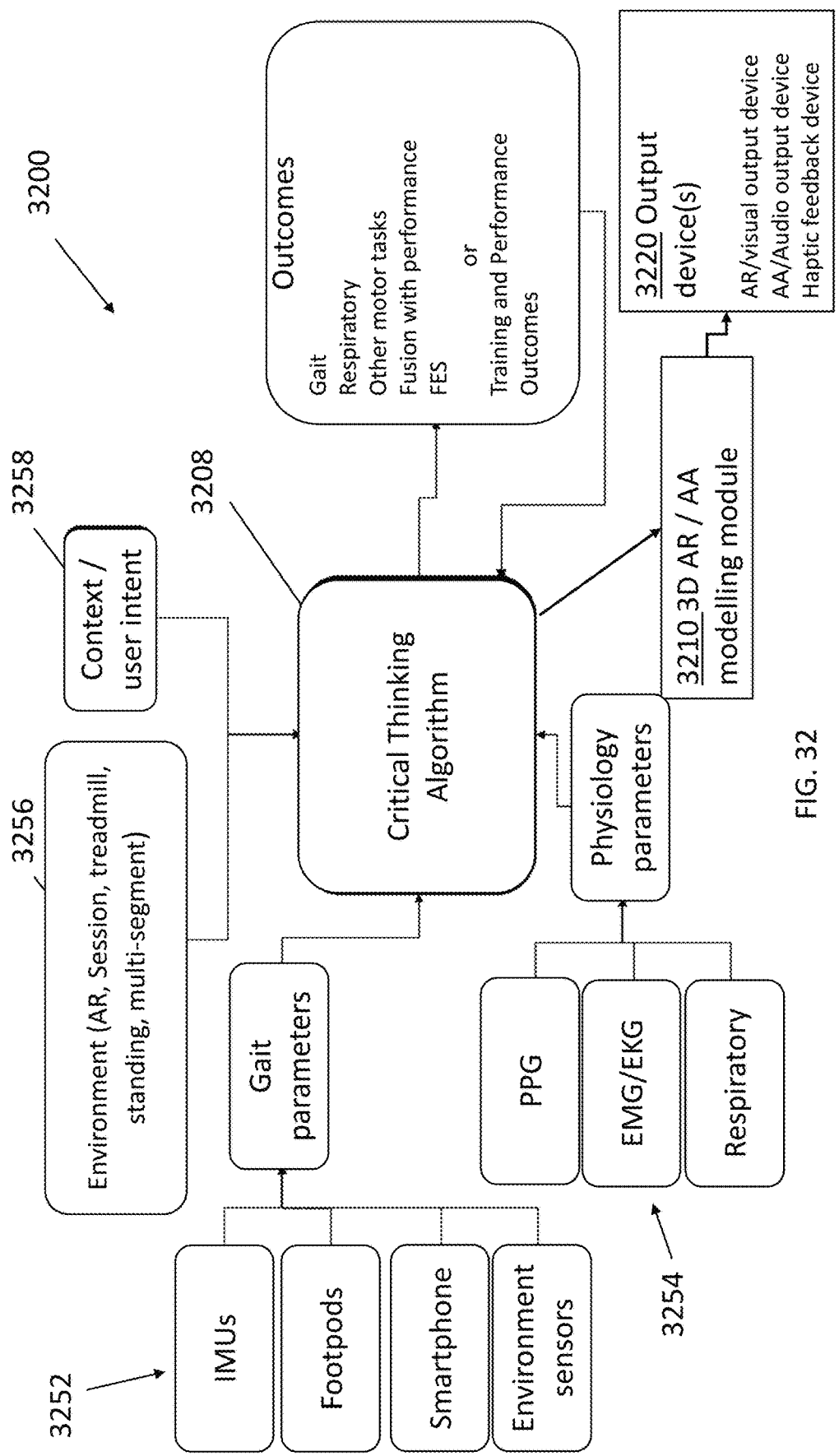
FIG. 32 is a diagram illustrating an augmented neurologic rehabilitation, recovery or maintenance ("ANR") system for providing therapy to a patient in accordance with exemplary embodiments of the disclosed subject matter.

FIG. 32 depicts a conceptual overview of principal components of an exemplary ANR system 3200 that uses a closed loop feedback that measures, analyzes, and acts on a person to facilitate outcomes towards a clinical or training goal. It should be understood that the ANR system 3200 can be realized using the various hardware and/or software components of the system 100 described above. As shown, the ANR system measures or receives inputs relating to gait parameters, environment, context/user intent (including past performance), physiological parameters, and real time feedback on outcomes (e.g. closed loop, real time decision making). One or a combination of these inputs can be directed into the clinical thinking algorithm module (CTA) 3208, which is in control of analyzing and acting on this information. In some embodiments, an example of real-time feedback would be a determination by the CTA 3208 that the user's measured quality of gait metrics (e.g. symmetry, stability and gait cycle time variance) have exceeded modeled safety thresholds, thus triggering a new cueing response. Such cueing responses are both visual and audio, for example, increasing the beat salience in the music by adding a metronome audio layer and modifying the AR scenery to model or direct the user into a safer gait speed and movement behavior.

At the CTA module 3208, the actions performed by the ANR system are defined based on the analysis of the inputs. The actions can be output to the patient in the form of various types of stimuli, including music (or other components), rhythm, sonification of sound, spoken words, augmented reality, virtual reality, augmented audio, or tactile feedback. As shown in FIG. 32, determinations made by the critical thinking algorithm relating to the various inputs, outcomes etc., are provided to an AR/AA output modelling module 3210 programmed to dynamically generate/modify outputs for the patient. The outputs are provided to the patient via one or more output devices 3220, such as visual and/or audio output devices and/or tactile feedback devices. For example, AR visual content can be output to AR glasses 3222 worn by the patient. Augmented audio content can be provided to the patient via audio speakers or headphones 3225. As would be understood, other suitable visual or audio display devices can be used without departing from the scope of the disclosed embodiments. Additionally, although various elements of the system are shown separately in FIG. 32, it should be understood that features and functionality of various aspects of the system can be combined.

The clinical thinking algorithm module 3208 in this medical/therapy system can be configured to implement a critical thinking algorithm focusing on the recovery, maintenance, or enhancement of motor function, including but not limited to upper extremity, lower extremity, agitation, postural stability, foot drop, dynamic stability, breathing, mouth movements, respiratory, endurance, heart rate training, breathing frequency, optical flow, boundary support training, strategy training (ankle, knee, and hip), attractor coupling, muscle firing, training optimization, and gait. One or more of these CTA's could also be implemented in synchrony or combination with other interventions that share similar goals. Examples could include implementing CTAs in combination with functional electrical stimulation, deep brain stimulation, transcutaneous electrical nerve stimulation (TENS), Gamma frequency audio entrainment (20-50 Hz) or other electrical stimulation systems. Additionally, dosing and operations of CTA's could be combined with anti-spasticity medications or dosing in combination with neurotoxin injections. For example, the CTA could be applied or start during the time window that has been shown these interventions are at their peak effect or to be used prior to them getting to that point as a way to prime the motor system.

ANR System Inputs

The inputs to the ANR system 3200 are important to enable the system to measure, analyze, and act in a continuous loop facilitating outcomes towards a clinical or training goal.

Receiving an input at the system can include measuring the movements of the person via a sensor to determine the biomechanical parameters of movements (e.g. temporal, spatial, and left/right comparisons). These motion sensors could be placed anywhere on the body and could be a single sensor or an array of sensors. Other types of sensors could be used to measure other input parameters, which could include respiratory rate, heart rate, oxygen level, temperature, electroencephalogram (EEG) for recording of the brain's spontaneous electrical activity, electrocardiogram (ECG or EKG) for measuring the electrical activity of the heart, electromyogram (EMG) for evaluating and recording the electrical activity produced by skeletal muscles, photoplethysmogram (PPG) for detecting blood volume changes in the microvascular bed of tissue often using a pulse oximeter which measures changes in light absorption of skin, optical, inertial measurement units, video cameras, microphones, accelerometers, gyroscopes, infrared, ultrasonic, radar, RF motion detection, GPS, barometers, RFID's, radar, humidity, or other sensors that detect physiological or biomechanical parameters. For instance, in the exemplary ANR system 3200 shown in FIG. 32, gait parameters can be measured using one or more sensors 3252 such as IMUs, footpad sensors, smartphone sensors (e.g., accelerometers) and environmental sensors. Additionally, physiology parameters can be measured using one or more sensors 3254 such as PPG, EMG/EKG and respiratory rate sensors.

Additionally, contextual information about the outcomes desired, the use environment, data from past sessions, other technologies, and other environmental conditions can be received as inputs to the CTA module and adjust the CTA's response. For instance, as shown in FIG. 32, contextual information 3258 and environment input 3256 information can be received as inputs that further inform operation of the CTA 3208. An example of using contextual information is that information from the past about a user's gait pattern could be used in combination with Artificial Intelligence (AI) or Machine Learning (ML) systems to provide more personalized clinical goals and actions for the patient. These goals could modify target parameters such as limits on steps per minute, walking velocity, heart rate variability, oxygen consumption (VO2 max), breathing rate, session length, asymmetry, variability, distance walked, or desired heart rate.

Additionally, environmental information could be detected using Bluetooth Low Energy (BLE) beacons, or other wireless proximity techniques, such as wireless triangulation or angle of arrival, to facilitate wireless location triggers to have people/objects appear and/or disappear in the patient's field of view with respect to an AR 3-D dynamic model depending on detected location. In some embodiments, the AR 3-D dynamic model that is output by the ANR system can be controlled by the therapist and/or beacon triggers to change or maintain navigation requirements for the patient. These triggers could be used with gait or physiological data as described above to provide additional triggers, beside the wireless beacon triggers. For example, gait data feedback from IMU products allows for a gait feedback loop that provides the ANR system 3200 with the ability to effect change in the AR 3-D dynamic model software process.

Clinical Thinking Algorithm

In accordance with one or more embodiments, the CTA module 3208 implements clinical thinking algorithms that are configured to control the applied therapy to facilitate outcomes towards a clinical or training goal. Clinical goals could include items such as those discussed in connection with FIG. 18 through FIG. 31, and, by way of further example, interventions for agitation in Alzheimer's, dementia, bipolar disorder, and schizophrenia, and training/physical activity goals. This section discusses different non-limiting exemplary techniques that can be used to deliver an appropriate rehabilitation response as determined by the CTA, for example, modulating the rhythmic tempo and the synchronized AR visual scenery. Each of these techniques could be implemented using a stand-alone CTA or combined with each other. In one or more embodiments, the system 3200 can be configured to combine CTA(s) with entrainment principles for repetitive motion activities and, in other cases, they can be combined with each other towards other goals.

By way of example and without limitation, the CTA module 3208 of the ANR system 3200 can be configured to utilize the combination of the biomechanical, physiological data, and context to create a virtual treadmill output via the AR/AA output interfaces. While a treadmill keeps pace for someone with the movement of the physical belt, the virtual treadmill is dynamically adjusted using the CTA in accordance with the entrainment principle to modulate a person's walking or movement pace in a free-standing manner, similar to other movement interventions. Though, in addition to or instead of using a rhythmic stimulus to drive the individual towards a bio-mechanical goal as discussed previously, the virtual treadmill can be generated and dynamically controlled based on entrainment of the patient towards target parameters such as those listed above as target parameters.

The target parameters could be set based on input from a clinician, a user, historic data, baseline conditions, or towards a clinically meaningful point. Additional, target parameters could be set by or follow recommendations on exercise length, duration, and intensity specific to certain conditions such as heart disease, asthma, COPD, fall prevention, musculoskeletal conditions, osteoarthritis, and general aging.

Further described herein is an exemplary embodiment of the ANR system 3200 in which the CTA module 3208 is configured to utilize the biomechanical data, physiological data, and context to provide gait training therapy in the form of a virtual treadmill and rhythmic auditory stimulus output via the AR and AA output interfaces 3220.

Figure 37:
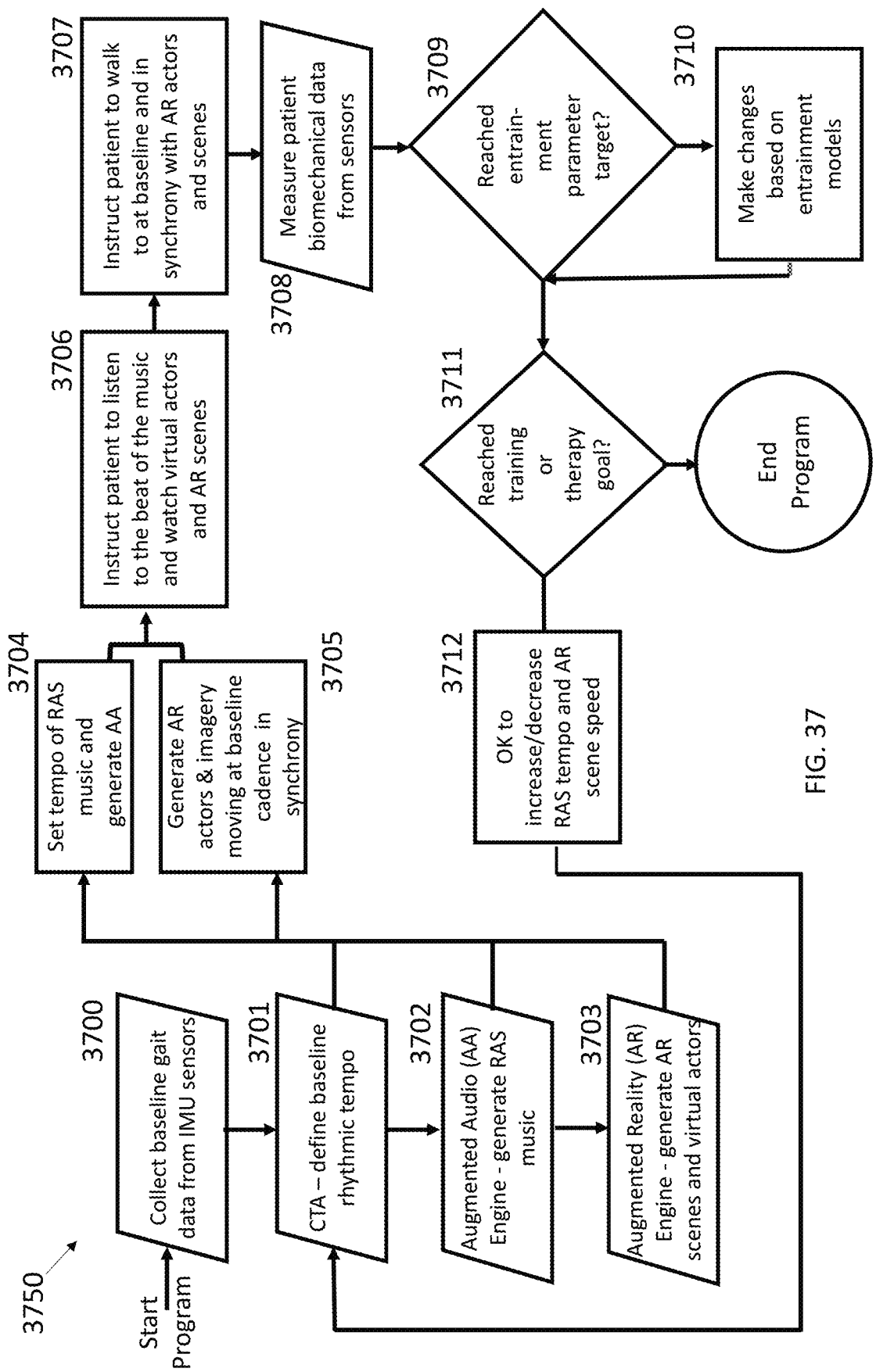
FIG. 37 illustrates an implementation of a technique for gait training by providing augmented audio and visual stimulus to a patient in accordance with exemplary embodiments of the disclosed subject matter.
Figure 38:
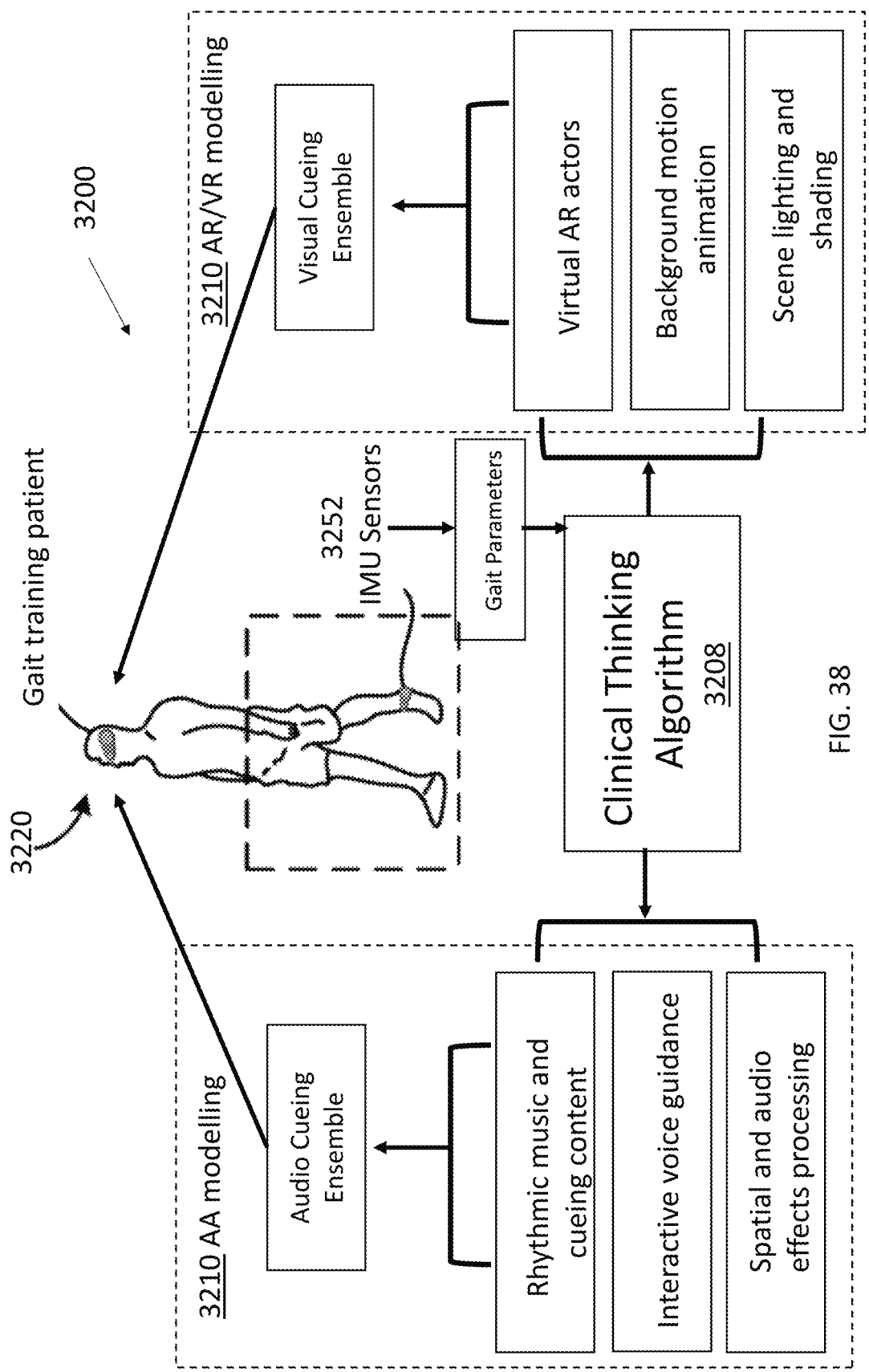
FIG. 38 is a hybrid system and process diagram conceptually illustrating the ANR system configured for implementing the gait-training technique in accordance with exemplary embodiments of the disclosed subject matter.

FIG. 37 is a process flow diagram illustrating an exemplary routine 3750 for providing gait training therapy to a patient using the ANR system 3200. FIG. 38 is a hybrid system and process diagram conceptually illustrating aspects of the ANR system 3200 for implementing the gait-training routine 3750 in accordance with exemplary embodiments of the disclosed subject matter. As shown, sensors 3252, particularly foot mounted IMUs, capture the sensor data relating to gait parameters that are provided to the CTA module 3208. Additionally, the AA/AR modelling component 3210 comprising an audio engine receives inputs from the CTA and is configured to generate an audio cueing ensemble comprising one or more of rhythmic music and cueing content, interactive voice guidance and spatial and audio effects processing. Similarly, the AA/AR modelling component 3210 comprising an AR/VR modelling engine (also referred to as AR 3-D dynamic model) is shown as receiving inputs from the CTA and is configured to generate a visual cueing ensemble comprising one or more of virtual AR actors and objects (e.g., a virtual person walking), background motion animation (e.g., virtual treadmill, steps/footprints and animations) and scene lighting and shading.

Figure 39:
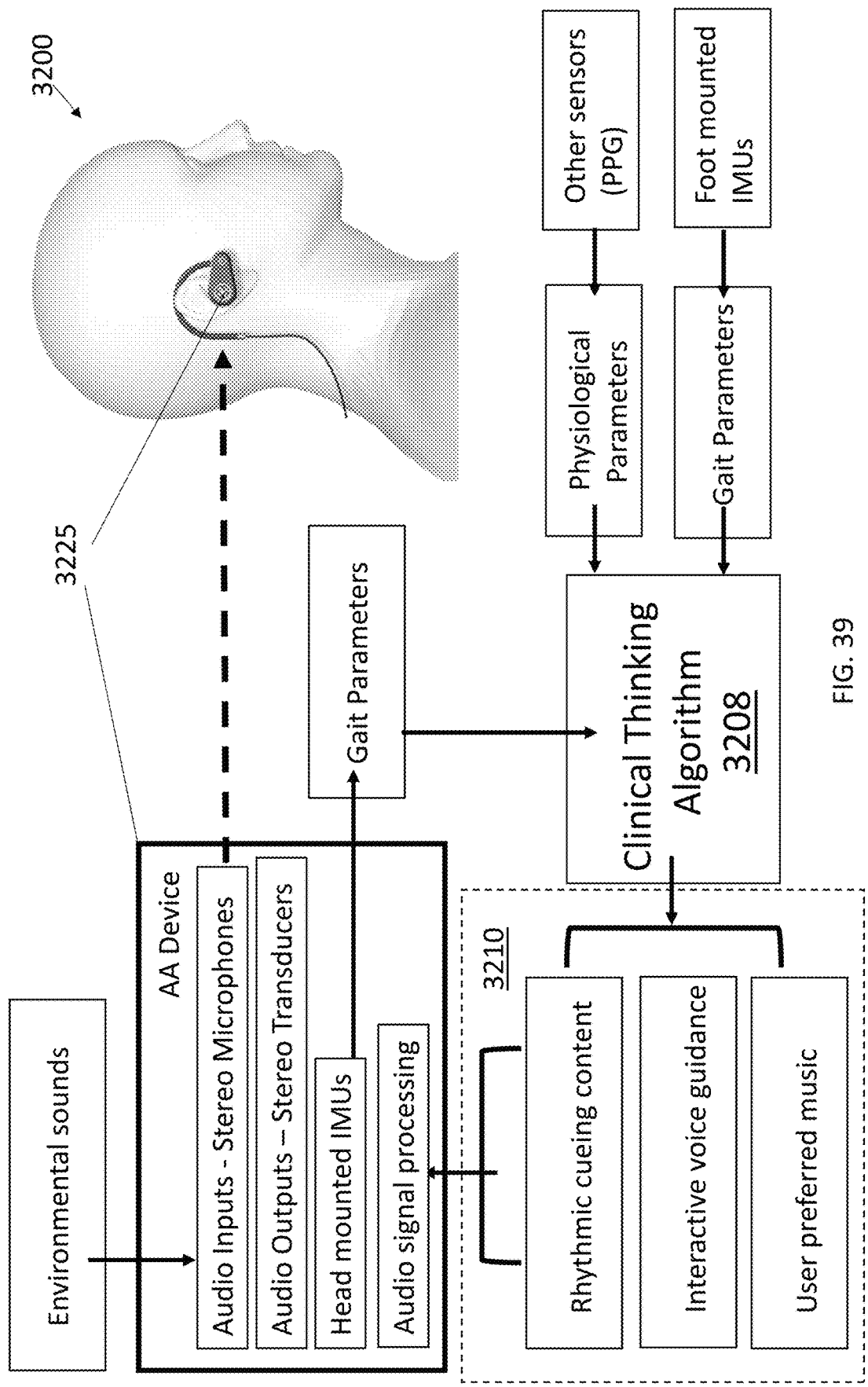
FIG. 39 is a hybrid system and process diagram conceptually illustrating the augmented audio (AA) device component of the ANR system of FIG. 38 in greater detail in accordance with exemplary embodiments of the disclosed subject matter.

FIG. 39 is a hybrid system and process diagram conceptually illustrating an exemplary audio output device 3225 and augmented audio generation components of the ANR system 3200 in greater detail. As shown in FIG. 39, in an embodiment, the AA device can capture environmental sounds using, for example, stereo microphones. The AA device can also generate audio outputs using stereo transducers. The AA device can also comprise head-mounted IMUs. As would be understood the AA device can also comprise audio signal processing hardware and software components for receiving, processing and outputting the augmented audio content received from the AA/AR module 3210 alone or in combination with other content such as environmental sounds. As shown, the CTA module 3208 receives gait parameters including those received from sensors including foot mounted IMUs and head mounted IMUs. Additionally, in an embodiment the CTA receives data relating to physiological parameters from other sensor devices such as PPG sensors.

Returning now to FIG. 37, at step 3700 a patient wearing the AR/AA output device 3220 and IMU sensor 3252 starts to walk as the ANR system 3200 calibrates and collects preliminary gait data such as stride length, speed, gait cycle time and symmetry. At step 3701 the CTA module 3208 determines the baseline rhythmic tempo for both the music playback and virtual AR scene to be displayed. For example, the baseline rhythmic tempo can be determined by the CTA as described in connection with FIG. 18.

With the user's gait cycle times as an input, at step 3702 the audio engine (i.e., the audio modelling component of AR/AA modelling module 3210) generates the corresponding tempo adjusted music along with any supplementary rhythmic cueing, such as a metronome sound, to reinforce the beat saliency.

At step 3703, the visual AR engine (i.e., the visual modelling component of AR/AA modelling module 3210) will generate a moving virtual scene, such as those understood in the video game industry. More specifically, in an embodiment, the virtual scene includes visual elements that are presented under the control of the CTA and share the common timing reference with the audio engine, in order to synchronize the elements of the visual scene to the music and rhythm tempo. Although the AR scene described herein includes a virtual treadmill or virtual person and footsteps, the AR scene could be any one or more of a variety of examples discussed herein, such as a virtual treadmill, a virtual person walking, a virtual crowd or dynamic virtual scene.

At steps 3704 and 3705, the music/rhythm and visual content are delivered to the patient using an AR/AA device 3220 such as a lightweight heads-up display (e.g., AR goggles 3222) with earphones 3225. Under the control of the CTA, the patient receives instructions at steps 3706 and 3707 regarding the therapy via voiceover cues generated by the audio engine. This could include a pre-walk training preview in order for the patient to become accustomed to and practice with the visual scenery and audio experience.

Figure 40:
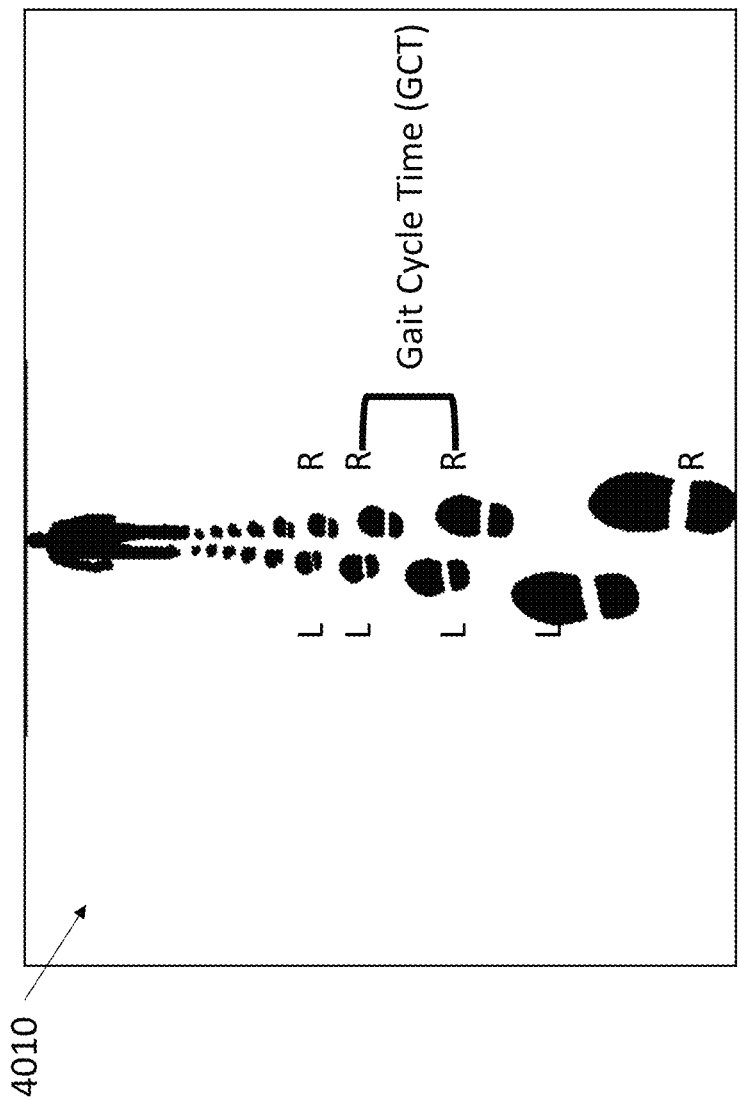
FIG. 40 is an exemplary AR display generated by the ANR system for display to the patient during a therapy session in accordance with exemplary embodiments of the disclosed subject matter.

FIG. 40 shows an exemplary AR virtual scene 4010 presented for the patient to entrain with. As shown, the scene can comprise an animated 3-D image of another person walking "in front" of the patient and whose steps and walking motions are synchronized to the music tempo. More specifically, in an embodiment, the AR actor walks to the same tempo as the baseline beat tempo of the audio content generated by the CTA and audio engine. In this example, the patient goal can be to match their steps both rhythmically with the audio, and visually with the actor. Additionally, as shown in FIG. 40, the AR scene can comprise a plurality of footsteps with additional cues such as L and R indicating left and right foot.

The scene including the footsteps can be virtually moving toward the patient at a prescribed rate, while the virtual actor is walking in front of the patient in the direction away from the patient. In an embodiment, the scene can be moving according to a gait cycle time, wherein GCT (right foot)/

2*60=music tempo defined by the CTA. Moreover, additional cues generated in connection with the AR scene can include rhythmic audio cues that reinforce the visual cues. For example, one effective reinforcement method can include the AA system 3210 generating the sound of the virtual actor's footfalls in synchrony with the rhythm, simulating group-marching to a common beat. By providing the patient with rhythmic audio components generated based on the visual stimulus in addition to timing the motion of visual elements with the rhythmic audio stimulus, the system further reinforces the virtuous cycle among the fundamental therapeutic concepts of entrainment and mirror neurons.

Figure 41:
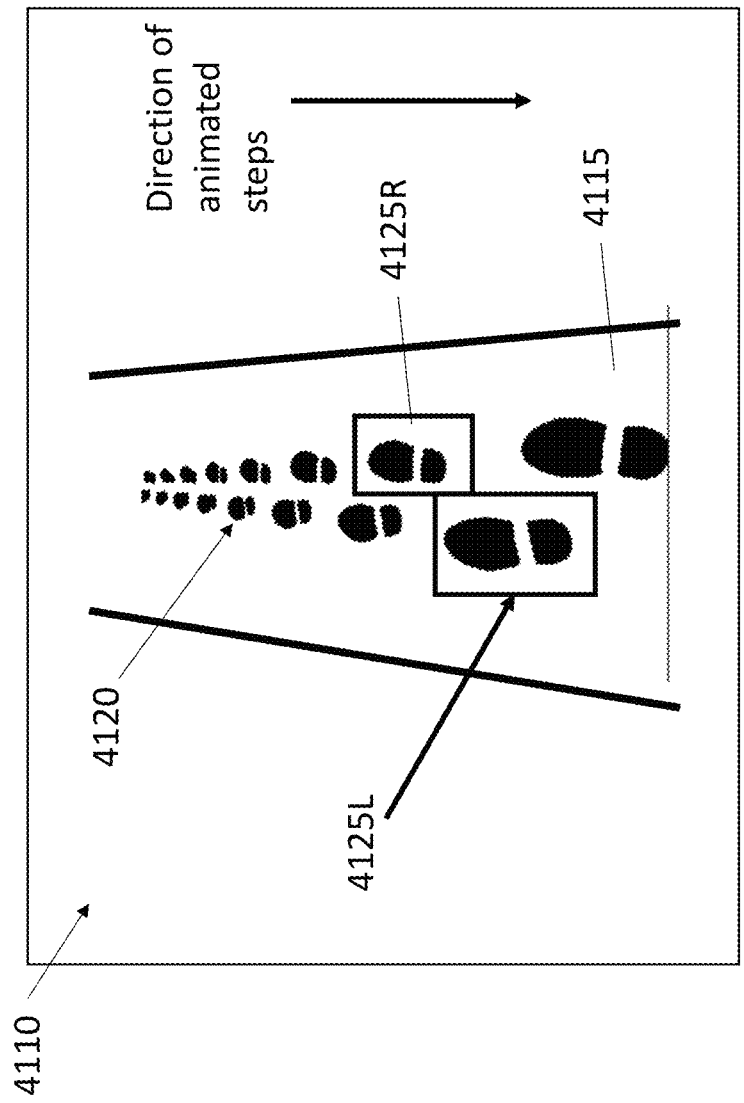
FIG. 41 is an exemplary AR display generated by the ANR system for display to the patient during a therapy session in accordance with exemplary embodiments of the disclosed subject matter.

By way of further example, FIG. 41 shows an exemplary AR virtual scene 4110 presented for the patient to entrain with. As shown in FIG. 41, the virtual treadmill can be generated and dynamically controlled based on entrainment of the patient towards target parameters such as those listed above as target parameters. In this example, the generated AR treadmill animates movement of the treadmill surface 4115 and generates virtual steps at the same tempo as defined by the CTA for the auditory stimulus. Additionally, the 3-D animation of a virtual treadmill could include visually highlighted steps or tiles that a patient can use as visual goals while simultaneously entraining to the rhythm generated under control of the CTA. Accordingly, in this example, the patient goal is to match their steps both rhythmically to the audio and visually with the animated goal steps. As further shown in FIG. 41, animated footsteps 4120 can be shown on the surface of the virtual treadmill 4115 moving in the direction toward the patient illustrated by the directional arrow, which may be reversed if the patient is performing a backwards-walking training exercise. Additionally, animations highlighting goal steps 4125L (left foot step) and/or 4125R (right foot step) are respectively highlighted in sync with CTA's rhythm to prompt the user to step with the corresponding foot (e.g., left or right). Additionally, as further described herein, the virtual scenes such as those shown in FIGS. 40-41, can be dynamically adjusted according to the patient's entrainment potential (EP) and corresponding changes to the audio stimulus. Other adjustments to the virtual scene can include changing the virtual background environment to simulate different walking scenarios, weather, surfaces, lighting and inclination.

Returning now to FIG. 37, as the patient starts to walk, at step 3708, the biomechanical sensors (e.g., sensors 3252) measure real-time data for use in evaluating the patient's entrainment level. At step 3709, the entrainment potential (e.g., as explained in FIG. 18) is determined by the CTA module 3208 and used to determine how the training session goal is to be met. As discussed in previous embodiments of the disclosure, entrainment potential can be the basis for modifying the rhythmic audio stimulus and visual scenery, which occurs at step 3710. For instance, the CTA analyses the incoming data history of the patient's gait cycle times in comparison to the rhythmic intervals of the beats delivered to the patient by the audio device. Exemplary approaches for modifying the audio stimulus based on entrainment potential are similarly described above. In one example, if the EP value calculated for the patient's steps over a period of time are not within a prescribed range of acceptable EP values and/or sufficiently consistent, then the CTA module can instruct the AA/AR modelling module to adjust (e.g., reduce) the tempo of the RAS and correspondingly adjust the motion speed of the AR scene in sync with the RAS. In a further example, if enough step times are in phase with the beat times, then the patient is considered to be entraining by the CTA.

Once entraining, at step 3711, the CTA evaluates whether the patient has reached a goal. If a goal has not been reached, then one or more target parameters can be adjusted at step 3712. For instance, in one example, the CTA compares the RAS tempo and associated AR scene speed to a target tempo parameter (e.g., a training/therapy goal) before a rhythmic tempo and/or scenery motion speed is changed in view of the comparison. Exemplary methods that the CTA module 3208 can implement for adjusting the rhythmic auditory stimulus according to entrainment potential are shown and described above, for example, in connection with FIG. 18.

For instance, if the patient has not reached their training speed goal, modifying the target parameters could include increasing or decreasing the music tempo at step 3712. This would drive the patient to walk faster or slower using the RAS mechanism of action. Alternatively, another training goal could be to lengthen a patient's stride length, which can be achieved by slowing down the imagery's motion speed parameter. By modifying the visual scenery, the patient would be driven to model the visual example presented to them using a mirroring mechanism of action.

It is important to understand that the audio and visual outputs are mutually reinforcing stimuli: the visual scenery is layered together in synchrony to the rhythmic stimulus. Depending on the program selected (e.g., the CTA), the CTA module 3208 makes dynamic adjustments to the visual scenery and rhythmic tempo in order to meet the therapy goal.

The foregoing example illustrates how the ANR system 3200 using the CTA module 3208 can control the synchronization of music tempo and AR scenery based on biomechanical sensor inputs in furtherance of gait training. It should be understood that the principles of this embodiment are applicable to many disease indications and rehabilitation scenarios.

Figure 33:
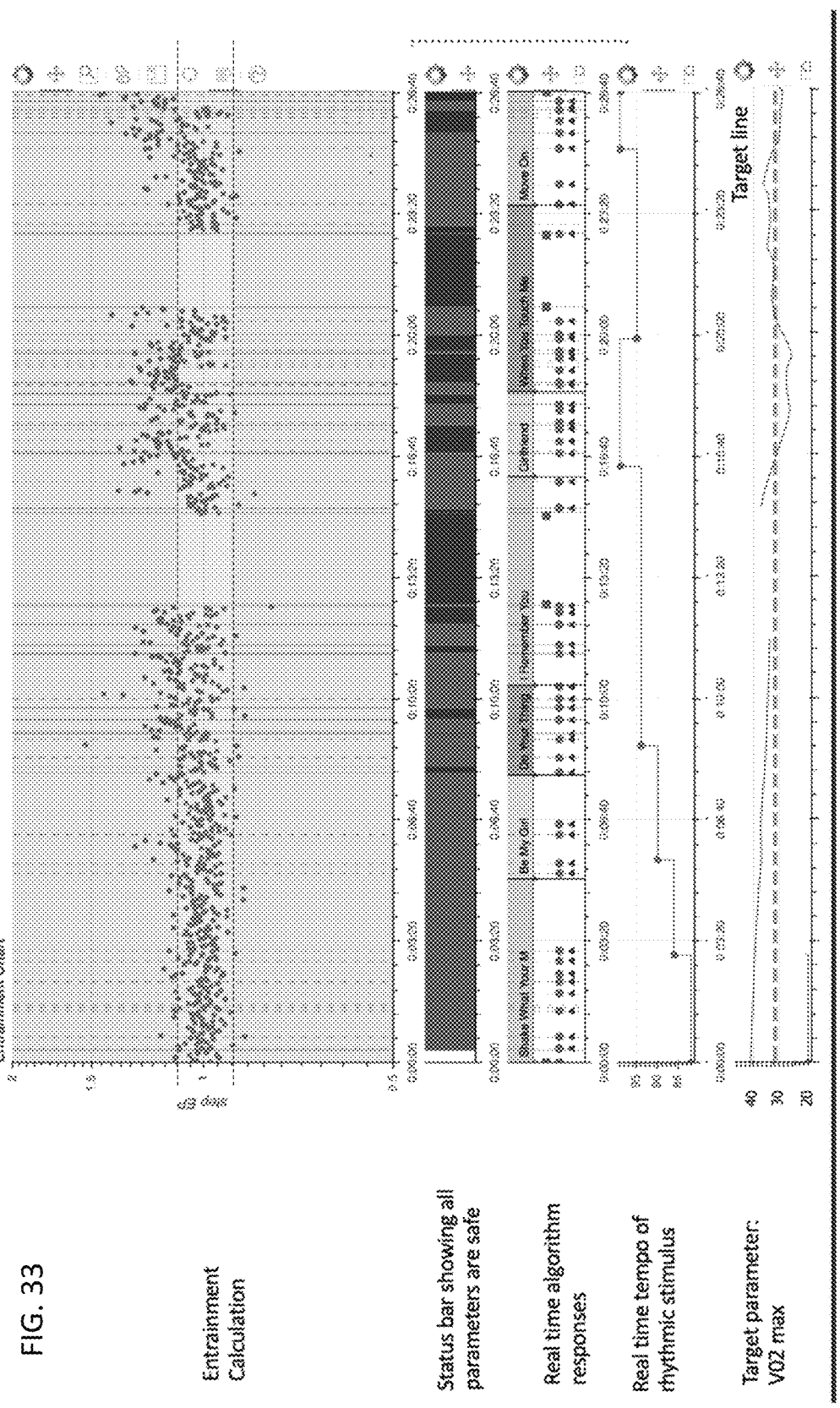
FIG. 33 is a graphical visualization of measured parameters, system responses and target/goal parameters during a therapy session performed using the ANR system of FIG. 32 in accordance with exemplary embodiments of the disclosed subject matter.

In an exemplary configuration, the virtual treadmill can be generated by the ANR system 3200 to modulate the patient's walking towards a target parameter of oxygen consumption. In this example, the virtual treadmill is generated and controlled in order to modulate the walking speed towards an oxygen consumption or efficiency target parameter using entrainment. FIG. 33 is a graphical visualization of a real time session performed using the ANR system 3200 with V02 max as target parameter, tempo changes used as interim goal, and entrainment used to drive the physiological changes related to v02 max. FIG. 33 shows an example of how this process works in real time. More specifically, FIG. 33 is a graphical user interface illustrating various salient data-points and parameter values that are measured, calculated and/or adjusted by the ANR system in real-time during a session. As shown, the top of the interface shows a chart of entrainment potential values calculated for each step in real-time throughout the session. In particular, the top bar shows individual EP calculated per step, which in this example is the phase correlation between step time intervals and beat time intervals. The central zone around EP=1 represents steps that are sufficiently entrained to the beat, or in other words, steps having an EP value within a prescribed range). The next window down provides a status bar showing whether parameters are within a safe range. The next window down shows a real time response driven by the CTA based on, inter alia, the measured parameters, entrainment and other aforementioned inputs and feedback to the CTA. In particular, the circle icons represent algorithm responses, which include both the tempo changes and rhythmic stimulus level (e.g. volume) changes. The bar below that shows just the tempo and tempo changes by themselves. The next window down shows the real-time tempo of rhythmic stimulus provided to the patient over time in accordance with the CTA response. The bottom window shows measured oxygen consumption over time and target parameter. Although not shown in FIG. 33, it should be understood that the patient can be presented with an augmented reality scene (e.g., the virtual treadmill) with visual elements animated in synchrony to the rhythmic stimulus and dynamically adjusted in synchrony the with the adjustments to the real time tempo of the rhythmic stimulus. An example of how the AA/VR module 3210 can be configured to synchronize the visual animation speed and audio can include defining the relationship between displayed repetitive motion rates and the tempo of the audio cues. For example, based on the beat tempo, the rate of the treadmill and spacing of the steps are calculated to define the relationships between audio and visual elements. Furthermore, a reference position of the treadmill, timing of the footsteps and any beat-timed animations are synchronized to the output time of the beats comprising the beat tempo. Using time scaling and video frame interpolation techniques known the animation industry, a wide range of synchronized virtual scenes can be programmatically generated by the AA/VR module 3210 on demand according to the defined relationships between audio and visual elements.

Figure 34:
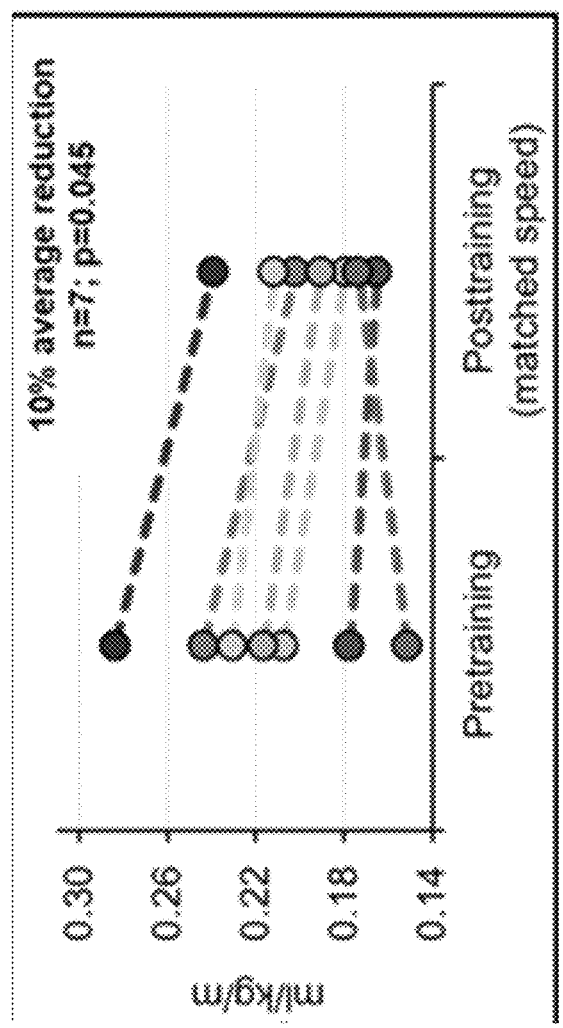
FIG. 34 is a graph depicting exemplary results relating to metabolic change resulting from a training session performed using the ANR system of FIG. 32 in accordance with exemplary embodiments of the disclosed subject matter.

FIG. 34 is a graph depicting Metabolic change during a first training session for 7 patients (denoted by respective sets of two dots connected by a dashed line). FIG. 34 shows data that supports purposely entraining can improve the oxygen consumption of an individual. In this instance, the graph shows a person's oxygen consumption (ml of oxygen/kg/meter) pre-training to rhythm and post-training to rhythm with the ANR system. This figure shows an average reduction of 10%. The results indicate that the entrainment process can improve endurance and reduce energy expenditure while walking.

This foregoing process can be similarly implemented for each of the various possible target parameters mentioned above (e.g., oxygen consumption could be exchanged for an alternative goal such as heart rate) and can be performed for walking or other interventions discussed in connection with FIGS. 18 through 31.

In accordance with one or more embodiments, the ANR system 3200 can be configured to compare real-time measured information concerning movements of a person to AR images and/or components of music content (e.g. instantaneous tempo, rhythm, harmony, melody, etc) being output to a patient during the therapy session. This can be used by the system to calculate an entrainment parameter, determine phase entrainment, or establish baseline and carryover characteristics. For example, the AR images could be moving at the same speed or cadence as the target parameter. Alternatively, the AR relevant movements of the images could be entrained to the rhythmic stimulus in synchrony with how the person should be moving.

Figure 35:
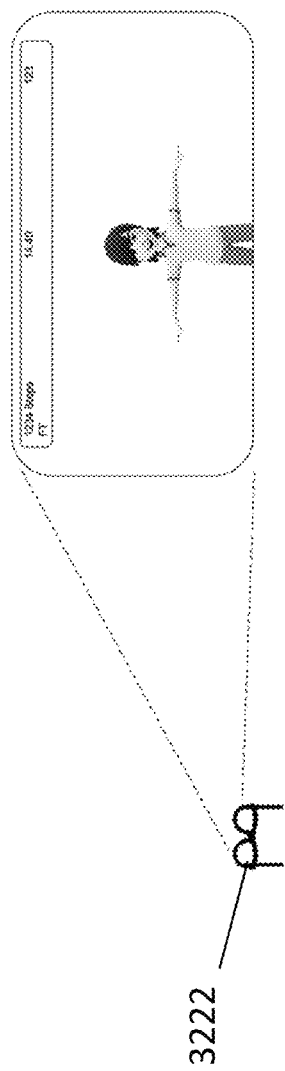
FIG. 35 is an exemplary augmented reality (AR) display generated by the ANR system for display to the patient during a therapy session in accordance with exemplary embodiments of the disclosed subject matter.

An example of an AR 3-D dynamic model output can include projecting a therapist (virtual actor) or person (virtual actor) walking in the patient's field of view which is initiated by the person performing the therapy (real therapist). FIG. 35, for instance illustrates the view of a therapist or coach projected in front of patient or trainer via AR, using for example AR glasses known in the art. This AR 3-D dynamic model is controlled with one or a variety of CTA's. In a combination of CTA's, the virtual therapist could start with the approach shown and described in connection with FIG. 22, and then have them proceed with a gait training regimen, like shown and described in connection with FIG. 18. Alternatively, these could be done simultaneously with dual tasking. During these instances, the virtual actor can be controllably displayed by the system as walking or moving backwards or forward with a smooth movement similar to the non-affected side of the patient. This could activate mirror neurons, which is where affected neurons are "encouraged" to mirror in performance non affected neurons. This process can also include providing an audio stimulus to sync the virtual and/or physical person to the stimulus.

Figure 36A:
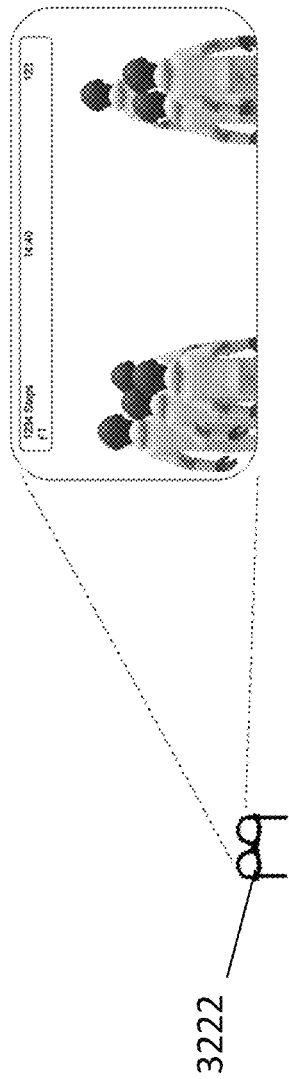
FIG. 36A is an exemplary AR display generated by the ANR system for display to the patient during a therapy session in accordance with exemplary embodiments of the disclosed subject matter.

In another example, the AR 3-D dynamic model can be configured to simulate a scenario in which the patient is walking in or around a crowd of people and/or people with objects in front and/or the side of the patient. FIG. 36A, for example, illustrates the view of a crowd of people projected in front of the patient via AR. The system can be configured to project the crowd or person traveling faster or slower than the baseline of the person to encourage them to move at a similar speed or stopping/starting in a real-world environment. The crowd or person could be entrained to the beats of the rhythmic auditory stimulus or another desired goal. Varying levels of difficulty in navigation can be initiated by the AR 3-D dynamic model. As should be understood, the AR view of a therapist, crowd, person, obstacles and the like can be dynamically adjusted using the AR 3-D dynamic model according to the output of the CTA's.

In another example, the AR 3-D dynamic model can be configured to simulate a scenario in which the patient is walking in or around an arrangement of cones which implements a virtual obstacle course for the patient to navigate. Cones are a normal obstacle in a therapy environment, however other embodiments of this could be configured to simulate normal activities of daily living (e.g., grocery shopping). These cones, along with virtual obstacles can encourage direction changes by virtue of walking with side steps to each side and walking backwards, rather than just forward walking directional changes. Here too, wireless beacon triggers can be used to cause the ANR system to present cones that appear and/or disappear. The beacons would be triggered based on detecting the location of the person related to the cones. In addition, varying levels of difficulty in navigation time and length can be initiated. The target parameter for this example can be a measure of walking speed or walking quality. Successful navigation would be to navigate around the cones without virtually hitting them. The system can be configured to present levels that get more difficult (e.g. more obstacles and faster speeds) as long as the person is successfully avoiding the obstacles and the quality of walking does not degrade (as measured by increase in variability or worsening asymmetry).

In another example, the AR 3-D dynamic model can be configured to simulate a scenario in which the patient is walking in or around caves and/or cliffs which can include obstacles for a reality effect. The realism would heighten details required for navigation over the prior presented use cases. In another example with a person with an asymmetrical gait pattern, a winding path can be presented where it requires a person to take a longer step on their affected side. This winding path could also be separate cliffs that they have to step over a valley to not fall off. Wireless beacon triggers can be used to cause the ANR system to make cave and/or cliff obstacles appear and/or disappear, thus varying levels of difficulty in navigation times and path lengths. Sensor data can be used by the system to sync movements to the winding path. The navigation requirements by the patient could be biomechanical responses for navigating changes in a baseline prescribed course. The system is configured such that wireless spatial and temporal beacon triggers affect the changes in the AR 3-D dynamic model. The temporal aspect of these wireless triggers is the ability to turn them on and off. This would allow for maximum flexibility in scripting navigation paths for the courses that patients should take as part of the therapy sessions. The target parameter for this instant is a measure of walking speed or walking quality. Successful navigation would be to navigate the paths without stepping off the path or falling off the cliff. The system can be configured to present levels that would get more difficult (e.g. more obstacles and faster speeds) as long as the person is successfully staying on the path and the quality of walking does not degrade (as measured by increase in variability or worsening asymmetry).

Figure 36B:
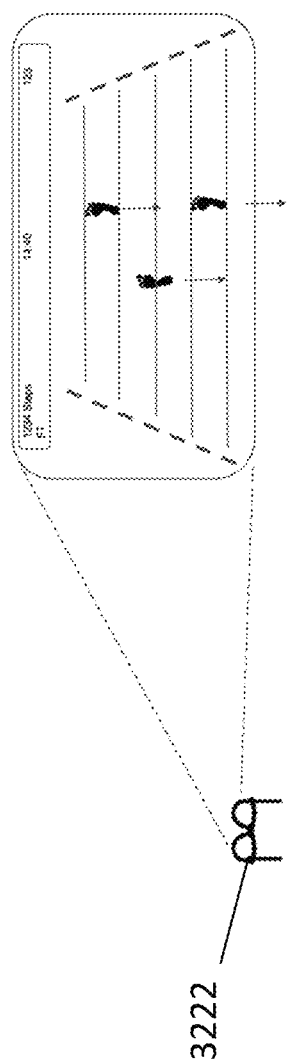
FIG. 36B is an exemplary AR display generated by the ANR system for display to the patient during a therapy session in accordance with exemplary embodiments of the disclosed subject matter.

In another example, the AR 3-D dynamic model can be configured to simulate a scenario in which the patient is standing or seated stationary and asked to march as a virtual object is presented and approaches each foot. FIGS. 36B, for example, illustrates the view of foot prints projected in front of patient via AR. The ANR system can generate a virtual scene in which the object may approach to the left or right of the patient to encourage side stepping. The object will be presented as approaching the patient at a pre-defined tempo or beat which will follow a decision tree as described in FIG. 22. A visual of the correct movement by therapist or patient from past therapy may also be projected.

In another exemplary AR 3-D dynamic model implementation, the ANR system can be configured to incorporate haptic feedback into the therapy. Haptic feedback, for example, can be employed by the system as a signal if the user gets too close to objects or people in the projected AR surrounding. Rhythmic haptic feedback may also be synced with the auditory cue to amplify sensory input. AR may also be adaptively and individually enabled to cue initiation of movement, for example, during a freezing of gait episode in someone with Parkinson's Disease.

In another exemplary AR 3-D dynamic model implementation, the ANR system can be further configured to incorporate optical and head tracking. This tracking may be incorporated as feedback to the ANR system configured to trigger auditory input in response to where their eyes or head is facing. For example, someone with left neglect who is interacting with only the right side of their environment, the eye and head tracking can provide input into how much of their left hemisphere environment is being engaged and trigger the system to generate an auditory cue to drive more attention to the left hemisphere. This data can also be used to track progress over time, as clinical improvement can be measured by degrees of awareness in each hemisphere. Another example of this is with people who have ocular motor disorders, where visual scanning from left to right may be improved by doing it to an external auditory rhythm.

In another exemplary AR 3-D dynamic model implementation, the ANR system can be configured to provide a digital presence of past sessions to display a user's improvement. These models could be replayed after a session to compare from session to session or the lifetime of the treatment. The digital presence of past sessions (or augmented session), when paired with the audio input of that session, could be used as a mental imagery task for practice in between walking sessions and limit fatigue. The model would display differences in walking speed, cadence, stride length, and symmetry to help show the users changes over time and how the treatment may be improving their gait. This presence could also be used by therapists before a session to help prepare training plans or techniques for follow-on sessions. This modeled presence could also be used by researchers and clinicians to better visualize and reanimate in 3-D imagery the evolution of a patient's progress.

In another exemplary AR 3-D dynamic model implementation, The AR/VR environments synced with the music content could create different walking or dance patterns to include ovals, spirals, serpentines, crossing paths with others, and dual task walking. Dance rhythms such as a Tango have been shown to have benefits stemming from Neurologic Music Therapy (NMT) and RAS that can apply to the entire human body.

In accordance with one or more embodiments, the ANR system can be configured to utilize AA techniques to enhance the entrainment process, provide environmental context to a person, and aid in the AR experience. To enhance the recovery process, the system can be configured to generate the exemplary AA experiences further described herein based on inputs taken from the environment, sensor data, AR environments, entrainment, and other methods.

An example of AA of a therapy/medical use case would be to address safety concerns and mitigate risk to patients who are performing therapy exercises. The ANR system can be configured to improve situational awareness while listening to music with headphones by mixing external sounds that exceeds a minimum audio loudness threshold instantaneously into the therapy's rhythmic and audio cueing content. An example of an external sound would be the honking of a car or the sirens of an emergency vehicle, which would in synchrony automatically interrupt the normal auditory stimulus to provide awareness to the person as to the potential for danger. To perform this function and other functions, the listening apparatus could have additional microphones and digital signal processing dedicated to performing this task.

In a further embodiment, the ANR system implementing AA can be configured to combine aspects of AA and the manipulation of spatial perception by aligning the rhythmic auditory cueing with a patient's "affected side" while they are performing a walking therapy session. If, for example, the right side of the patient requires a greater degree of therapy, the audio cueing content can be spatially aligned with the right side for emphasis. Exemplary systems and methods for neurologic rehabilitation using techniques for side-specific rhythmic auditory stimulus are disclosed in co-pending and commonly assigned U.S. Patent Application No. 62/934,457, titled SYSTEMS AND METHODS FOR NEUROLOGIC REHABILITATION, filed on Nov. 12, 2019, which is hereby incorporated by reference as if set forth in its entirety herein.

In a further embodiment, the ANR system implementing AA can be configured to provide unique auditory cueing to increase spatial awareness of head position while gait training, encouraging the user to keep head up, at midline and eyes forward, improving balance and spatial awareness while going through an entrainment process or other CTA experience.

In a further embodiment, the ANR system implementing AA can be configured to provide binaural beat sound and tie it into human physiology (e.g. breathing rate, electrical brain activity (EEG) and heart rate) to improve cognition and enhance memory. The ANR system can be configured to provide the binaural beat audio signal input in complement to RAS signal input. The real-time entrainment and quality of gait measurements being made by the system would likewise be complemented by physiological measurements. For instance, the system as configured for binaural beat audio uses differential frequency signals output in the left and right ears, whose difference is 40 Hz—the "Gamma" frequency of neural oscillation. These frequencies can reduce amyloid buildup in Alzheimer's patients and can help with cognitive flexibility. By delivering such audio signal via the AA device to the user while they perform RAS gait training, a second type of neural entrainment can be achieved simultaneously with the biomechanical-RAS entrainment. The network hypothesis of brain activation implies that both walking and cognition would be impacted. Such auditory sensory stimulation would therefore entrain neural oscillations in the brain while rhythmic auditory stimulation entrains the motor system.

In a further embodiment, the ANR system implementing AA can be configured to provide a phase coherent soundstage (e.g. the correct audio spatial perspective) when a patient rotates their head or changes its attitude. A sound stage is the imaginary 3-D image created by stereo speakers or headphones. It allows the listener to accurately hear the location of sound sources. An example of manipulating the soundstage in a therapeutic session would be keeping the voice sound of a virtual coach "in-front" of the patient, even while their head may be turned to the side. This feature could help avoid disorientation, thus creating a more stable, predictable and safe audio experience while performing the therapy. This feature could be combined with the AR virtual coach/therapist in front of a person in FIG. 34. It could also be combined with knowledge of the course or the direction the person needs to take in the real world.

In a further embodiment, the ANR system can be configured to combine AA with Augmented Reality (AR) in such a manner that as the patient synchronizes with a virtual crowd, the virtual sound effects (e.g. encouragements and crowd footsteps) create a coherent soundstage with regard to the patient's visual gaze. The audio could also create a perception of distance from, or nearness to, an object. Changing spatial location or loudness in such manner could also be used as a goal target in combination with AR and 3-D imagery.

In a further embodiment, the ANR system can be configured to combine AA with Augmented Reality (AR) in such a way to create virtual instrument therapy. Instruments such as bells, drums, piano, and guitar can be common training tools for patients. By creating digital models of these instruments and providing an AA feedback upon interaction, the patient can be given an immersive experience and the perception that they are physically playing an instrument. This could be modified for difficulty to help the progression of a patient over time and show improvements. Examples of modifications could include adding more keys on a piano or more strings on a guitar. In addition to virtual instruments, virtual sheet music or musical notation could be displayed in real time as the patient is playing the instruments, either virtual instruments or real instruments. Other examples could be in combination with the concepts discussed in connection with FIG. 19, wherein the connected hardware could be replaced by AR. Similar logic could be used to other of the documented interventions.

In a further embodiment, the ANR system can be configured to implement AA in combination with a telepresence to provide a spatially accurate audio experience for the therapist. The audio could also be generated to create a perception of distance from, or nearness to, an object. By changing spatial location or loudness of the AA and leveraging the AR model, the system can be used to determine more effectively if the patient is meeting goals associated with playing the virtual devices and provide them with a more accurate special experience.

In accordance with one or more embodiments, the ANR system can implement a type of AA, namely, a Rhythmic Stimulus Engine (RSE). The rhythmic stimulus engine is a bespoke rhythmic auditory stimulus, which embodies the principles of entrainment to drive a therapeutic benefit while generating original and custom auditory rhythmic content for the patient. For some disease states such as Parkinson's, it could also be beneficial to have a constant rhythm "soundtrack" in the patient's environment. An RSE could be configured to perform this continuous background rhythmic neurostimulation without the need to access pre-recorded music. In one example, the ANR system can be configured to implement AA in combination with the Rhythmic Stimulus Engine (RSE) and AR to create a completely synchronized feedback state between incoming biometric data, external audio inputs from the therapy environment, to the generated rhythmic content, AR and AA outputs. In another example, the system can be configured to modulate the tempo of the rhythmic audio content generated by an RSE by the walking cadence of the patient in an interactive fashion. In another example, the tempo and time signature of the rhythmic audio content generated by the RSE could be modulated by the entrainment precision and beat factor of the patient user, such as one using a cane or assistive device in an interactive fashion. In another example, an RSE could provide the neurostimulation that, in combination with assistive technologies such as exo-suits, exo-skeletons and/or FES devices, increases the effectiveness of walking therapy. In another example, an RSE could generate from a stored library of traditional dance rhythm templates, the rhythmic audio content that could extend therapy to the patient's upper body and limbs. This could be extended to combine with AR techniques mentioned above, such as a dancing crowd or virtual dancefloor. In another example, machine learning techniques such as self-learning AI and/or a rules-based system could generate rhythm in real-time moderated by inertial motion units (IMUs) inputs that report cadence and quality of gait parameters, such as symmetry and gait cycle time variability. Using an unsupervised ML clustering or decision-tree model, various gait patterns could act as inputs to the generative music system.

In accordance with one or more embodiments, the ANR system can implement a type of AA, namely, Sonification, which means applying varying amounts of signal distortion to the music content depending on how close to or far from a patient is to a target goal. The degree and type of sonification helps nudge the patient to a correction state. The novel combination of sonification and entrainment could provide a feed-forward mechanism for auditory motor synchrony through entrainment, while simultaneously providing a feedback mechanism via distortion of the music content of some other biomechanical or physiological parameter that the individual can adjust. For example, adding signal distortion to the music signal while increasing the volume of the rhythmic cueing could in combination have greater effectiveness than either method by itself.

In accordance with one or more embodiments, the ANR system can implement CTA in combination with a neurotoxin injection is as follows. The CTA could apply the entrainment principle to work towards improving a motor function, such as gait. The neurotoxin injection can also be used to target gait improvements by targeting spasticity in the muscles. These injections take 2-4 days to take effect and last up to 90 days of effect (e.g. effectiveness period). The dosing of the CTA for entrainment principles (e.g., the setting of one or more parameters of the CTA) could be targeted towards the effectiveness curve of the neurotoxin injection, where training is done less intense in the period before the injection takes effect and increases during the effectiveness period.

In accordance with one or more embodiments, the ANR system can be configured to calculate entrainment parameter using the syncing of the heartbeat or the respiration rate to the music content, instead of the biomechanical movement parameter. An example of a use case is for people with agitation from various forms of dementia, Alzheimer's, bi-polar disorder, schizophrenia, etc. In this use case, the baseline parameter could be determined by the heart rate or respiration rate. The entrainment or phased entrainment could be determined by the comparison of the music content to the heart rate or respiration. Additionally, goals could be set to lower the amount of agitation to enhance the quality of life of these people.

As can be appreciated from the foregoing discussion, systems for augmented neurologic rehabilitation of a patient in accordance with one or more embodiments of the disclosure can comprise one or more of the following points:

A computing system for having one or more physical processors configured by software modules comprising machine-readable instructions. The software modules can include a 3D AR modelling module that, when executed by the processor, configures the processor to generate and present augmented-reality visual and audio content to a patient during a therapy session. The content includes visual elements moving in a prescribed spatial and temporal sequence and rhythmic audio elements output at a beat tempo.

The computing system also includes an input interface in communication with the processor for receiving inputs including time-stamped biomechanical data of the patient relating to the movements performed by the patient in relation to the AR visual and audio content and physiological parameters measured using one or more sensors associated with the patient.

The software modules also include a critical thinking algorithm that configures the processor to analyze the time-stamped biomechanical data to determine a spatial and temporal relationship of the patient's movements relative to the visual and audio elements and determine a level of entrainment of the patient relative to a target physiological parameter. Additionally, the 3D AR modelling module further configures the processor to dynamically adjust the augmented-reality visual and audio content output to the patient based on the determined level of entrainment relative to the target parameter.

The above systems, devices, methods, processes, and the like may be realized in hardware, software, or any combination of these suitable for an application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in several ways. At the same time, processing may be distributed across devices such as the various systems described above, or all the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless an order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure.

What is claimed is:

1. A system for augmented neurologic rehabilitation of a patient, comprising:
a computing system having a processor configured by software modules comprising machine-readable instructions stored in a non-transitory storage medium, wherein the software modules include:
an AA/AR modelling module that, when executed by the processor, configures the processor to generate an augmented-reality (AR) visual content and rhythmic auditory stimulus (RAS) for output to a patient during a therapy session, wherein the RAS comprises beat signals output at a beat tempo and wherein the AR visual content includes visual elements moving in a prescribed spatial and temporal sequence based on the beat tempo;
an input interface in communication with the processor for receiving real-time patient data including time-stamped biomechanical data of the patient relating to repetitive movements performed by the patient in time with the AR visual content and RAS, and wherein the biomechanical data is measured using a sensor associated with the patient; and
wherein the software modules further include:
a critical thinking algorithm (CTA) module that configures the processor to analyze the time-stamped biomechanical data to determine a temporal relationship of the patient's repetitive movements relative to the visual elements and beat signals output at the beat tempo to determine a level of entrainment; and
wherein the AA/AR modelling module further configures the processor to dynamically adjust the AR visual and RAS output to the patient in synchrony and based on the determined level of entrainment, wherein dynamically adjusting the AR visual content includes adjusting the prescribed spatial and temporal sequence of the visual elements based on the determined level of entrainment.

2. The system of claim 1, wherein the processor dynamically adjusts the AR visual content and RAS based on the determined level of entrainment by, adjusting the beat tempo of the RAS in view of the level of entrainment, and adjusting the prescribed spatial and temporal sequence of the visual elements in synchrony with the adjusted beat tempo.

3. The system of claim 2,
wherein the beat signals are each output at a respective output time;
wherein the level of entrainment is determined based on a timing of the repetitive movements relative to the respective output times of the beat signals.

4. The system of claim 3, wherein the CTA module configures the processor to determine the level of entrainment by:
analyzing the time-stamped biomechanical data to identify a respective time of respective repetitive movements,
measuring a temporal relationship between the respective time of one or more repetitive movements and a respective output time of one or more associated beat signals,
calculating an entrainment potential based on the measured temporal relationship for one or more of the respective repetitive movements; and
wherein the processor is configured to dynamically adjust one or more of the AR visual and RAS output based on the entrainment potential.

5. The system of claim 2,
wherein the CTA module further configures the processor to determine, based on one or more of physiological data measured for the patient and the bio-mechanical data, whether the one or more of the bio-mechanical data or the physiological data meets a training goal parameter;
wherein the AA/AR modelling module further configures the processor to dynamically adjust the AR visual content and RAS output to the patient in response to the training goal parameter being unmet by adjusting the beat tempo of the RAS in view of the training goal parameter being unmet, and adjusting the prescribed spatial and temporal sequence of the visual elements in synchrony with the adjusted beat tempo.

6. The system of claim 5, wherein the training goal parameter is a rehabilitation outcome.

7. The system of claim 1, further comprising:
an AR video output device configured to present the AR visual content to the patient;
an audio output device configured to output the RAS to the patient; and
the sensor associated with the patient and configured to measure the time-stamped biomechanical data of the patient, wherein the sensor comprises an inertial measurement unit (IMU) device.

8. The system of claim 5, further comprising:
a sensor associated with the patient and configured to measure physiological data of the patient, and wherein the training goal parameter is a physiological parameter, and
wherein the physiological parameter is one or more of: heartrate, blood oxygenation, respiratory rate, VO2, electrical brain activity (EEG).

9. The system of claim 2, wherein the AR visual content comprises a visual scene including one or more of:
a virtual treadmill animated to appear as if a top surface of the treadmill is approaching the patient at a rate that corresponds to the beat tempo, and
a plurality of footprints superimposed on a top surface of the virtual treadmill, wherein the footprints are arranged spatially and appear to approach the patient at a rate that corresponds to the beat tempo, and
an animated person performing the repetitive motion at a rate that corresponds to the beat tempo.

10. The system of claim 9, wherein modifying the AR visual content comprises one or more of: changing a spacing of the footprints in view of a change in the beat tempo, changing the rate at which the animated person performs the repetitive motion, changing the rate at which the virtual top surface of the treadmill appears to be approaching the patient, changing the rate at which virtual obstacles or scene perturbations appear to the patient.

11. A method for augmented neurologic rehabilitation of a patient having a physical impairment, the method being implemented on a computer system having a physical processor configured by machine-readable instructions which, when executed, perform the method, comprising:
    providing rhythmic auditory stimulus (RAS) for output to a patient via an audio output device during a therapy session, wherein the RAS comprises beat signals output at a beat tempo;
    generating augmented-reality (AR) visual content for output to a patient via an AR display device, wherein the AR visual content includes visual elements moving in a prescribed spatial and temporal sequence based on the beat tempo and output in synchrony with the RAS;
    instructing, the patient to perform repetitive movements in time with the beat signals of the RAS and corresponding movement of the visual elements of the AR visual content;
    receiving real-time patient data including time-stamped biomechanical data of the patient relating to repetitive movements performed by the patient in time with the AR visual content and RAS, and wherein the biomechanical data is measured using a sensor associated with the patient;
    analyze the time-stamped biomechanical data to determine a temporal relationship of the patient's repetitive movements relative to the visual elements and beat signals output according to the beat tempo to determine an entrainment potential;
    dynamically adjusting the AR visual content and RAS for output to the patient in synchrony and based on the determined entrainment potential, wherein dynamically adjusting the AR visual content includes adjusting the prescribed spatial and temporal sequence of the visual elements based on the determined entrainment potential;
    continuing the therapy session using the adjusted AR visual content and RAS.

12. The method of claim 11, further comprising:
    measuring the biomechanical data from the patient, wherein measuring the biomechanical data from the patient comprises providing a sensor associated with the patient and measuring one or more of motion, acceleration and pressure associated with movement of the patient.

13. The method of claim 11, wherein dynamically adjusting the AR visual content and RAS based on the determined entrainment potential includes, adjusting the beat tempo of the RAS based on the entrainment potential, and adjusting the prescribed spatial and temporal sequence of the visual elements in synchrony with the adjusted beat tempo.

14. The method of claim 13, further comprising:
    comparing the beat tempo to a training goal parameter comprising a goal beat tempo; and
    dynamically adjusting the RAS and the AR visual content as a function of the comparison and the entrainment potential determined in regard to the beat tempo.

15. The method of claim 14, further comprising, if the entrainment potential meets a prescribed level and the beat tempo is below the goal beat tempo, increasing the beat tempo of the RAS towards the goal beat tempo and adjusting the prescribed spatial and temporal sequence of the visual elements in synchrony with the adjusted beat tempo.

16. The method of claim 11, wherein the beat signals are each output at a respective output time according to the beat tempo, wherein measuring the entrainment potential comprises comparing a respective onset time of each of a plurality of repetitive movements with the respective output-time of the associated beat signals in real-time, and wherein the onset time for a given repetitive movement is a time at which a prescribed identifiable event occurs during the given repetitive movement.

17. The method of claim 11, further comprising:
    determining, based on one or more of physiological data measured for the patient and the bio-mechanical data, whether the one or more of the bio-mechanical data or the physiological data meets a training goal parameter;
    wherein the AA/AR modelling module further configures the processor to dynamically adjust the AR visual content and RAS output to the patient in response to the training goal parameter being unmet.

18. The method of claim 17, further comprising:
    measuring the physiological data from the patient, wherein measuring the physiological data from the patient comprises providing a sensor associated with the patient configured to measure a physiological parameter, wherein the physiological parameter is selected from the group consisting of heart rate, respiratory rate and VO2 max.

19. The method of claim 11, wherein the AR visual content comprises a visual scene including one or more of:
    a virtual treadmill animated to appear as if a top surface of the treadmill is approaching the patient at a rate that corresponds to the beat tempo, and
    a plurality of footprints superimposed on a top surface of the virtual treadmill, wherein the footprints are arranged spatially and appear to approach the patient at a rate that corresponds to the beat tempo, and
    an animated person performing the repetitive motion at a rate that corresponds to the beat tempo.

* * * * *